(12) United States Patent
Krulevitch et al.

(10) Patent No.: US 7,654,127 B2
(45) Date of Patent: Feb. 2, 2010

(54) MALFUNCTION DETECTION IN INFUSION PUMPS

(75) Inventors: Peter Krulevitch, Pleasanton, CA (US);
Mingqi Zhao, San Jose, CA (US);
Sebastian Bohm, Los Gatos, CA (US);
Deon Anex, Livermore, CA (US);
Michael Gearhart, Fremont, CA (US)

(73) Assignee: Lifescan, Inc., Milpitas, CA (US)

( * ) Notice: Subject to any disclaimer, the term of this patent is extended or adjusted under 35 U.S.C. 154(b) by 375 days.

(21) Appl. No.: 11/614,211

(22) Filed: Dec. 21, 2006

(65) Prior Publication Data

US 2008/0154187 A1    Jun. 26, 2008

(51) Int. Cl.
*G01F 25/00* (2006.01)
*G01N 19/00* (2006.01)
(52) U.S. Cl. ...................... 73/1.16; 73/865.9
(58) Field of Classification Search ................ 73/1.01, 73/1.16, 1.17, 1.36, 1.57, 865.9
See application file for complete search history.

(56) References Cited

U.S. PATENT DOCUMENTS

| | | | |
|---|---|---|---|
| 3,623,474 A | 11/1971 | Heilman et al. | |
| 3,701,345 A | 10/1972 | Heilman et al. | |
| 4,273,122 A | 6/1981 | Whitney et al. | |
| 4,320,757 A | 3/1982 | Whitney et al. | |
| 4,342,312 A | 8/1982 | Whitney et al. | |
| 4,364,385 A * | 12/1982 | Lossef ....................... 424/424 | |
| 4,529,401 A | 7/1985 | Leslie et al. | |
| 4,541,787 A | 9/1985 | DeLong | |
| 4,636,144 A | 1/1987 | Abe et al. | |
| 4,779,614 A | 10/1988 | Moise | |
| 4,833,384 A | 5/1989 | Munro et al. | |
| 4,838,857 A | 6/1989 | Strowe et al. | |
| 4,884,013 A | 11/1989 | Jackson et al. | |
| 4,921,480 A | 5/1990 | Sealfon | |
| 4,943,279 A | 7/1990 | Samiotes et al. | |
| 4,952,205 A | 8/1990 | Mauer et al. | |
| 5,078,683 A | 1/1992 | Sancoff et al. | |
| 5,250,027 A | 10/1993 | Lewis et al. | |
| 5,378,231 A | 1/1995 | Johnson et al. | |
| 5,411,482 A | 5/1995 | Campbell | |

(Continued)

FOREIGN PATENT DOCUMENTS

WO    WO 03/071930    9/2003

OTHER PUBLICATIONS

Owner's Manual, Alza E-Trans Transdermal Delivery, Alza Corporation, Mountain View, California, Jun. 17-18, 2003 (4 pgs).

(Continued)

*Primary Examiner*—John Fitzgerald

(57) ABSTRACT

The present application is directed to systems and methods associated with infusion pumps, which can optionally utilize an electrokinetic driving mechanism. Infusion pumps, including electrokinetically-driven pumps, are discussed, along with schemes for controlling their operation. As well, systems and methods of detecting malfunctions in infusion pumps are discussed. Any number of malfunctions can be detected including the presence of occlusions and/or leaks. In some instances, a measurement associated with some aspect of electrokinetic phenomena (e.g., an electrode measurement such as voltage or current) is compared with one or more sample values, the comparison allowing an indication of pump malfunction to be determined. A variety of such measurements and comparison techniques are discussed in the present disclosure.

12 Claims, 23 Drawing Sheets

U.S. PATENT DOCUMENTS

| | | | |
|---|---|---|---|
| 5,453,382 A | 9/1995 | Novotny et al. | |
| 5,478,211 A | 12/1995 | Dominiak et al. | |
| 5,482,438 A | 1/1996 | Anderson et al. | |
| 5,482,446 A | 1/1996 | Williamson et al. | |
| 5,647,853 A | 7/1997 | Feldmann et al. | |
| 5,658,133 A | 8/1997 | Anderson et al. | |
| 5,882,338 A | 3/1999 | Gray | |
| 5,982,401 A * | 11/1999 | Fassler et al. | 346/140.1 |
| 5,985,119 A | 11/1999 | Zanzucchi et al. | |
| 5,997,501 A | 12/1999 | Gross et al. | |
| 6,013,057 A | 1/2000 | Danby et al. | |
| 6,013,164 A | 1/2000 | Paul et al. | |
| 6,019,745 A | 2/2000 | Gray | |
| 6,019,882 A | 2/2000 | Paul et al. | |
| 6,120,665 A | 9/2000 | Chiang et al. | |
| 6,129,517 A | 10/2000 | Danby et al. | |
| 6,129,668 A | 10/2000 | Haynor et al. | |
| 6,164,921 A | 12/2000 | Moubayed et al. | |
| 6,171,276 B1 | 1/2001 | Lippe et al. | |
| 6,195,887 B1 | 3/2001 | Danby et al. | |
| 6,211,670 B1 | 4/2001 | DeWilde et al. | |
| 6,213,723 B1 | 4/2001 | Danby et al. | |
| 6,263,230 B1 | 7/2001 | Haynor et al. | |
| 6,312,393 B1 | 11/2001 | Abreu | |
| 6,362,591 B1 | 3/2002 | Moberg | |
| 6,485,461 B1 | 11/2002 | Mason et al. | |
| 6,485,465 B2 | 11/2002 | Moberg et al. | |
| 6,555,986 B2 | 4/2003 | Moberg | |
| 6,568,922 B1 | 5/2003 | Winsel | |
| 6,582,393 B2 | 6/2003 | Sage, Jr. | |
| 6,589,229 B1 | 7/2003 | Connelly et al. | |
| 6,607,509 B2 | 8/2003 | Bobroff et al. | |
| 6,656,148 B2 | 12/2003 | Das et al. | |
| 6,659,980 B2 | 12/2003 | Moberg et al. | |
| 6,669,909 B2 | 12/2003 | Shvets et al. | |
| 6,692,457 B2 | 2/2004 | Flaherty | |
| 6,719,535 B2 | 4/2004 | Rakestraw et al. | |
| 6,739,478 B2 | 5/2004 | Bach et al. | |
| 6,740,059 B2 | 5/2004 | Flaherty | |
| 6,742,992 B2 | 6/2004 | Davis | |
| 6,830,562 B2 | 12/2004 | Mogensen et al. | |
| 6,929,619 B2 | 8/2005 | Fago et al. | |
| 6,942,636 B2 | 9/2005 | Holst et al. | |
| 7,145,330 B2 | 12/2006 | Xiao | |
| 7,193,521 B2 | 3/2007 | Moberg et al. | |
| 2001/0034502 A1 | 10/2001 | Moberg et al. | |
| 2001/0039398 A1 | 11/2001 | Fowler et al. | |
| 2002/0052574 A1 | 5/2002 | Hochman et al. | |
| 2002/0076825 A1 | 6/2002 | Cheng et al. | |
| 2002/0177237 A1 | 11/2002 | Shvets et al. | |
| 2003/0018304 A1 | 1/2003 | Sage | |
| 2003/0040700 A1 | 2/2003 | Hickle et al. | |
| 2003/0069369 A1 | 4/2003 | Belenkaya et al. | |
| 2003/0073954 A1 | 4/2003 | Moberg et al. | |
| 2003/0078534 A1 | 4/2003 | Hochman et al. | |
| 2003/0167035 A1 | 9/2003 | Flaherty et al. | |
| 2003/0212379 A1 | 11/2003 | Bylund et al. | |
| 2003/0213297 A1 | 11/2003 | Sage et al. | |
| 2003/0233069 A1 | 12/2003 | Gillespie et al. | |
| 2004/0013715 A1 | 1/2004 | Wnek et al. | |
| 2004/0019321 A1 | 1/2004 | Sage et al. | |
| 2004/0074768 A1 | 4/2004 | Anex et al. | |
| 2004/0074784 A1 | 4/2004 | Anex et al. | |
| 2004/0085215 A1 | 5/2004 | Moberg et al. | |
| 2004/0207396 A1 | 10/2004 | Xiao | |
| 2005/0051580 A1 | 3/2005 | Ramey | |
| 2005/0143864 A1 | 6/2005 | Blomquist | |
| 2005/0192494 A1 | 9/2005 | Ginsberg | |
| 2005/0214129 A1 | 9/2005 | Greene et al. | |
| 2005/0247558 A1 | 11/2005 | Anex et al. | |
| 2006/0047538 A1 | 3/2006 | Condurso et al. | |
| 2007/0062250 A1 * | 3/2007 | Krulevitch et al. | 73/1.16 |
| 2007/0066939 A1 * | 3/2007 | Krulevitch et al. | 604/152 |
| 2007/0093752 A1 * | 4/2007 | Zhao et al. | 604/131 |
| 2007/0093753 A1 * | 4/2007 | Krulevitch et al. | 604/131 |

OTHER PUBLICATIONS

Owner's Manual, Temposonics LK Embeddable Sensors, OEM Integrator's Manual, MTS Systems Corporation, Cary, NC 27513, 550562 Rev. B, Mar. 1998 (6 pgs).

International Search Report, from corresponding PCT/US06/36165, mailed Apr. 19, 2007.

Bratland, T. et al., "Linear Position Sensing Using Magnetoresistive Sensors," Honeywell Solid State Electronics Center (Apr. 8, 2005), entire document at http://web/20050408082814/http://www.ssec.Honeywell.com/magnetic/datasheets/linearpositionsensing.pdf.

International Search Report, from PCT/US06/36340, mailed Aug. 1, 2007.

International Search Report, from PCT/US06/36330, mailed Sep. 12, 2007.

International Search Report, from PCT/US06/36326, mailed Sep. 13, 2007.

International Search Report, from PCT/US06/36173, mailed Sep. 17, 2007.

* cited by examiner

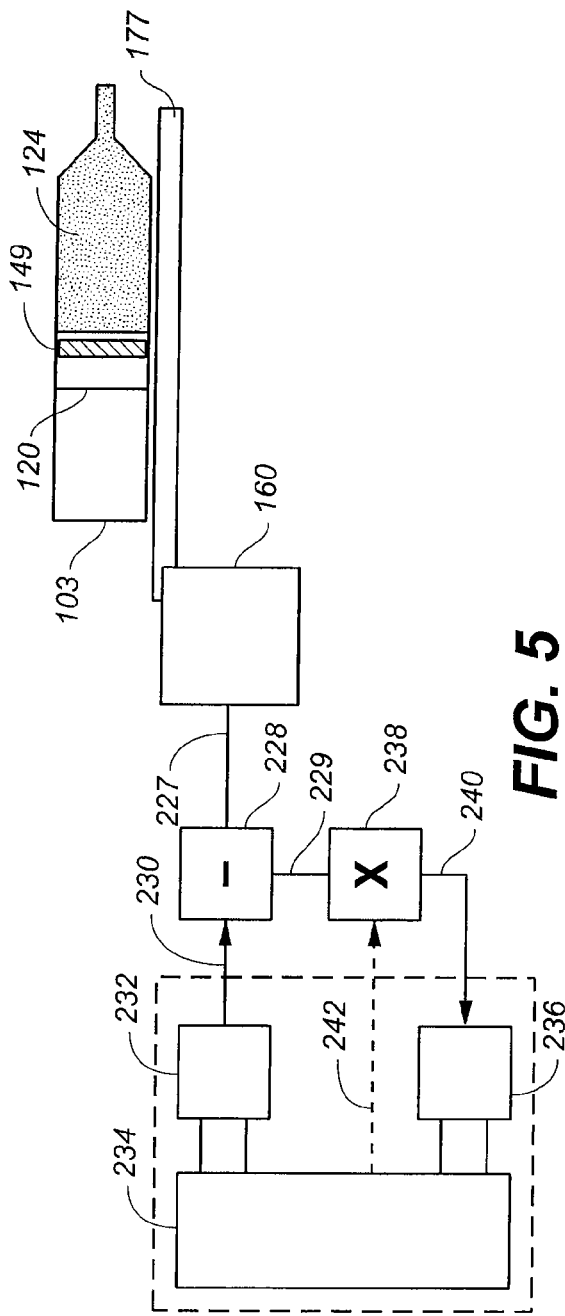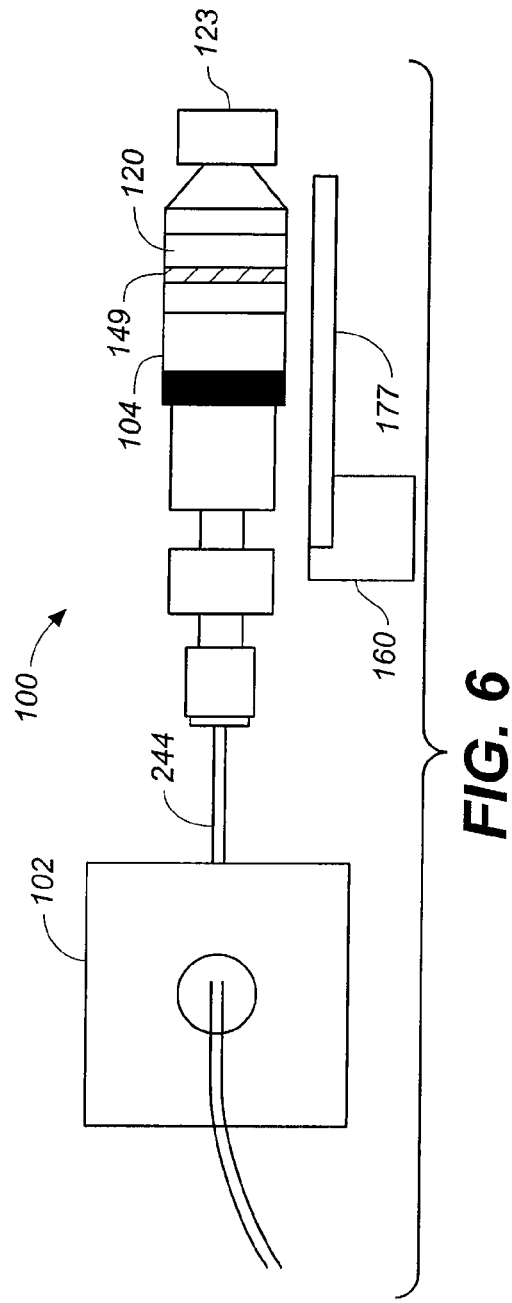

| Sensed Parameter | Current Draw Through Electrokinetic Porous Media | Decay of Current Draw Through Electrokinetic Porous Media | Open Circuit Potential Across Electrodes | Position of Moveable Partition |
|---|---|---|---|---|
| Occlusions | decreases | increases | increases | not as expected, typically moving less |
| Partial Occlusions | decreases | increases | increases | not as expected, typically moving less |
| Leaks in Infusion Sets | variable | decreases | decreases | not as expected, typically moving more |
| Leaks in Pump Seals | variable | decreases | decreases | not as expected, typically moving less |
| Leaks in Electrokinetic Porous Media | increases | increases | decreases | not as expected, typically moving less |
| Bubble Formation on Electrodes | increases | | increases | not as expected, typically moving more |
| Bubbles in Pump Chamber | variable | | increases | not as expected, continuing to move |
| Loss of Electrical Contact with Electrodes | will be zero | | not measurable | not as expected, typically moving less |
| Empty Electrokinetic Solution Supply Reservoir | decreases | | decreases | not as expected, typically moving less |
| Amount of Infusion Liquid Dispensed | used to estimate volume | | used to estimate volume | direct correlation to volume |
| Empty Infusion Liquid Reservoir | decreases or increases | | increases | not as expected, stops moving |
| Malfunctions in Electrokinetic Porous Media | not as expected | | not as expected | not as expected, typically moving less |

*FIG. 9*

MALFUNCTION DETECTION IN INFUSION PUMPS

FIELD OF THE INVENTION

The present invention is directed to malfunction detection in pumps, and more particularly to malfunction detection in electrokinetic mechanisms that can be indicative of malfunctions in an infusion pump.

BACKGROUND OF THE INVENTION

Traditional infusion pumps can incorporate sensors to detect malfunctions in the system, such as occlusions, low battery charge, or an empty infusion reservoir. Since traditional infusion pumps frequently use mechanical drive systems, such as DC motors, solenoids, and gears, they also tend to use electromechanical sensors, including pressure sensors, switches, force sensors, capacitive and piezoelectric-based pressure sensors, and strain gauges. Electro-mechanical sensors can be expensive, complex devices with many components. They can be unreliable, at times, and are not always sensitive. In many cases, the physical parameter being sensed by an electromechanical sensor is indirectly related to the failure mode being detected. For example, some traditional infusion pumps measure the torsion of a DC motor shaft, and must correlate shaft torsion with some other variable of interest. Unfortunately, other factors, such as gear friction and friction encountered by moveable partitions, can affect torsion, making it difficult to distinguish occlusion from normal frictional variations. For reasons such as these, it can be difficult to diagnose failure modes using electro-mechanical sensors, such as those used in traditional infusion pumps.

Accordingly, a need exists for new and/or improved methods and systems for detecting malfunctions in an infusion pump.

SUMMARY OF THE INVENTION

One exemplary embodiment is directed to a method for detecting a malfunction in an infusion pump. The infusion pump can operate to induce flow of an infusion fluid using electrokinetic phenomena, such as indirect pumping of an electrokinetic working fluid. Alternatively, the infusion pump can be driven by a non-electrokinetic source (e.g., mechanically driven) but can utilize an electrokinetic mechanism (e.g., sensor) to detect malfunctions. Some examples of malfunctions which can be detected include an occlusion, a leak, a depletion of electrokinetic working fluid, a depletion of infusion fluid, porous media malfunction, bubble formation on an electrode, the presence of a bubble in a pressurized portion of the pump, loss of electrical contact with an electrode in the pump, or any combination of malfunctions. A measurement of one or more electrokinetic properties of the pump can be obtained. For example, the measurement can be an electrode measurement between two sides of a porous media through which electrokinetic working fluid can flow, such as a current measurement or a voltage measurement. The electrode measurement can be indicative of a pressure difference measurement in the electrokinetic pump such as a difference between two regions (e.g., between two sides of a porous media, or between the infusion fluid region and a region holding electrokinetic working fluid). In general, a measurement can be compared with at least one sample value to determine whether the pump is malfunctioning. A sample value can include a value associated with an electrode measurement when the pump is functioning in a designated manner (e.g., within some desired operating range) and/or a previous electrode measurement taken from the electrokinetic infusion pump. If a malfunction has been found, a malfunction indication can be provided.

Another exemplary embodiment is directed to a method for detecting a malfunction in an electrokinetic infusion pump. The pump can be operated using one or more activate/de-activate cycles, where each cycle can comprise activating the pump for a first period of time and de-activating the pump for a second period of time. An electrode transient measurement (e.g., a current transient or voltage transient) can be obtained, which can be taken between two sides of a porous media through which electrokinetic working fluid can flow. An electrode transient measurement can correspond with one or more values that provide an indication of an electrode measured value over some time period. One example of an electrode transient measurement includes an open-circuit voltage transient measurement, which can be taken during one or more deactivate cycles or when no current flows between the electrodes. Alternatively, the measurement can include a current transient measurement, which can be taken during at least one activate portion of the activate/de-activate cycles. The measurement can be compared with one or more sample transients (e.g., a transient corresponding to designated or normal pump operation, or to one or more previously obtained measurements) to determine whether the electrokinetic infusion pump is malfunctioning. For instance, the presence of a malfunction can be indicated under conditions where a magnitude of the electrode transient measurement deviates from a magnitude of one or more sample transients.

In one example, a magnitude of a current transient, which can be characterized by a value indicative of a current rise during a designated portion or an entirety of a pump activate cycle, can be compared with a magnitude of a sample current transient, which can be characterized by a value indicative of some comparable current rise during an activate cycle. If the magnitude of the current transient exceeds the magnitude of the sample current transient (e.g., exceeds beyond a given tolerance value), a malfunction can be indicated such as indicating the presence of an occlusion. If the magnitude of the current transient is less than the magnitude of the sample current transient (e.g., less than a given tolerance value), a malfunction can be indicated such as indicating the presence of a leak.

Another exemplary embodiment is directed to a system for detecting malfunctions in an infusion fluid delivery apparatus. The system includes an infusion pump such as a pump that utilizes electrokinetic phenomena to drive infusion fluid flow. The system can also include an electrokinetic sensing device, which can optionally be independent of the mechanism that drives infusion fluid flow from the pump. The infusion pump can be coupled to electrodes (e.g., one or more capacitive electrodes) that can be configured to provide a measurement between opposite sides of a porous media. Examples of measurements include an open circuit voltage measurement and a current draw measurement. One or more of the electrodes can also be configured to apply a driving voltage to cause electrokinetic fluid to flow through the porous media, or can be a measurement electrode only. A processor can be coupled to the pump, which can be configured to provide an indication of pump malfunction. The indication can be based on one or more criteria such as a comparison between the measurement from the electrodes and one or more sample values. Specific types of comparisons that can be utilized include all the comparisons discussed herein with regard to the various methods of detecting a pump malfunction (e.g., comparing a measured current value with a sample current or a measured voltage transient with a sample voltage transient). Such comparisons can be indicative of specific types of malfunctions such as the presence of an occlusion or leak, a depletion of infusion fluid, a depletion of electrokinetic working fluid, a disconnect in an electrode lead, a malfunction in porous media, an anomalous (e.g., too high or too low) pressure reading, bubble formation on an electrode or in a fluid chamber, etc. An alert mechanism can be optionally coupled to the processor, in which case the processor can be configured to activate the mechanism if a pump malfunction is indicated. Such an alert mechanism can be further configured to provide some indication of a potential specific malfunction (e.g., presence of an occlusion).

Processors consistent with this embodiment can include at least one memory configured to store one or more sample values and the measurement (e.g., electrode transients that correspond to a sample voltage and an electrode voltage measurement, or a sample current and an electrode current measurement). In addition or alternatively, the processor can be configured to write one or more sample values to the memory based upon one or more measured values obtained from the electrodes. Processors can also be configured to operate the infusion pump using one or more activate/de-activate cycles, where each cycle includes activating the pump for a first time period and de-activating the pump for a second time period (the time periods optionally being subject to change for each cycle).

Other embodiments are directed to systems and methods of detecting malfunctions in electrokinetic pumps that utilize more than one type of measurement to provide a malfunction indication. Accordingly, embodiments can utilize two or more of current measurements, voltage measurements, moveable partition position, and other measurements to provide a more robust indication of the presence of a malfunction. Such embodiments can utilize a combination of comparison and indication steps, as disclosed in other embodiments described herein, to indicate the presence of a specific or general pump malfunction.

BRIEF DESCRIPTION OF THE SEVERAL VIEWS OF THE DRAWINGS

The present application will be more fully understood from the following detailed description taken in conjunction with the accompanying drawings (not necessarily to scale), in which:

FIG. 5 is a block diagram of a sensor signal processing circuit that can be used in an electrokinetic infusion pump with closed loop control according to an additional embodiment of the present invention, which includes a microprocessor, a digital to analog converter, an analog to digital converter, a voltage nulling device, a voltage amplifier, a position sensor control circuit, a magnetostrictive waveguide, and an electrokinetic infusion pump;

FIG. 6 is an illustration of an electrokinetic infusion pump with closed loop control according to an embodiment of the present invention, that includes an electrokinetic engine and infusion module, which was used to generate basal and bolus delivery of infusion liquid;

FIG. 9 presents a table that summarizes the use of various techniques to detect failure modes in an electrokinetic infusion pump, according to some embodiments of the present invention;

DETAILED DESCRIPTION OF EMBODIMENTS OF THE INVENTION

Figure 1A:
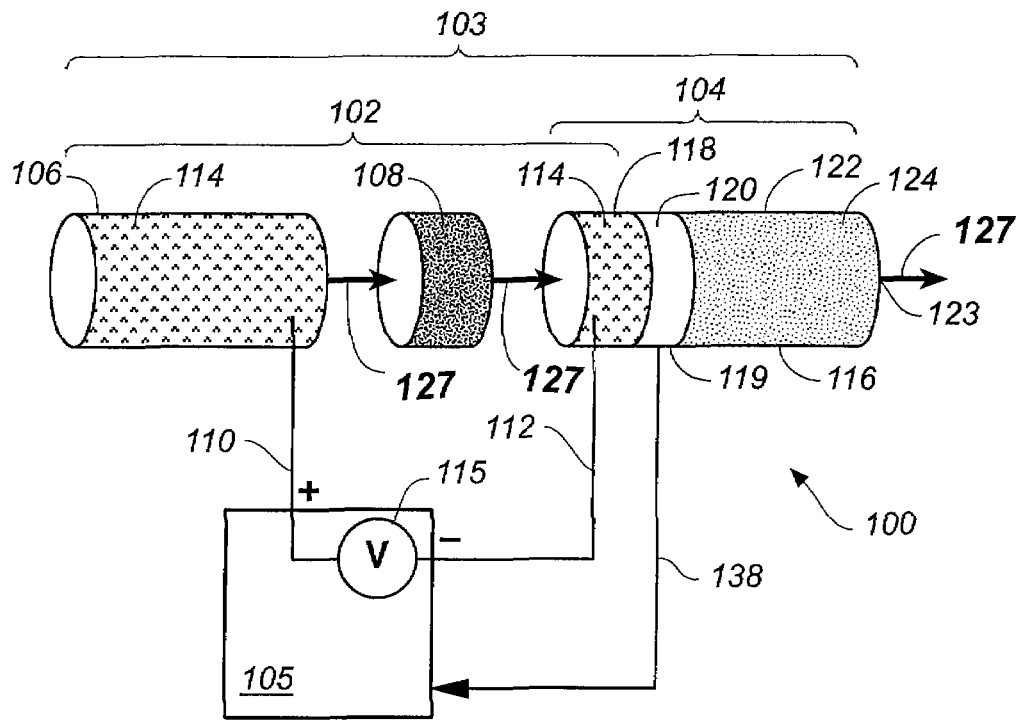
FIG. 1A is a schematic illustration of an electrokinetic pump in a first dispense position consistent with an embodiment of the invention, the pump including an electrokinetic engine, an infusion module, and a closed loop controller.

Certain exemplary embodiments will now be described to provide an overall understanding of the principles, structure, function, manufacture, and/or use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Electrokinetic Infusion Pumps

Electrokinetic infusion pumps can enable infusion systems with improved reliability, reduced size, and lower capital cost than traditional infusion pumps. One particular advantage of electrokinetic infusion pumps is that they have fewer mechanical parts, relying on electrokinetic pumping to generate pressure. Electrokinetic pumping (also known as electroosmotic flow) works by applying an electric potential across an electrokinetic porous media that is filled with electrokinetic solution. Ions in the electrokinetic solution form double layers in the pores of the electrokinetic porous media, countering charges on the surface of the electrokinetic porous media. Ions migrate in response to the electric potential, dragging the bulk electrokinetic solution with them. Electrokinetic pumping can be direct or indirect, depending upon the design. In direct pumping, infusion liquid is in direct contact with the electrokinetic porous media, and is in direct electrical contact with the electrical potential. In indirect pumping, infusion liquid is separated from the electrokinetic porous media and the electrokinetic solution by way of a moveable partition.

Further details regarding electrokinetic pumps, including materials, designs, and methods of manufacturing, suitable for use in devices according to the present invention are included in U.S. patent application Ser. Nos. 10/322,083, filed on Dec. 17, 2002, and Ser. No. 11/112,867, filed on Apr. 21, 2005, which are hereby incorporated by reference in their entirety. Other details regarding electrokinetic pumps can also be found in the copending U.S. patent application entitled "Electrokinetic Infusion Pump System," bearing Ser. No. 11/532,587, filed Sep. 18, 2006, which is hereby incorporated herein by reference in its entirety. Additional details regarding the manufacturing of portions of an electrokinetic pump can be found in a U.S. patent application entitled "Method for Preparing an Electrokinetic Element", and a U.S. patent application entitled "Method for Manufacturing an Electrokinetic Infusion Pump". Both of the previously mentioned applications are filed concurrently herewith, and are incorporated herein by reference in their entirety.

A variety of infusion liquids can be delivered with electrokinetic infusion pumps, including insulin for diabetes; morphine and/or other analgesics for pain; barbiturates and ketamine for anesthesia; anti-infective and antiviral therapies for AIDS; antibiotic therapies for preventing infection; bone marrow for immunodeficiency disorders, blood-borne malignancies, and solid tumors; chemotherapy for cancer; and dobutamine for congestive heart failure. The electrokinetic infusion pumps can also be used to deliver biopharmaceuticals. Biopharmaceuticals are difficult to administer orally due to poor stability in the gastrointestinal system and poor absorption. Biopharmaceuticals that can be delivered include monoclonal antibodies and vaccines for cancer, BNP-32 (Natrecor) for congestive heart failure, and VEGF-121 for preeclampsia. The electrokinetic infusion pumps can deliver infusion liquids to the patient in a number of ways, including subcutaneously, intravenously, or intraspinally. For example, the electrokinetic infusion pumps can deliver insulin subcutaneously as a treatment for diabetes, or can deliver stem cells and/or sirolimus to the adventitial layer in the heart via a catheter as a treatment for cardiovascular disease.

Figure 1B:
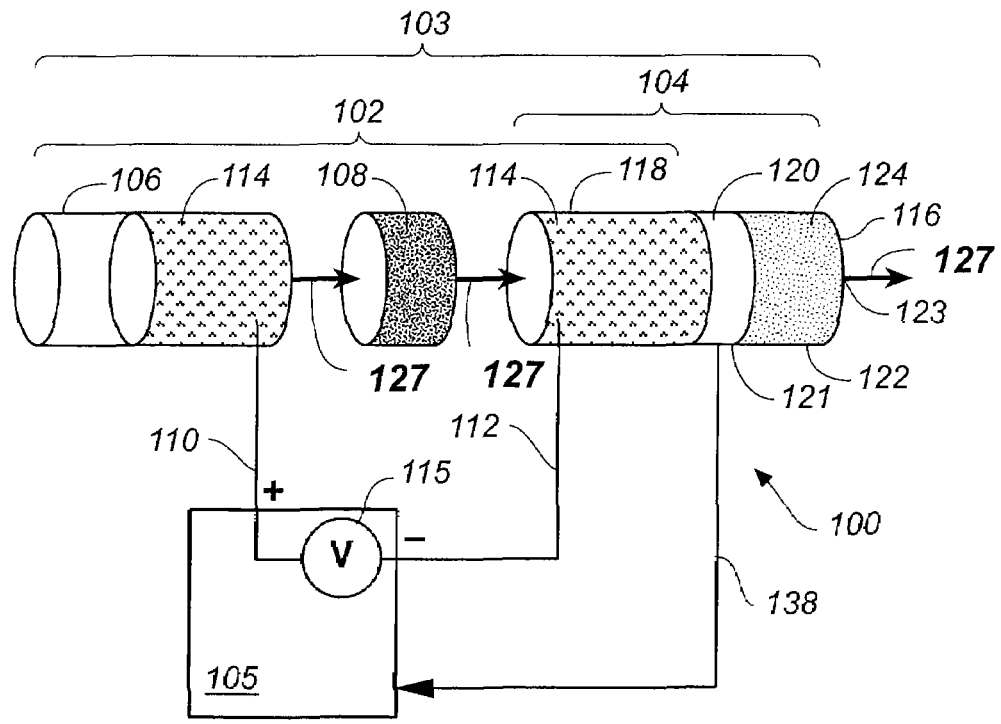
FIG. 1B is a schematic illustration of an electrokinetic pump of FIG. 1A in a second dispense position.

FIGS. 1A and 1B are schematic illustrations of an electrokinetic infusion pump with closed loop control 100 in accord with an exemplary embodiment. The electrokinetic infusion pump system illustrated in FIGS. 1A and 1B includes an electrokinetic infusion pump 103, and a closed loop controller 105. The electrokinetic infusion pump illustrated in FIG. 1A is in a first dispense position, while the pump illustrated in FIG. 1B is in a second dispense position. Electrokinetic infusion pump 103 includes electrokinetic engine 102 and infusion module 104. Electrokinetic engine 102 includes electrokinetic supply reservoir 106, electrokinetic porous media 108, electrokinetic solution receiving chamber 118, first electrode 110, second electrode 112, and electrokinetic solution 114. Closed loop controller 105 includes voltage source 115, and controls electrokinetic engine 102. Infusion module 104 includes infusion housing 116, electrokinetic solution receiving chamber 118, movable partition 120, infusion reservoir 122, infusion reservoir outlet 123, and infusion liquid 124. In operation, electrokinetic engine 102 provides the driving force for displacing infusion liquid 124 from infusion module 104. During fabrication, electrokinetic supply reservoir 106, electrokinetic porous media 108, and electrokinetic solution receiving chamber 118 are filled with electrokinetic solution 114. Before use, the majority of electrokinetic solution 114 is in electrokinetic supply reservoir 106, with a small amount in electrokinetic porous media 108 and electrokinetic solution receiving chamber 118. To displace infusion liquid 124, a voltage is established across electrokinetic porous media 108 by applying potential across first electrode 110 and second electrode 112. This causes electrokinetic pumping of electrokinetic solution 114 from electrokinetic supply reservoir 106, through electrokinetic porous media 108, and into electrokinetic solution receiving chamber 118. As electrokinetic solution receiving chamber 118 receives electrokinetic solution 114, pressure in electrokinetic solution receiving chamber 118 increases, forcing moveable partition 120 in the direction of arrows 127, i.e., the partition 120 is non-mechanically-driven. As moveable partition 120 moves in the direction of arrows 127, it forces infusion liquid 124 out of infusion reservoir outlet 123. Electrokinetic engine 102 continues to pump electrokinetic solution 114 until moveable partition 120 reaches the end nearest infusion reservoir outlet 123, displacing nearly all infusion liquid 124 from infusion reservoir 122.

Once again referring to the electrokinetic infusion pump with closed loop control 100 illustrated in FIGS. 1A and 1B, the rate of displacement of infusion liquid 124 from infusion reservoir 122 is directly proportional to the rate at which electrokinetic solution 114 is pumped from electrokinetic supply reservoir 106 to electrokinetic solution receiving chamber 118. The rate at which electrokinetic solution 114 is pumped from electrokinetic supply reservoir 106 to electrokinetic solution receiving chamber 118 is a function of the voltage and current applied across first electrode 110 and second electrode 112. It is also a function of the physical properties of electrokinetic porous media 108 and the physical properties of electrokinetic solution 114.

In FIG. 1A, movable partition 120 is in first position 119, while in FIG. 1B, movable partition 120 is in second position 121. The position of movable partition 120 can be determined, and used by closed loop controller 105 to control the voltage and current applied across first electrode 110 and second electrode 112. By controlling the voltage and current applied across first electrode 110 and second electrode 112, the rate at which electrokinetic solution 114 is pumped from electrokinetic supply reservoir 106 to electrokinetic solution receiving chamber 118 and the rate at which infusion liquid 124 is pumped through infusion reservoir outlet 123 can be controlled. A closed loop controller 105 can use the position of movable partition 120 to control the voltage and current applied to first electrode 110 and second electrode 112, and accordingly control infusion fluid delivered from the electrokinetic infusion pump.

Figure 2:
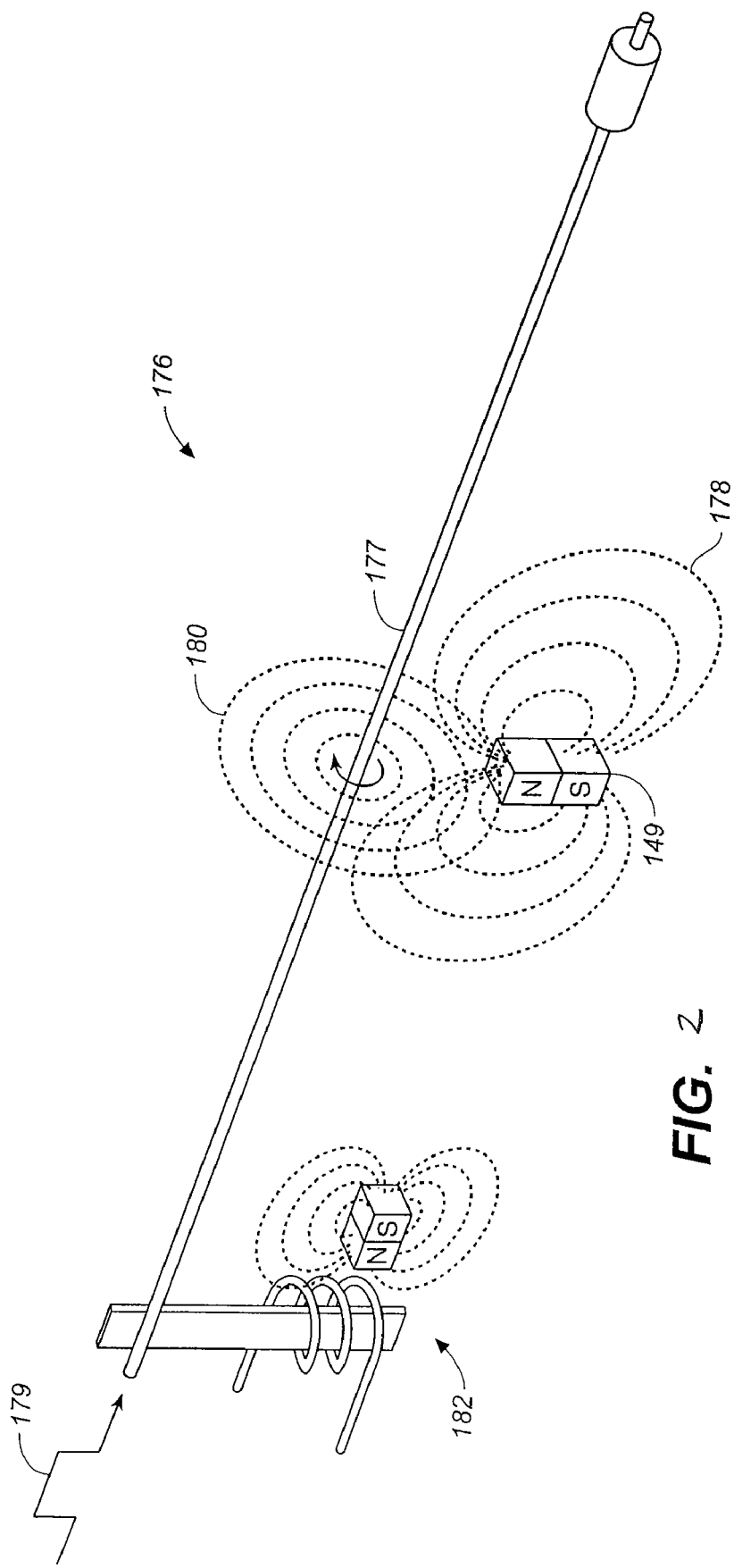
FIG. 2 is an illustration of a magnetic linear position detector as can be used in an electrokinetic infusion pump with closed loop control according to an embodiment of the present invention.

The position of movable partition 120 can be determined using a variety of techniques. In some embodiments, movable partition 120 can include a magnet, and a magnetic sensor can be used to determine its position. FIG. 2 illustrates the principles of one particular magnetic position sensor 176. Magnetic position sensor 176, suitable for use in this invention, can be purchased from MTS Systems Corporation, Sensors Division, of Cary, N.C. In magnetic position sensor 176, a sonic strain pulse is induced in magnetostrictive waveguide 177 by the momentary interaction of two magnetic fields. First magnetic field 178 is generated by movable permanent magnet 149 as it passes along the outside of magnetostrictive waveguide 177. Second magnetic field 180 is generated by current pulse 179 as it travels down magnetostrictive waveguide 177. The interaction of first magnetic field 178 and second magnetic field 180 creates a strain pulse. The strain pulse travels, at sonic speed, along magnetostrictive waveguide 177 until the strain pulse is detected by strain pulse detector 182. The position of movable permanent magnet 149 is determined by measuring the elapsed time between application of current pulse 179 and detection of the strain pulse at strain pulse detector 182. The elapsed time between application of current pulse 179 and arrival of the resulting strain pulse at strain pulse detector 182 can be correlated to the position of movable permanent magnet 149.

Other types of position detectors that include a magnetic sensor for identifying the position of a moveable partition also can be used, such as Hall-Effect sensors. In a particular example, anisotropic magnetic resistive sensors can be advantageously used with infusion pumps, as described in the copending U.S. patent applications entitled "Infusion Pumps with a Position Sensor," bearing Ser. No. 11/532,631, filed Sep. 18, 2006; and "Systems and Methods for Detecting a Partition Position in an Infusion Pump," bearing Ser. No. 11/532,653, filed Sep. 18, 2006; both of which are hereby incorporated by reference herein. In other embodiments, optical components can be used to determine the position of a movable partition. Light emitters and photodetectors can be placed adjacent to an infusion housing, and the position of the movable partition determined by measuring variations in detected light. In still other embodiments, a linear variable differential transformer (LVDT) can be used. In embodiments where an LVDT is used, the moveable partition includes an armature made of magnetic material. A LVDT that is suitable for use in the present application can be purchased from RDP Electrosense Inc., of Pottstown, Pa. Those skilled in the art will appreciate that other types of position detectors can also be utilized, consistent with embodiments of the present invention. For example, position detectors that utilize a capacitive displacement sensor can also be used with embodiments of the present invention. Use of such sensors is described in a U.S. patent application entitled "Infusion Pump with a Capacitive Displacement Sensor," which is concurrently filed with the present application. The entirety of the aforementioned application is incorporated herein by reference.

In alternative embodiments, the amount and/or rate that infusion fluid is dispensed from the pump can be obtained using an appropriate volumetric flow sensor. Suitable flow sensors include thermo-anemometer based sensors, differential pressure sensors, coriolis based mass flow sensors, and the like. Miniaturized sensors (e.g., Micro Electro Mechanical Sensors (MEMS)) are attractive due to their small size and potential low cost, which could allow integration into a dispensable design. When volumetric flow sensors are utilized, an infusion pump need not use a position detector to detect partition position, and subsequently relate that position to an amount of fluid dispensed. By obtaining a direct fluid amount measurement, such sensors can also be utilized to practice the embodiments of the invention discussed herein. For example, such sensors can provide a measured amount value corresponding with a discrete shot of fluid or the amount of fluid dispensed over a given time interval. Accordingly, the sensors can be used to practice techniques such as the closed loop control schemes or malfunction detection schemes discussed herein. All these potential variations are within the scope of the present application.

Figure 3:
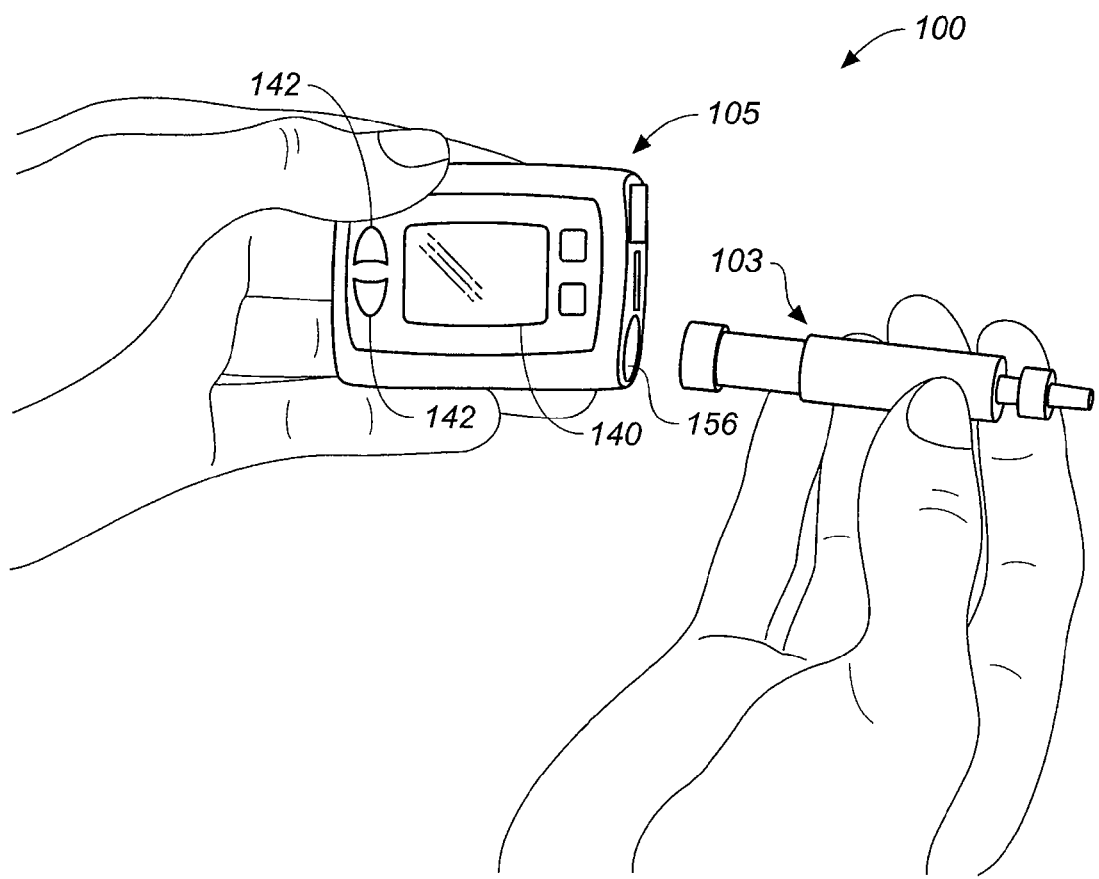
FIG. 3 is an illustration of an electrokinetic infusion pump with closed loop control according to an additional embodiment of the present invention.
Figure 4A:
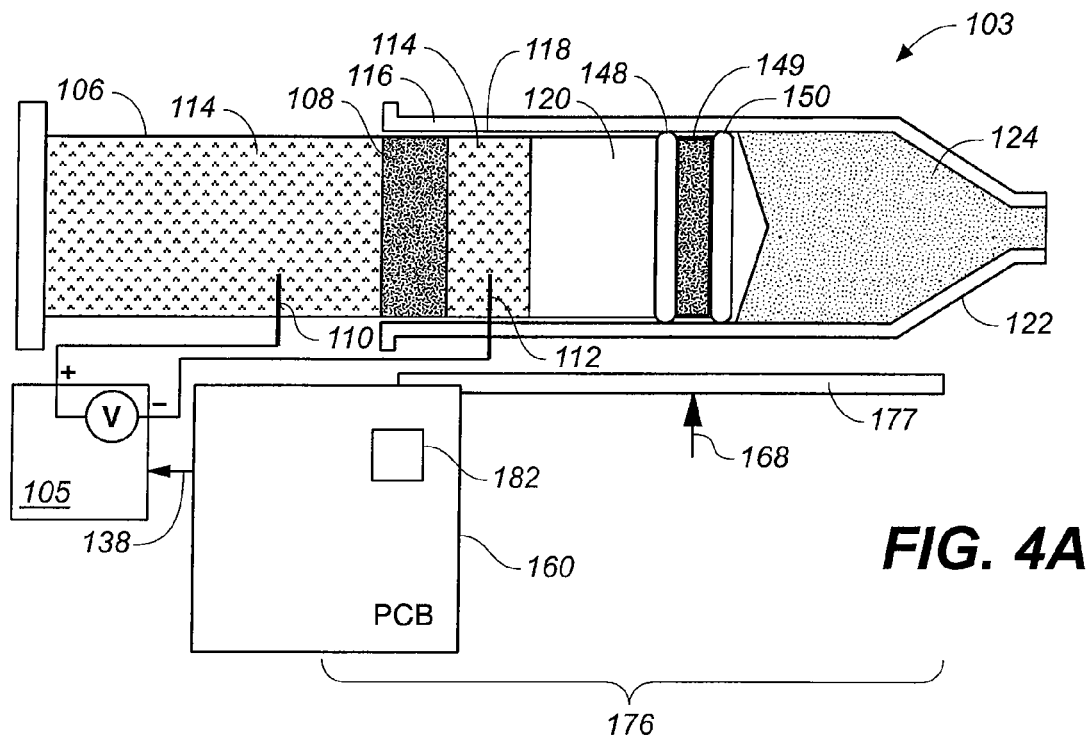
FIGS. 4A and 4B illustrate portions of an electrokinetic infusion pump with closed loop control according to an embodiment of the present invention, including an electrokinetic engine, an infusion module, a magnetostrictive waveguide, and a position sensor control circuit, the electrokinetic infusion pump illustrated in FIG. 4A is in a first dispense position, while the electrokinetic infusion pump illustrated in FIG. 4B is in a second dispense position.
Figure 4B:
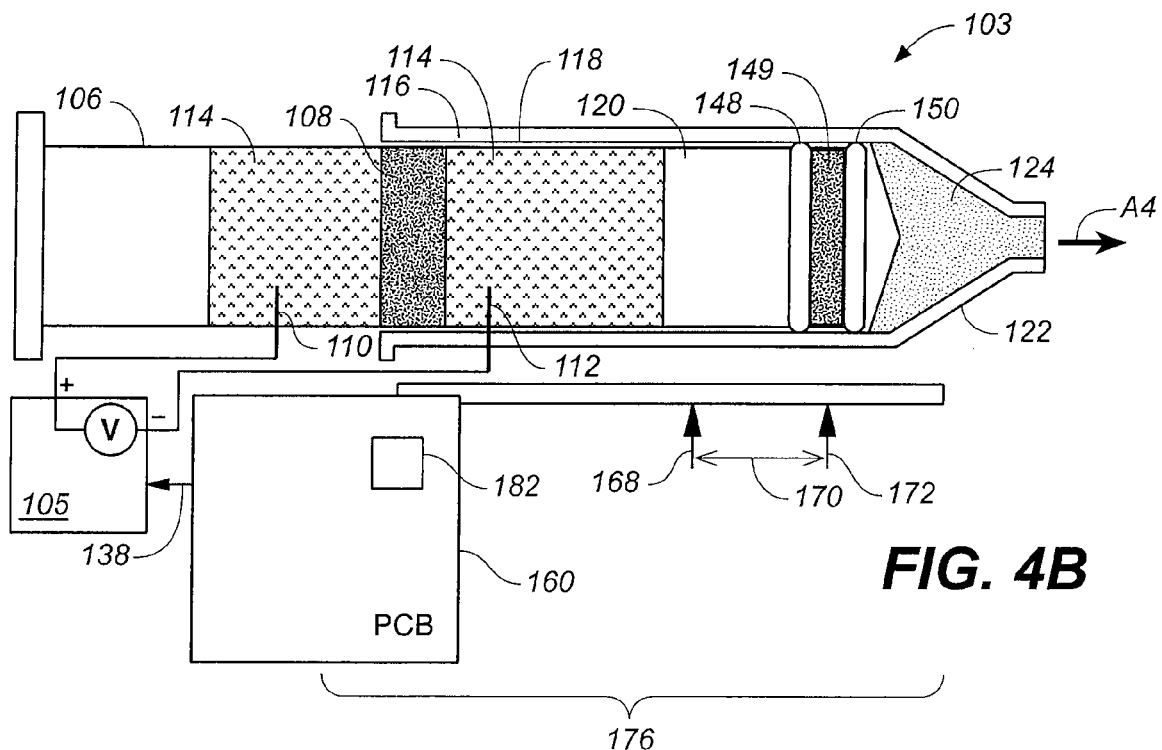

Depending upon desired end use, electrokinetic engine 102 and infusion module 104 can be integrated into a single assembly, or can be separate and connected by tubing. Electrokinetic engine 102 and infusion module 104 illustrated in FIGS. 3, 4A, and 4B are integrated, while electrokinetic engine 102 and infusion module 104 illustrated in FIG. 6 are not integrated. Regardless of whether electrokinetic engine 102 and infusion module 104 are integrated, the position of movable partition 120 can be measured, and used to control the voltage and current applied across electrokinetic porous media 108. In this way, electrokinetic solution 114 and infusion liquid 124 can be delivered as desired in either an integrated or separate configuration.

Electrokinetic supply reservoir 106, as used in the electrokinetic infusion pump with closed loop control illustrated in FIGS. 1A, 1B, 3, 4A, 4B, 5 and 6, can be collapsible, at least in part. This allows the size of electrokinetic supply reservoir 106 to decrease as electrokinetic solution 114 is removed. Electrokinetic supply reservoir 106 can be constructed using a collapsible sack, or can include a moveable piston with seals. Also, infusion housing 116, as used in electrokinetic infusion pump with closed loop control in FIGS. 1A, 1B, 3, 4A, 4B, 5, and 6, is preferably rigid, at least in part. This makes it easier to displace moveable partition 120 than to expand infusion housing 116 as electrokinetic solution receiving chamber 118 receives electrokinetic solution 114 pumped from electrokinetic supply reservoir 106, and can provide more precise delivery of infusion liquid 124. Moveable partition 120 can be designed to prevent migration of electrokinetic solution 114 into infusion liquid 124, while decreasing resistance to displacement as electrokinetic solution receiving chamber 118 receives electrokinetic solution 114 pumped from electrokinetic supply reservoir 106. In some embodiments, moveable partition 120 includes elastomeric seals that provide intimate yet movable contact between moveable partition 120 and infusion housing 116. In some embodiments, moveable partition 120 is piston-like, while in other embodiments moveable partition 120 is fabricated using membranes and/or bellows. As mentioned previously, closed loop control can help maintain consistent delivery of electrokinetic solution 114 and infusion liquid 124, in spite of variations in resistance caused by variations in the volume of electrokinetic supply reservoir 106, by variations in the diameter of infusion housing 116, and/or by variations in back pressure at the user's infusion site.

Closed Loop Control Schemes and Electrokinetic Pumps

Various exemplary embodiments are directed to methods and systems for controlling the delivery of infusion liquids from an electrokinetic infusion pump. In particular embodiments, a closed loop control scheme can be utilized to control delivery of the infusion liquid. Although many of the various closed loop control schemes described in the present application are described in the context of their use with electrokinetic engines, embodiments using other engines are also within the scope of embodiments of the present invention. Closed loop control, as described in the present application, can be useful in many types of infusion pumps. These include pumps that use engines or driving mechanisms that generate pressure pulses in a hydraulic medium in contact with the moveable partition in order to induce partition movement. These driving mechanisms can be based on gas generation, thermal expansion/contraction, and expanding gels and polymers, used alone or in combination with electrokinetic engines. As well, engines in infusion pumps that utilize a moveable partition to drive delivery of an infusion fluid (e.g., non-mechanically-driven partitions of an infusion pump such as hydraulically actuated partitions) can include the closed loop control schemes described herein.

Use of a closed loop control scheme with an electrokinetic infusion pump can compensate for variations that may cause inconsistent dispensing of infusion liquid. For example, with respect to FIGS. 1A and 1B, if flow of electrokinetic solution 114 varies as a function of the temperature of electrokinetic porous media 108, variations in the flow of infusion liquid 124 can occur if a constant voltage is applied across first electrode 110 and second electrode 112. By using closed loop control, the voltage across first electrode 110 and second electrode 112 can be varied based upon the position of moveable partition 120 and the desired flow of infusion liquid 124. Another example of using closed loop control involves compensating for variations in flow caused by variations in downstream resistance to flow. In cases where there is minimal resistance to flow, lower voltages and current may be used to achieve a desired flow of electrokinetic solution 114 and infusion liquid 124. In cases where there is higher resistance to flow, higher voltages and current may be used to achieve a desired flow of electrokinetic solution 114 and infusion liquid 124. Since resistance to flow is often unknown and/or changing, variations in flow of electrokinetic solution 114 and infusion liquid 124 may result. By determining the position of movable partition 120, the current and voltage can be adjusted to deliver a desired flow rate of electrokinetic solution 114 and infusion liquid 124, even if the resistance to flow is changing. Another example of using closed loop control involves compensating for variation in flow caused by variation in the force required to push movable partition 120. Variations in friction between movable partition 120 and the inside surface of infusion housing 116 may cause variations in the force required to push movable partition 120. If a constant voltage and current are applied across electrokinetic porous media 108, variation in flow of electrokinetic solution 114 and infusion liquid 124 may result. By monitoring the position of movable partition 120, and varying the voltage and current applied across electrokinetic porous media 108, a desired flow rate of electrokinetic solution 114 and infusion liquid 124 can be achieved. Accordingly, in some embodiments, a closed loop control algorithm can utilize a correction factor, as discussed herein, to alter operation of a pump (e.g., using the correction factor to change the current and/or voltage applied across the electrokinetic pump's electrodes).

Electrokinetic infusion pumps that utilize a closed loop control scheme can operate in a variety of manners. For example, the pump can be configured to deliver a fluid shot amount in a continuous manner (e.g., maintaining a constant flow rate) by maintaining one or more pump operational parameters at a constant value. Non-limiting examples include flow rate of infusion fluid or electrokinetic solution, pressure, voltage or current across electrodes, and power output from a power source. In such instances, a closed loop control scheme can be used to control the operational parameter at or near the desired value.

In some embodiments, the pump is configured to deliver an infusion fluid by delivering a plurality of fluid shot amounts. For example, the electrokinetic infusion pump can be configured to be activated to deliver a predetermined amount of fluid. The amount can be determined using a variety of criteria such as a selected quantity of fluid or application of a selected voltage and/or current across the electrodes of the pump for a selected period of time. Following activation, the pump can be deactivated for a selected period of time, or until some operating parameter reaches a selected value (e.g., pressure in a chamber of the electrokinetic pump). Continuous cycles of activation/deactivation can be repeated, with each cycle delivering one of the fluid shot amounts. An example of such operation is discussed herein. Closed loop control schemes can alter one or more of the parameters discussed with respect to an activation/deactivation cycle to control delivery of the infusion fluid. For instance, the shot duration of each shot can be altered such that a selected delivery rate of infusion fluid from the pump is achieved over a plurality of activation/deactivation cycles. Alteration of shot durations during activation/deactivation cycles can be utilized advantageously for the delivery of particular infusion fluids such as insulin. For example, diabetic patients typically receive insulin in two modes: a bolus mode where a relatively large amount of insulin can be dosed (e.g., just before a patient ingests a meal), and a basal mode where a relatively smaller, constant level of insulin is dosed to maintain nominal glucose levels in the patient. By utilizing activation/deactivation cycles, both delivery modes can easily be accommodated by simply adjusting the shot duration (e.g., very short shots during basal delivery and one or more longer shots for a bolus delivery) and/or the deactivation duration.

Another potential advantage to operating under repeated activation/deactivation cycles is that such an operation prevents too much infusion fluid from being released at once. Take, for example, an infusion pump operating at a constant delivery rate (i.e., not a continuous activation/deactivation cycle). If such an infusion pump becomes occluded, a closed loop controller could potentially continue to try and advance the plunger, causing the pressure to rise in the infusion set with little change in fluid delivery. Thus, if the occlusion is suddenly removed, the stored pressure could inject a potentially hazardous and even lethal dose of infusion fluid into the patient. Electrokinetic infusion pumps operating under a repeated cycle of activation and deactivation can reduce the risk of overdose by allowing the pressure stored within the infusion set to decrease over time due to leakage back through the electrokinetic porous material. Accordingly, some of the embodiments discussed herein utilize an infusion pump operating with an activation/deactivation cycle.

Another potential advantage of utilizing continuous activation/deactivation cycles is that such cycles can help an electrokinetic pump avoid potential mechanical inefficiencies. For example, with respect to insulin delivery in the basal mode, a very small pressure may be associated with infusing insulin at a slow rate. Very low pressures, however, may result in mechanical inefficiencies with pump movement. For example, smooth partition/piston movement may require a threshold pressure that exceeds the low pressure needed to infuse insulin at the designated basal rate, otherwise sporadic movement may result, leading to difficulties in pump control. By utilizing activation/deactivation cycles, a series of relatively small "microboluses" can be released, sufficiently spaced in time, to act as a virtual basal delivery. Each microbolus can use a high enough pressure to avoid the mechanical inefficiencies.

Some embodiments are directed to methods of controlling fluid delivery from an electrokinetic infusion pump. The electrokinetic infusion pump can be configured to deliver one or more fluid shot amounts. For example, the pump can deliver a single continuous fluid shot amount, consistent with continuous operation. Alternatively, a plurality of fluid shot amounts can be delivered as in a series of activation/deactivation cycles. One or more measured amounts can be determined for the plurality of shot amounts. For example, a measured amount can be obtained for each of a plurality of fluid shots, or after a selected number of fluid shots when a pump operates utilizing a series of activation/deactivation cycles. In another example, a series of measured amounts can be determined for a single continuous shot, corresponding to determining the amount of fluid displaced from the pump over a series of given time intervals during continuous fluid dispensing. Fluid shot amounts and measured amounts can be described by a variety of quantities that denote an amount of fluid. Though volume is utilized as a unit of shot amount in some embodiments, non-limiting other examples include mass, a length (e.g., with an assumption of some cross-sectional area), or a rate (e.g., volumetric flow rate, flux, etc.). An average measured amount can be calculated from the measured amounts, and subsequently used to calculate a correction factor. The correction factor can also depend upon an expected amount, which is either selected by a pump user or designated by a processor or controller of the pump. The correction factor can be used to adjust subsequent fluid delivery from the pump (e.g., used to adjust a subsequent fluid shot amount from the pump). Such subsequent fluid delivery can be used to correct for previous over-delivery or under-delivery of infusion fluid, or to deliver the expected amount.

During pump operation, as fluid is delivered, the steps of determining a measured amount; calculating an average measured amount; calculating a correction factor; and adjusting subsequent fluid delivery based at least in part on the correction factor, can be serially repeated (e.g., after each fluid shot, or after a selected plurality of fluid shots when using activation/deactivation cycles) to control dispensing of fluid from the pump. More details regarding various implementations of control loop schemes are presented in the copending U.S. patent application entitled "Infusion Pump with Closed Loop Control and Algorithm," bearing Ser. No. 11/532,598, filed Sep. 18, 2006, which is hereby incorporated herein by reference in its entirety.

Electrokinetic Infusion Pump with Closed Loop Controller

FIG. 3 is an illustration of an electrokinetic infusion pump with closed loop control 100 according to an exemplary embodiment of the present invention. Electrokinetic infusion pump with closed loop control 100 includes closed loop controller 105 and electrokinetic infusion pump 103. In the embodiments of electrokinetic infusion pump with closed loop control 100 illustrated in FIGS. 3, 4A, 4B, 5, and 6 electrokinetic infusion pump 103 and closed loop controller 105 can be handheld, or mounted to a user by way of clips, adhesives, or non-adhesive removable fasteners. Closed loop controller 105 can be directly or wirelessly connected to remote controllers that provide additional data processing and/or analyte monitoring capabilities. As outlined earlier, and referring to FIGS. 1A, 1B, and 3, closed loop controller 105 and electrokinetic infusion pump 103 can include elements that enable the position of movable partition 120 to be determined. Closed loop controller 105 includes display 140, input keys 142, and insertion port 156. After filling electrokinetic infusion pump 103 with infusion liquid 124, electrokinetic infusion pump 103 is inserted into insertion port 156. Upon insertion into insertion port 156, electrical contact is established between closed loop controller 105 and electrokinetic infusion pump 103. An infusion set is connected to the infusion reservoir outlet 123 after electrokinetic infusion pump 103 is inserted into insertion port 156, or before it is inserted into insertion port 156. Various means can be provided for priming of the infusion set, such as manual displacement of moveable partition 120 towards infusion reservoir outlet 123. After determining the position of moveable partition 120, voltage and current are applied across electrokinetic porous media 108, and infusion liquid 124 is dispensed. Electrokinetic infusion pump with closed loop control 100 can be worn on a user's belt providing an ambulatory infusion system. Display 140 can be used to display a variety of information, including infusion rates, error messages, and logbook information. Closed loop controller 105 can be designed to communicate with other equipment, such as analyte measuring equipment and computers, either wirelessly or by direct connection.

FIGS. 4A and 4B illustrate portions of an electrokinetic infusion pump with closed loop control according to an embodiment of the present invention. FIGS. 4A and 4B include electrokinetic infusion pump 103, closed loop controller 105, magnetic position sensor 176, and position sensor control circuit 160. Position sensor control circuit 160 is connected to closed loop controller 105 by way of feedback 138. Electrokinetic infusion pump 103 includes infusion housing 116, electrokinetic supply reservoir 106, electrokinetic porous media 108, electrokinetic solution receiving chamber 118, infusion reservoir 122, and moveable partition 120. Moveable partition 120 includes first infusion seal 148, second infusion seal 150, and moveable permanent magnet 149. Infusion reservoir 122 is formed between moveable partition 120 and the tapered end of infusion housing 116. Electrokinetic supply reservoir 106, electrokinetic porous media 108, and electrokinetic solution receiving chamber 118 contain electrokinetic solution 114, while infusion reservoir 122 contains infusion liquid 124. Voltage is controlled by closed loop controller 105, and is applied across first electrode 110 and second electrode 112. Magnetic position sensor 176 includes magnetostrictive waveguide 177, position sensor control circuit 160, and strain pulse detector 182. Magnetostrictive waveguide 177 and strain pulse detector 182 are typically mounted on position sensor control circuit 160.

In FIG. 4A, moveable partition 120 is in first position 168. Position sensor control circuit 160 sends a current pulse down magnetostrictive waveguide 177, and by interaction of the magnetic field created by the current pulse with the magnetic field created by moveable permanent magnet 149, a strain pulse is generated and detected by strain pulse detector 182. First position 168 can be derived from the time between initiating the current pulse and detecting the strain pulse. In FIG. 4B, electrokinetic solution 114 has been pumped from electrokinetic supply reservoir 106 to electrokinetic solution receiving chamber 118, pushing moveable partition 120 toward second position 172. Position sensor control circuit 160 sends a current pulse down magnetostrictive waveguide 177, and by interaction of the magnetic field created by the current pulse with the magnetic field created by moveable permanent magnet 149, a strain pulse is generated and detected by strain pulse detector 182. Second position 172 can be derived from the time between initiating the current pulse and detecting the strain pulse. Change in position 170 can be determined using the difference between first position 168 and second position 172. As mentioned previously, the position of moveable partition 120 can be used in controlling flow in electrokinetic infusion pump 103.

Figure 7:
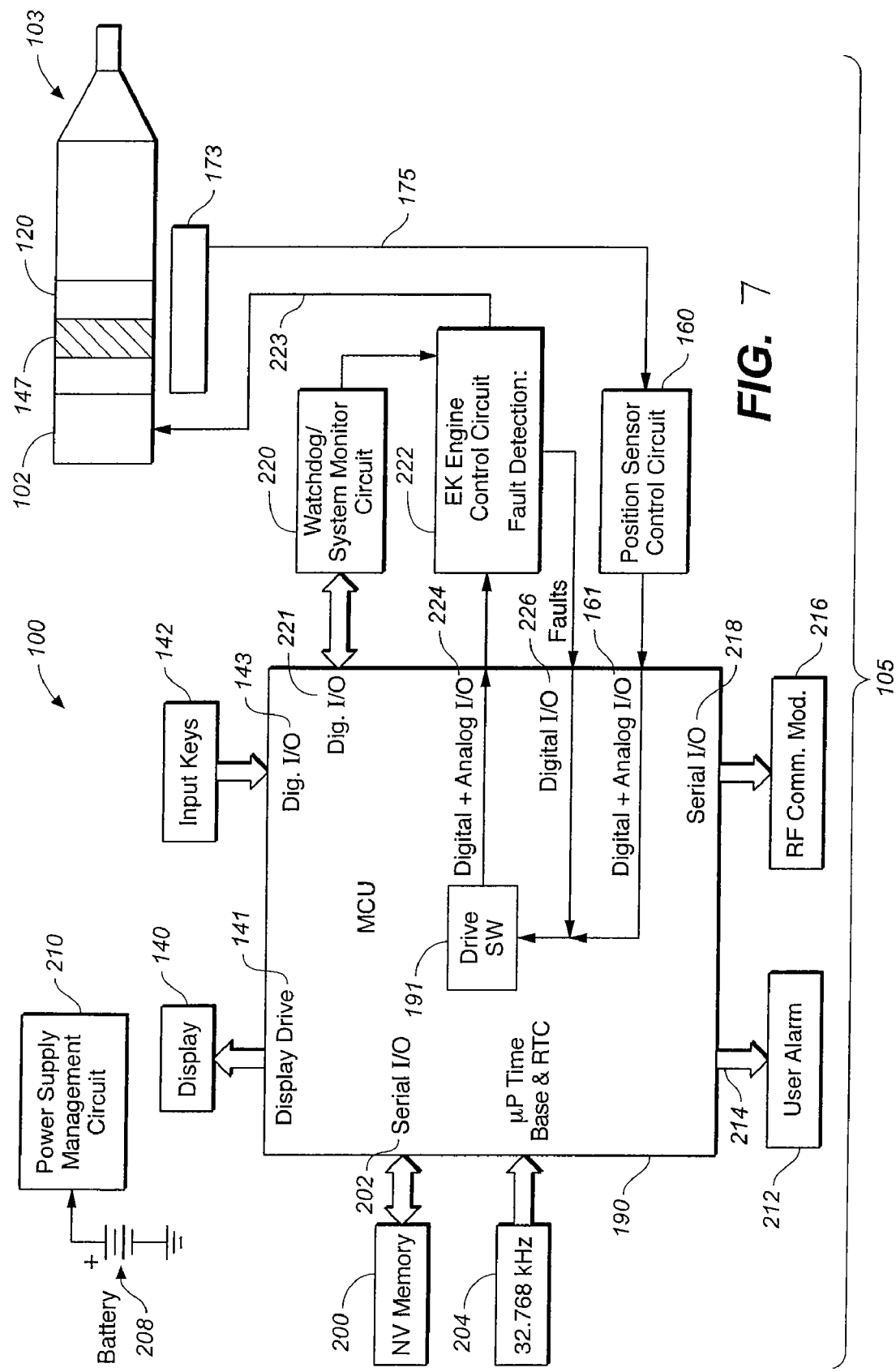
FIG. 7 is a block diagram of a sensor signal processing circuit that can be used in an electrokinetic infusion pump with closed loop control according to an additional embodiment of the present invention, which includes a microprocessor, a digital to analog converter, an analog to digital converter, a voltage nulling device, a voltage amplifier, a position sensor control circuit, a magnetostrictive waveguide, and an electrokinetic infusion pump.

FIG. 7 is a block diagram of a circuit that can be used as part of a controller in an electrokinetic infusion pump with closed loop control according to an additional embodiment of the present invention. Electrokinetic infusion pump 103 includes electrokinetic engine 102, and moveable partition 120. Electrokinetic engine 102 displaces moveable partition 120 by pumping electrokinetic solution 114 (not shown) against moveable partition 120. Moveable partition 120 includes moveable permanent magnet 149. The position of moveable permanent magnet 149 in electrokinetic infusion pump 103 is detected by magnetostrictive waveguide 177. Although in this illustration magnetic techniques are used to determine the position of moveable partition 120, other types of position sensors that emit a signal identifying a position of a moveable partition can also be used, as mentioned previously. Other techniques include the use of light emitters, photodetectors, anisotropic magnetic resistive sensors, and capacitive sensors. Electrokinetic infusion pump with closed loop control 100 includes master control unit 190 and master control software 191. Master control unit 190 and master control software 191 control various elements in electrokinetic infusion pump with closed loop control 100, including display 140, input keys 142, non-volatile memory 200, system clock 204, user alarm 212, radio frequency communication circuit 216, position sensor control circuit 160, electrokinetic engine control circuit 222, and system monitor circuit 220. Battery 208 powers master control unit 190, and is controlled by power supply and management circuit 210. User alarm 212 can be audible, vibrational, or optical.

Master control unit 190 can be mounted to a printed circuit board and includes a microprocessor. Master control software 191 controls the master control unit 190. Display 140 provides visual feedback to users, and is typically a liquid crystal display, or its equivalent. Display driver 141 controls display 140, and is an element of master control unit 190. Input keys 142 allow the user to enter commands into closed loop controller 105 and master control unit 190, and are connected to master control unit 190 by way of digital input and outputs 143. Non-volatile memory 200 provides memory for closed loop controller 105, and is connected to master control unit 190 by way of serial input and output 202. System clock 204 provides a microprocessor time base and real time clock for master control unit 190. User alarm 212 provides feedback to the user, and can be used to generate alarms, warnings, and prompts. Radio frequency communication circuit 216 is connected to master control unit 190 by way of serial input and output 218, and can be used to communicate with other equipment such as self monitoring blood glucose meters, electronic log books, personal digital assistants, cell phones, and other electronic equipment. Information that can be transmitted via radio frequency, or with other wireless methods, include pump status, alarm conditions, command verification, position sensor status, and remaining power supply. Position sensor control circuit 160 is connected to master control unit 190 by way of digital and analog input and output 161, and is connected to magnetostrictive waveguide 177 by way of connector 175. As discussed previously, position sensor control circuit 160 uses magnetostrictive waveguide 177 and moveable permanent magnet 149 to determine the position of moveable partition 120. Electrokinetic engine control circuit 222 is connected to master control unit 190 by way of digital and analog input and output 224, and to electrokinetic engine 102 by way of connector 223. Electrokinetic engine control circuit 222 controls pumping of electrokinetic solution 114 and infusion liquid 124, as mentioned previously. Electrokinetic engine control circuit 222 relies upon input from position sensor control circuit 160, and commands issued by master control unit 190 and master control software 191, via digital and analog input and output 224. Fault detection in electrokinetic engine control circuit 222 is reported to master control unit 190 and master control software 191 by way of digital input and output 226. System monitor circuit 220 routinely checks for system faults, and reports status to master control unit 190 and master control software 191 by way of digital input and output 221. Battery 208 provides power to master control unit 190 and is controlled by power supply and management circuit 210.

Embodiments of the invention can utilize a closed loop controller configured to control delivery of a fluid shot amount from the electrokinetic infusion pump. In the particular embodiment shown in FIG. 7, the master control software 191 can be programmed to control fluid release from the electrokinetic infusion pump 103. In particular, a controller can be configured to implement any of the closed loop control schemes disclosed within the present application. Accordingly, a controller can be configured to control delivery of a fluid shot amount from an infusion pump based at least in part upon an expected amount and an average measured amount calculated from a plurality of previously measured amounts. Such measured amounts can be obtained from a position detector (e.g., a magnetic position sensor). The controller (e.g., the software and processor) can also be configured to calculate the average measured amount using any of the methods described herein, for example a weighted average that more heavily weights recently obtained measured amounts. All possible variations of the features of closed loop control schemes disclosed herein can be implemented in such a controller. Those skilled in the art will appreciate that implementation of a controller need not follow the exact embodiment shown in FIG. 7. Indeed, hardwire circuitry can include embedded software, which can be configured to carry one or more or all of the instructions necessary to implement a particular closed loop control scheme. Furthermore, one or more separate processors or separate hardware control units can be combined as a "controller" consistent with embodiments of the invention described herein. As well, a "controller" can include memory units that are read-only or capable of being overwritten to hold parameters such as selected values or control parameters (e.g., the number of measured amounts used in an averaging calculation, an expected amount, a fractional value of the deviation used in a correction factor, etc.). All these variations, and others, are within the scope of the disclosure of the present application.

FIG. 5 is a block diagram of a position sensor signal processing circuit that can be used in an electrokinetic infusion pump with closed loop control according to an additional embodiment of the present invention. The block diagram illustrated in FIG. 5 includes electrokinetic infusion pump 103, magnetostrictive waveguide 177, position sensor control circuit 160, voltage nulling device 228, voltage amplifier 238, digital to analog converter 232, analog to digital converter 236, and microprocessor 234. Electrokinetic infusion pump 103 includes moveable partition 120 and infusion liquid 124. Moveable partition 120 includes moveable permanent magnet 149, which interacts with magnetostrictive waveguide 177 in determining the position of moveable partition 120 in electrokinetic infusion pump 103. When the position sensor signal processing circuit illustrated in FIG. 5 is used, the resolution of magnetostrictive waveguide 177 is increased. In operation, magnetostrictive waveguide 177 yields a voltage that varies as a function of the position of moveable permanent magnet 149. When the position sensor signal processing circuit illustrated in FIG. 5 is not used, the voltage from magnetostrictive waveguide 177 ranges from 0 to a maximum value that is determined by analog to digital converter 236. For a given resolution of the analog to digital converter, the resolution of magnetostrictive waveguide 177 is determined by the maximum voltage that analog to digital converter 236 can process divided by the length of magnetostrictive waveguide 177.

When the position sensor signal processing circuit illustrated in FIG. 5 is used, voltage nulling device 228 can offset the voltage from magnetostrictive waveguide 177 to either zero, or a value near zero. After the voltage from magnetostrictive waveguide 177 is offset by voltage nulling device 228, nulled voltage 229 can be multiplied using voltage amplifier 238 to a value less than the maximum voltage that can be processed by analog to digital converter 236. The combined effect of nulling device 228 and voltage amplifier 238 is to divide the maximum voltage that can be processed by analog to digital converter 236 by a smaller length, and in that way increase the voltage change per unit length of movement by moveable permanent magnet 149. To avoid exceeding the capacity of analog to digital converter 236, the nulling step can be repeated by voltage nulling device 228 multiple times as moveable partition 120 moves along the length of electrokinetic infusion pump 103. Larger voltage change per unit length of movement by moveable permanent magnet 149 allows smaller detectable volumes, and more sensitive determination of the position of moveable permanent magnet 149, for a given resolution of the analog to digital converter 236. Upon insertion of electrokinetic infusion pump 103 into closed loop controller 105, an amplification factor of approximately 1 can be used by voltage amplifier 238, with a nulling voltage of 0 volts. Once moveable permanent magnet 149 moves from its original position, voltage nulling device 228 can apply nulling voltage that results in a nulled voltage of approximately zero, and voltage amplifier 238 can amplify the voltage, while keeping the voltage in the range of analog to digital converter 236. If power to closed loop controller 105 is inadvertently lost, the nulling voltage and amplification factor can be recovered from non-volatile memory 200, if it has been previously stored. In alternative embodiments, a fixed amplification factor can be used, and the nulling voltage varied to keep the voltage within the range of analog to digital converter 236.

As mentioned previously, when designing an electrokinetic infusion pump with closed loop control 100, the infusion module 104 and the electrokinetic engine 102 can be integrated, as illustrated in FIGS. 3, 4A, 4B, and 5, or they can be separate components connected with tubing, as illustrated in FIG. 6. In FIG. 6, electrokinetic infusion pump with closed loop control 100 includes infusion module 104 and electrokinetic engine 102, connected by connection tubing 244. Infusion module 104 includes moveable partition 120 and infusion reservoir outlet 123. Moveable partition 120 includes moveable permanent magnet 149. Further details regarding electrokinetic engine 102, including materials, designs, and methods of manufacturing, suitable for use in electrokinetic infusion pump with closed loop control 100 are included in U.S. patent application Ser. No. 10/322,083, previously incorporated by reference.

Malfunction Detection in Infusion Pumps

Accurate monitoring of infusion liquid delivery can be of utmost importance in particular applications. Errors, such as in the delivered quantity of infusion liquid, can be caused by a variety of types of pump malfunctions. The term "malfunction" as used herein is meant to be broadly interpreted to include all types of conditions where a system or device functions abnormally or away from some typical designed protocol. Accordingly, as used herein, the term "malfunction" need not refer to a total breakdown or inoperability in a system, but rather simply refers to any condition that deviates from some defined or designed mode. For example, with respect to an infusion pump, one type of malfunction is an occlusion in the infusion line between the infusion reservoir outlet and the infusion site on the user. Common causes for occlusion include kinks in infusion line tubing, or blockage of the sub-dermal infusion tip. While one result of an occlusion can be insufficient delivery of infusion liquid, another result of an occlusion can be a build up of pressure in infusion liquid, infusion reservoir, electrokinetic solution, and electrokinetic solution receiving chamber. Excess pressure can cause excess delivery of infusion liquid 124 in the event that an occlusion is suddenly removed. For this reason, among others, it is desirable to detect occlusions as early as possible. Leakages are another example of a malfunction. Leakages can include failures in an infusion set, seals, or an infusion reservoir, which result in a loss of infusion fluid. Leakages can also be with respect to the electrokinetic working fluid, which is the result of malfunctions such as a rupture or loss of sealing in porous media, or a working fluid reservoir, etc. Other exemplary malfunctions include bubble formation and existence in various areas of the pump, loss of electrical connectivity in an infusion pump, empty reservoirs of infusion fluid or electrokinetic working fluid, and anomalous behavior in electrokinetic porous media. Indeed, it should be understood that the malfunction detection schemes discussed herein are not necessarily limited to detecting the explicitly described malfunctions discussed herein.

Accordingly, some embodiments of the present application are directed to methods and systems for detecting a malfunction in an infusion pump. For instance, such embodiments can be used to detect malfunctions such as the presence of an occlusion or fluid-leak in an infusion pump. In some examples, the presence of bubbles, other obstructions that interfere with flow from an infusion pump, or an infusion pump disconnect can be detected in a pump. One way to detect malfunctions is by using various means to determine the position of movable partition as a function of time. When a moveable partition does not move as expected, an indication of such can also be reported, e.g., by activating an alarm status. In other embodiments, additional measurements can be used to detect malfunctions, including measuring the potential across electrodes during pump off time, the current draw through electrokinetic porous media during pump on time, the decay of potential across electrodes during pump off time, and the decay of current draw through electrokinetic porous media during pump on time. One potential advantage of using the latter measurements is that no additional mechanical measuring components are required. Measurements can be made by making slight changes to existing pump circuitry in the case of an electrokinetic infusion pump. Though individual measurements (e.g., current, voltage, partition position, etc.) can be used to detect malfunctions, other embodiments will utilize any combination of the individual measurements discussed herein to provide malfunction detection. For example, partition position detection can be combined with open circuit voltage monitoring to provide a more robust error detection scheme. All potential combinations of the various disclosed malfunction detection schemes are within the scope of the present application, though some specific combinations are discussed herein.

It should be noted that many embodiments discussed herein are directed to malfunction detection methods and devices for an infusion pump that is driven by flow of an electrokinetic fluid, such as by and indirect pumping action as described herein with FIGS. 1A and 1B. However, the embodiments can also be applied to infusion pumps which utilize a drive-mechanism that does not rely on electrokinetic flow to induce infusion fluid flow. Accordingly, one skilled in the art will appreciate that slight modifications to the described embodiments can allow the malfunction detection schemes that are applied to electrokinetically-driven infusion fluid flow to be applied to pumps that do not utilize such a mechanism. This is discussed further herein.

Many of the malfunction detection schemes discussed herein include the use of a closed loop controller. Such a controller, which can be used to monitor one or more parameters such as partition position, open circuit voltage drop, and/or current flowing through electrodes, can be used in conjunction with any appropriate malfunction detection scheme to aid detection of malfunctions in an infusion pump. Those skilled in the art will appreciate that a variety of closed loop control schemes or controllers can be implemented to provide malfunction detection (e.g., occlusions and fluid-leaks) within the scope of the present application's disclosure. It is understood, however, that many of the malfunction detection schemes disclosed herein, though described in the context of using a closed loop controller, can also operate in an infusion pump without closed loop control (e.g., simply utilizing an appropriately configured processor).

In some embodiments, position sensing is used to detect malfunctions in the operation of an infusion pump. When a moveable partition, e.g., a non-mechanically driven partition used to drive infusion fluid movement, does not move in an expected manner, detection of such unexpected partition movement can be linked to an infusion pump malfunction, generally indicating the anomalous partition movement, or more specifically with one or more specific causes (e.g., occlusions, leaks, etc.).

Figure 8:
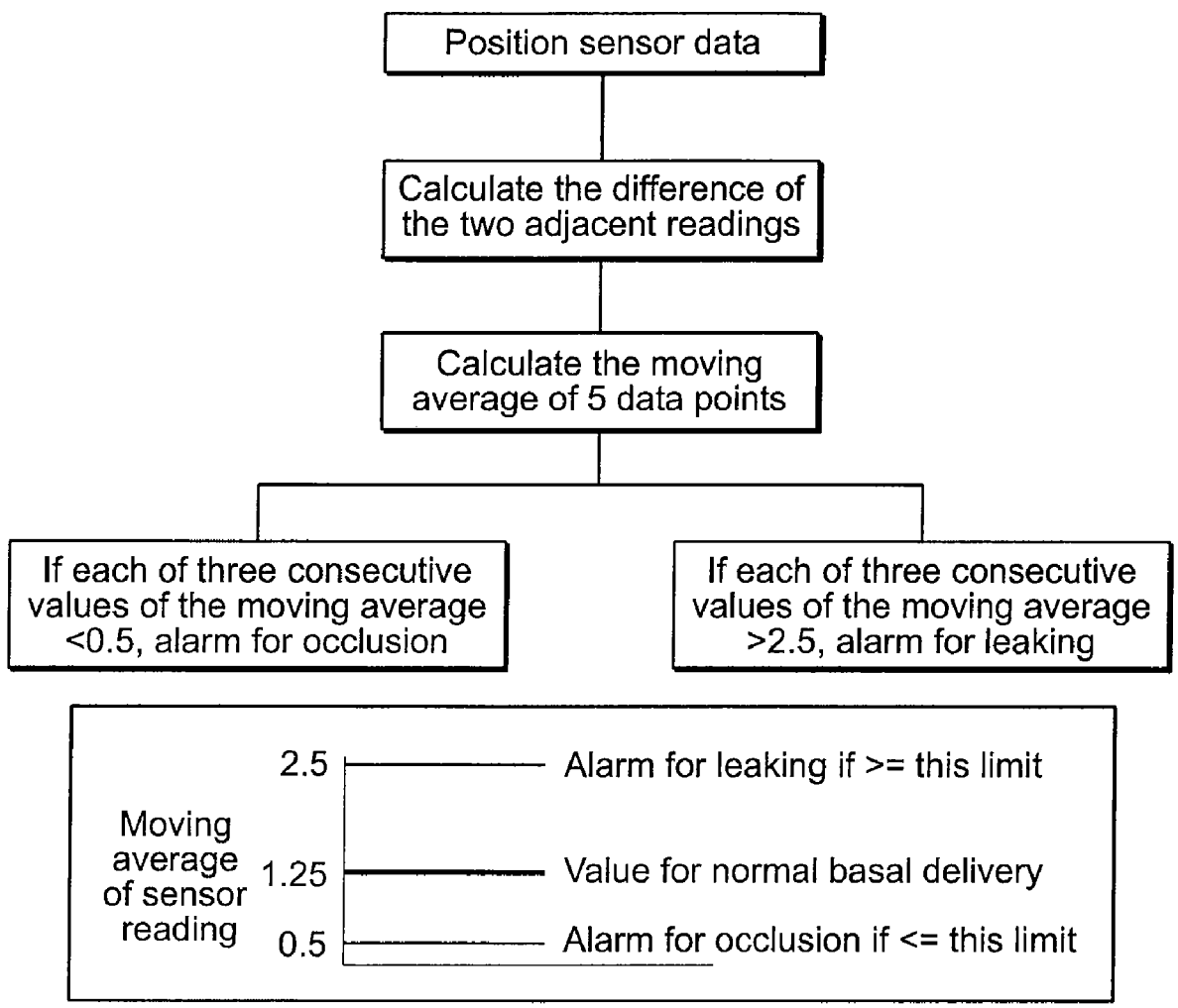
FIG. 8 is a flow chart of an algorithm that can be used to detect occlusions and leaks, according to an embodiment of the present invention.

In using the position of a movable partition to detect occlusions and leaks, an algorithm, such as that illustrated in FIG. 8, can be used, consistent with some embodiments of the invention. In the first step of the algorithm, the position of the movable partition can be detected. Any of the techniques described herein can be used to determine the position of the movable partition. In the next step of the algorithm, the difference can be calculated between the current and previous position of the movable partition. Next, this difference can be averaged with the difference calculated for the previous five measurements. A comparison can be made subsequently. If the average difference in position is less than some designated value (e.g., about 0.5 sensor units), an occlusion indication can be reported or activated. If the average difference in position is more than some designated value (e.g., about 2.5 sensor units), a leakage alarm can be reported or activated. If the average difference in position is between the two designated values (e.g., between about 0.5 and about 2.5 sensor units), a normal status can be reported or activated. Using the algorithm illustrated in FIG. 8, occlusions have been detected in less than 5 microliters of infusion liquid that was not dispensed, and leaks have been detected in less than 2.5 microliters of infusion liquid.

Use of position sensing to detect malfunctions such as occlusions or leaks, which can optionally include the use of closed loop control, is described in more detail in the copending U.S. patent applications entitled "Malfunction Detection via Pressure Pulsation," bearing Ser. No. 11/532,726, filed Sep. 18, 2006; and "Malfunction Detection with Derivative Calculation," bearing Ser. No. 11/532,691, filed Sep. 18, 2006, which are hereby incorporated herein by reference in their entirety.

According to embodiments of the present invention, other algorithms can also be envisioned for error detection, including occlusion and leak detection, based on open circuit potential across a first electrode and a second electrode, and/or decay in current draw across an electrokinetic porous media. These algorithms can be used in both basal and bolus delivery mode across a wide range of flow rates. In developing algorithms, response of the parameters discussed can be determined over a wide range of flow rates, and limits can be set as a function of flow rates. Algorithms can include the use of position sensing algorithms, in conjunction with algorithms, similar and different, that utilize other parameters.

Other embodiments of the invention are also directed to methods and systems for detecting a malfunction in an electrokinetic infusion pump, such as occlusions or leaks. In particular, such embodiments can utilize sensing methods other than those based on electro-mechanical means to monitor the status and/or detect malfunctions in an electrokinetic infusion pump. For instance, an embodiment can detect one or more parameters related to aspects of electrokinetic phenomena that are indicative of pump operation. By comparing the measured parameter(s) with at least one sample value, i.e., the value of a comparable sample parameter, an indication can be provided as to whether the pump is malfunctioning. Non-limiting examples of parameters to be measured can include measurements of the potential across a first electrode and a second electrode during pump off time, measurements of current draw through electrokinetic porous media during pump on time, measurements of the decay of potential across a first electrode and a second electrode during pump off time, measurements of the decay of current draw through electrokinetic porous media during pump on time, the monitoring of streaming or open circuit potential during pump off time, and others including further examples within the present application. These sensing mechanisms can be implemented without adding too much complexity and cost to an electrokinetic infusion pump since they utilize elements already incorporated in an electrokinetic infusion pump. Another advantage is that these sensing methods detect physical properties that directly correlate with particular failure modes.

The one or more sample values, which can be used for comparison against one or more measured values, can be indicative of some expected operational condition of the pump. Thus, when the comparison deviates from the expected condition, a malfunction can be indicated. For example, a sample value can be representative of a "normally" functioning infusion pump, e.g., a pump operating within some specified design manner. Thus, one or more sample values can correspond with voltage values or current values, which are expected when an electrokinetic mechanism is operating as designed. In another example, one or more sample values can correspond with one or more previously measured values of the pump. Accordingly, the comparison between a measured value and a sample value can be indicative of when the pump operates in a manner that deviates from a previous operating manner.

A variety of different types of sample values can be utilized with embodiments of the present invention. For instance, a sample value can be a particular current or voltage value associated with an expected pump operating condition. Examples include a sample current value when a pump operates in a continuous mode, or a sample voltage value measured at some designated moment when a pump is deactivated. The particular values can also correspond with an average value taken from a series of previous measurements (e.g., a moving average taken from the last N measurements).

Sample values, beyond corresponding to a designated operating/measured value, can alternatively correspond to a sample transient, i.e., one or more values which can represent the change in a sample parameter over a designated time period. Accordingly, a sample transient can be represented by a plurality of values distributed over the designated time period, or a single value indicative of the change in a sample parameter over the designated time period (e.g., a current difference value between a current corresponding to when an activate cycle begins and a current corresponding to a set time period after the activate cycle begins). Of course, measured transients can be utilized that are similarly defined.

Thus, in some embodiments, malfunction detection of an electrokinetic infusion pump can be performed by comparing a transient measurement with a sample transient. For example, the transients can be associated with a current or voltage transient indicative of the parameter behavior during an activation or de-activation portion of an activate/de-activate cycle, respectively. A transient measurement of a parameter for a pump working intermittently can act differently than an expected trend of the parameter when the pump acts in a continuous manner in some circumstances. For instance, when an electrokinetic pump works in a continuous mode, the presence of an occlusion will tend to slow flow of infusion fluid, which ultimately results in a decrease in observed current flow due to a corresponding decrease in electrokinetic fluid flow through porous media. Correspondingly, leaks of infusion fluid can result in an increase in observed current readings. However, if an electrokinetic pump works using activate/de-activate cycles, it has been observed that the magnitude of the current rise and decay increase when an occlusion is present (though the average current decreases). Decay of current draw through electrokinetic porous media can increase significantly, with initial current draw drifting higher, final current draw drifting lower, and the difference between initial and final current draw increasing. The magnitude of the current amplitude can decrease when a leak is present. The experiments disclosed herein provide some data to illustrate these points.

It is understood that when one or more measured values are compared with one or more sample values, such comparisons can be made in a variety of manners, all within the scope of embodiments of the present invention. For example, the comparison can be a ratio of the measured versus the sample, wherein the ratio can be outside a designated range to be indicative of a malfunction. In another example, the comparison can be made by calculating a difference between the measured and the sample. When the difference is greater than some tolerance value, then a positive indication of a malfunction can be provided. Other comparison techniques can also be utilized such as comparing average values of measurements and samples. Clearly, practice of the disclosed embodiments is not necessarily limited by the particular comparison techniques explicitly discussed herein.

An illustration of a situation which utilizes some aspects of these embodiments is described herein. An electrokinetic infusion pump can be operated intermittently (e.g., activate/deactivate mode). That is, there is pump on time (i.e., the pump is activated), and pump off time (i.e., the pump is deactivated), resulting in basal or bolus delivery of infusion liquid. Higher flow rates of infusion liquid can be obtained by modulating the pump on time, the pump off time, and the voltage across first electrode 110 and second electrode 112, as depicted in FIGS. 1A and 1B. When delivering infusion liquid 124 with an electrokinetic infusion pump, a relationship exists between the pressure inside infusion reservoir 122 and the pressure inside electrokinetic solution receiving chamber 118. For example, if the pressure in infusion reservoir 122 increases, as a result of an occlusion in the infusion reservoir outlet or the infusion tip for instance, then the pressure in electrokinetic solution receiving chamber 118 also increases. Therefore, an occlusion in the infusion reservoir outlet or the infusion tip can be detected by the monitoring the pressure in electrokinetic solution receiving chamber 118. Accordingly, some embodiments of the present invention can include monitoring the pressure in an electrokinetic solution receiving chamber to detect malfunctions such as occlusions, leaks or other errors, as discussed herein. It is understood, however, that these embodiments can also provide an indication of the pressure in an infusion fluid conduit such as some location in the infusion set or within the infusion reservoir 122. Indeed, the relationship between the pressure in the electrokinetic solution receiving chamber and the infusion fluid pressure can allow one to exchange the use of one pressure for another in the embodiments disclosed herein.

With reference to exemplary FIGS. 1A and 1B, when no potential is applied across first electrode 110 and second electrode 112, i.e., the pump off time or time during which the pump is deactivated, electrokinetic solution 114 will flow through electrokinetic porous media 108 from electrokinetic solution receiving chamber 118 to electrokinetic supply reservoir 106 if the pressure of electrokinetic solution 114 in electrokinetic solution receiving chamber 118 is greater than the pressure of electrokinetic solution 114 in electrokinetic supply reservoir 106. During operation of the electrokinetic infusion pump, the pressure of the electrokinetic solution 114 in electrokinetic supply reservoir 106 is typically near atmospheric pressure. When a potential is applied across first electrode 110 and second electrode 112, i.e., the pump on time or time when the pump is activated, the pressure of electrokinetic solution 114 in electrokinetic solution receiving chamber 118 increases, pushing movable partition 120 forward and expelling infusion liquid 124 from infusion reservoir 122, eventually reducing the pressure of electrokinetic solution 114 in electrokinetic solution receiving chamber 118.

When an occlusion occurs, movable partition 120 is hindered from expelling infusion liquid 124 from infusion reservoir 122, and the pressure of electrokinetic solution 114 in electrokinetic solution receiving chamber 118 builds up during each pump on cycle. During pump off time, electrokinetic solution 114 flows from electrokinetic solution receiving chamber 118, through electrokinetic porous media 108, and into electrokinetic supply reservoir 106 until the pressure of electrokinetic solution 114 in electrokinetic solution receiving chamber 118 and electrokinetic supply reservoir 106 are nearly equal.

Due to its physical and chemical properties, as outlined in U.S. patent application Ser. No. 10/322,083 filed on Dec. 17, 2002 and U.S. patent application Ser. No. 11/112,867 filed on Apr. 21, 2005 which have been previously incorporated by reference, a voltage is generated across an electrokinetic porous media when electrokinetic solution is flows through the porous media. This phenomena is known as streaming potential, and can be interpreted in some ways as the opposite of electrokinetic pumping or electroosmotic flow, as described previously. A mathematical relationship involving the streaming potential, $\Delta V$, and the difference in pressure $\Delta P$ between electrokinetic solution 114 in electrokinetic solution receiving chamber 118 and electrokinetic solution 114 in electrokinetic supply reservoir 106, as shown in FIGS. 1A and 1B, is established by the Helmholtz-Schmoluchowsky equation:

$$\Delta V = \frac{\varepsilon \zeta}{\eta \sigma} \Delta P \qquad \text{Equation 1}$$

where $\varepsilon$ is the permittivity of electrokinetic solution, $\eta$ is the viscosity of electrokinetic solution, $\sigma$ is the electrical conductivity of electrokinetic solution, and $\zeta$ is the zeta potential of electrokinetic porous media.

As can be seen in Equation 1, streaming potential, $\Delta V$, is directly proportional to the difference in pressure $\Delta P$ between electrokinetic solution 114 in electrokinetic solution receiving chamber 118 and electrokinetic solution 114 in electrokinetic supply reservoir 106, as shown in FIGS. 1A and 1B. The difference in pressure $\Delta P$ is a function of the pore size of electrokinetic porous media 108. At a fixed flow rate, the difference in pressure $\Delta P$ will increase as the pore size of electrokinetic porous media 108 decreases, and the difference in pressure $\Delta P$ will decrease as the pore size of electrokinetic porous media 108 increases. Since streaming potential, $\Delta V$, is directly proportional to the difference in pressure $\Delta P$ streaming potential, $\Delta V$, increases as the pore size of electrokinetic porous media 108 decreases, and streaming potential, $\Delta V$, decreases as the pore size of electrokinetic porous media 108 increases.

In some embodiments, the pressure of electrokinetic solution in reservoir electrokinetic solution receiving chamber can be determined during pump off time by measuring the streaming potential across a first electrode and a second electrode caused by flow of electrokinetic solution through electrokinetic porous media. If an occlusion occurs, consecutive activations of an electrokinetic infusion pump during basal or bolus delivery of infusion liquid can result in a build up of a pressure in the electrokinetic solution receiving chamber, with less dissipation of pressure during pump off time than expected when no occlusion is present. The build up of pressure in electrokinetic solution receiving chamber can be monitored by measuring the streaming potential across first electrode and second electrode during pump off time. If the pressure buildup in electrokinetic solution receiving chamber exceeds a preset level, an alarm status can be activated.

In some embodiments, streaming potential is measured across electrodes, which can be used to induce electrokinetic pumping. In these embodiments the potential across a first electrode and a second electrode during pump off time is also referred to as open circuit potential. It is understood, however, that open circuit potential can generally refer to a measurement in the electrokinetic device when a driving voltage is not being applied. To measure streaming potential, or open circuit potential, during pump off time, the first electrode and the second electrode can be switched from applying a voltage to becoming part of a voltage measuring circuit. Depending upon the type of electrode used for pumping, in other embodiments of the present invention it can be beneficial to use separate electrodes placed in an electrokinetic solution receiving chamber and an electrokinetic supply reservoir for measurement of streaming potential, and/or open circuit potential. In those embodiments, silver/silver chloride or platinum electrodes can be used, and can optionally be screen-printed in the form of an electrode patch.

In addition to monitoring streaming or open circuit potential, other embodiments of the present invention can monitor current draw through an electrokinetic porous media during pump on time. As exemplified in FIGS. 1A and 1B, the current draw through electrokinetic porous media 108 during pump on time is proportional to the amount of electrokinetic solution 114 that is pumped through electrokinetic porous media 108, and to the current required to build charge on first electrode 110 and second electrode 112 when a potential is applied across first electrode 110 and second electrode 112. An expected current draw through electrokinetic porous media 108 can be associated with a typically operating infusion pump (e.g., an infusion pump delivering infusion fluid in a designed manner), and deviation from expected current draw can be used to detect malfunctions in the electrokinetic infusion pump. Current draw through electrokinetic porous media 108 can be monitored during pump on time, while voltage is applied across first electrode 110 and second electrode 112, and an alarm status can be reported if current draw is other than expected. Current draw through electrokinetic porous media 108 can be measured using first electrode 110 and second electrode 112, or can be measured with a separate set of electrodes designed specifically for current measurement. In other embodiments of the present invention, either first electrode 110 or second electrode 112 can be used with at least one other electrode designed specifically for current measurements.

In some embodiments, the amount of infusion liquid dispensed from an electrokinetic infusion pump can be estimated using the voltage across first electrode and second electrode and/or the current draw through electrokinetic porous media. With reference to exemplary FIGS. 1A and 1B, the amount of infusion liquid 124 dispensed from electrokinetic infusion pump 100, as estimated using current draw through electrokinetic porous media 108, can be used to determine if an electrokinetic infusion pump, and/or its associated closed loop controller, is functioning properly. The amount of infusion liquid 124 dispensed from electrokinetic infusion pump 100, as estimated using current draw through electrokinetic porous media 108, can also be combined with estimates based on the position of movable partition 120, and/or the streaming potential or open circuit potential across electrokinetic porous media 108, as mentioned previously. An alarm state can be activated if discrepancies between the various estimates are observed.

With non-capacitive electrode materials, oxidation or reduction of compounds in electrokinetic solution occurs on the surface of the electrodes when a potential is applied. With reference to exemplary FIGS. 1A and 1B, current draw through the electrokinetic porous media 108 can be measured, with the current decaying according to the Cottrell equation. The Cottrell equation can be derived from Faraday's law and Fick's first law. The Cottrell equation relates charge, Q, between first electrode 110 and second electrode 112 to the concentration of compounds, $E_c$, in electrokinetic solution 114 that are oxidized or reduced.

For capacitive electrode materials as used in some embodiments of the present invention, and with reference to exemplary FIGS. 1A and 1B, Equations 2 and 3 can relate the capacitance of first electrode 110 and second electrode 112, $C_d$, the resistance of electrokinetic solution 114, $R_s$, the voltage applied across first electrode 110 and second electrode 112, V, the current draw through electrokinetic porous media 108, i, the voltage across the electrodes first electrode 110 and second electrode 112, $V_c$, and the voltage across electrokinetic solution 114, $V_R$.

$$Q = C_d E_c \qquad \text{Equation 2}$$

$$V = V_R + 2V_c = iR_s + 2Q/C_d \qquad \text{Equation 3}$$

Equation 4 relates the current draw, it, through electrokinetic porous media 108 at pump on time, t, and the voltage applied across first electrode 110 and second electrode 112.

$$i_t = (Ve^{-2t/R_sC_d})/R_s \qquad \text{Equation 4}$$

As can be seen in Equation 4, the current draw through electrokinetic porous media 108, i, is an exponential function of pump on time, t. Also, the natural log of the current draw through electrokinetic porous media 108, i, is linear in respect to pump on time, t.

As mentioned previously, in some embodiments of the present invention, an additional electrode can be used for measurements of current and/or potential. An additional electrode can be in the form of metal wire, or can be screen-printed conductive ink, in order to reduce the cost of the device.

In some exemplary embodiments of the present invention, the pressure in electrokinetic solution receiving chamber can increase, after an occlusion in infusion reservoir outlet, by approximately 0.2 pounds per square inch (psi) per cycle when delivering infusion liquid at a basal rate of about 0.15 microliters/min., by approximately 0.5 psi per cycle when delivering infusion liquid at a basal rate of about 0.5 microliters/min., and by approximately 5.8 psi per cycle when delivering infusion liquid at a basal rate of about 5.83 microliters/min. As mentioned previously, a cycle is defined as one period of pump on time, followed by one period of pump off time. In this embodiment, when delivering infusion liquid at a basal rate of about 0.15 microliters/min; pump on time is approximately 5 seconds, pump off time is approximately 180 seconds, and one cycle takes approximately 185 seconds. When delivering infusion liquid at a basal rate of about 0.5 microliters/min, pump on time is approximately 5 seconds, pump off time is approximately 55 seconds, and one cycle takes approximately 60 seconds. When delivering infusion liquid at a basal rate of about 5.83 microliters/min; pump on time is approximately 25 seconds, pump off time is approximately 35 seconds, and one cycle takes approximately 60 seconds.

In some other exemplary embodiments of the present invention, decay of current draw through the electrokinetic porous media increases after an occlusion in infusion reservoir outlet by approximately 0.4 microamps per cycle when delivering infusion liquid at a basal rate of about 0.15 microliters/min; by approximately 0.8 microamps per cycle when delivering infusion liquid at a basal rate of about 0.5 microliters/min; and by approximately 3 microamps per cycle when delivering infusion liquid at a basal rate of about 5.83 microliters/min. Thus, pressure in the electrokinetic solution receiving chamber and/or the current draw through the electrokinetic porous media as a function of time may be used as an indicator of occlusions in an electrokinetic infusion pump.

As alluded to earlier, monitoring current draw through the electrokinetic porous media and the magnitude of decay of current draw through electrokinetic porous media can also be used to detect leaks in infusion reservoir outlet, infusion reservoir, or electrokinetic solution receiving chamber. Consistent with an embodiment of the invention, and as illustrated in examples herein, a correlation can be established between leaks in electrokinetic solution receiving chamber, leaks in infusion reservoir, leaks in infusion reservoir outlet, current draw through electrokinetic porous media, and magnitude of decay of current draw through electrokinetic porous media.

Streaming and open circuit potential as a function of time can also be used to detect leaks. As pressure decreases in the electrokinetic solution receiving chamber, as a result of a leak, backflow through electrokinetic porous media during pump off time decreases. Since streaming potential is proportional to backflow through electrokinetic porous media, it has been observed that streaming potential decreases suddenly when leaks occurs. These phenomena can be used to detect leakage in electrokinetic infusion pumps, according to some embodiments of the present invention.

Without necessarily being bound by any particular theory, it is believed that voltage and current transients, which can be indicative of malfunctions in electrokinetic infusion pumps (e.g., leaks and occlusions), can act in accord with the following equations. With reference to FIGS. 1A and 1B, when capacitive electrodes are used for first electrode 110 and second electrode 112, the magnitude of decay of current draw through electrokinetic porous media 108 follows Equation 4 during pump on time:

$$i_t = (Ve^{-2t/RsCd})/R_s \qquad \text{Equation 4}$$

where:
V=applied voltage (Volts)
$R_s$=solution resistance (ohms)
$C_d$=capacity of the carbon electrode (Farads)
$i_t$=the current draw at the time t (secs)

As a result of the relationship outlined in Equation 4, the magnitude of decay of current draw through electrokinetic porous media 108 can be expressed by Equation 5.

$$\Delta i = i_{t=0} - i_t = (V/R_s)*(1-e^{-2t/RsCd}) \qquad \text{Equation 5}$$

Since the values of $R_s$ and $C_d$ are large (Rs is on the order of megaohms, and Cd is on the order of Farads), current decay is typically slow, and Δi is relatively small. In some electrokinetic pump systems, a larger current decay can be observed, which can be due to ion depletion in the porous media during the power on phase, and thus an increase in the pump resistance.

When the infusion line or a cannula is occluded, the pressure in electrokinetic solution receiving chamber 118 is proportional to V, the potential applied across first electrode 110 and second electrode 112, and is expressed by Equation 6.

$$V = a^2 P/(32\zeta\epsilon) \qquad \text{Equation 6}$$

Where,
a=pore size of the membrane
ζ=zeta potential of the membrane
ε=permittivity By combining Equations 5 and 6, current decay, Δi, can be related to pressure in electrokinetic solution receiving chamber 118 after occlusion, as expressed in Equation 7

$$\Delta i = i_{t=0} - i_t = (V/R_s)*(1-e^{-2t/RsCd}) = a^2 P/(32R_s\zeta\epsilon)*(1-e^{-2t/RsCd}) \qquad \text{Equation 7}$$

Because of the system compliance and back leakage of electrokinetic fluid from the receiving chamber to the electrokinetic fluid reservoir, the pressure increase will be slower in the presence of an occlusion. Thus, Δi will increase gradually after occlusion. Before the occlusion, the pressure in the high pressure side (e.g., the receiving chamber) is stable and almost unchanged; the magnitude of the pressure is determined by the dynamic pressure of the seals. Therefore, the current decay is relatively unchanged as well before occlusion.

During pump off time, the potential across first electrode 110 and second electrode 112 changes as a function of time. The potential across first electrode 110 and second electrode 112 during pump off time can be referred to as open circuit potential, and the change in potential across first electrode 110 and second electrode 112 as a function of time during pump off time can be referred to as open circuit potential decay. As mentioned previously, a change in pressure in electrokinetic solution receiving chamber 118 can cause a change in open circuit potential, ΔV, due to streaming potential, as expressed by Equation 1:

$$\Delta V = \epsilon\xi\Delta P/(\eta\sigma) \qquad \text{Equation 1}$$

where
ε=the permittivity of electrokinetic solution 114
ξ=the zeta potential of electrokinetic porous media 108
η=the viscosity of electrokinetic solution 114
σ=the electrical conductivity of electrokinetic solution 114
ΔP=P2−P1, the change in pressure in electrokinetic solution receiving chamber 118 between two consecutive shots As discussed previously, current draw through electrokinetic porous media 108 during pump on time, decay of current draw through electrokinetic porous media 108 during pump on time, open circuit potential across first electrode 110 and second electrode 112 during pump off time, and open circuit potential decay across first electrode 110 and second electrode 112 during pump off time are a function of the pressure in electrokinetic solution receiving chamber 118. Occlusions and leaks in an electrokinetic infusion pump can be detected by monitoring current draw through electrokinetic porous media 108 during pump on time, decay of current draw through electrokinetic porous media 108 during pump on time, open circuit potential across first electrode 110 and second electrode 112 during pump off time, and open circuit potential decay across first electrode 110 and second electrode 112 during pump off time. These parameters can be used to supplement monitoring of the position of movable partition 120 by position sensors, as discussed previously.

In some embodiments, position sensor readings of a movable partition (e.g., used to drive infusion fluid) and/or open circuit potential across electrodes during pump off time can be used to detect an occlusion such as one located in infusion reservoir outlet. After an occlusion occurs, the rate at which position sensor readings of movable partition change as a function of time can decrease. The open circuit potential, and/or the open circuit potential decay, across electrodes during pump off time can increase after an occlusion occurs.

In some exemplary embodiments of the present invention, before an occlusion occurs (e.g., in an infusion set outlet), the position sensor readings of the movable partition can change by more than about 4 sensor units per cycle when delivering infusion liquid at a basal rate of about 0.15 microliters/min.; by more than about 4 sensor units per cycle when delivering infusion liquid at a basal rate of about 0.5 microliters/min.; and by more than about 50 sensor units per cycle when delivering infusion liquid at a basal rate of about 5.83 microliters/min. In these embodiments, when delivering infusion liquid at a basal rate of about 0.15 microliters/min., pump on time is approximately 5 seconds, pump off time is approximately 180 seconds, and one cycle takes approximately 185 seconds. When delivering infusion liquid at a basal rate of about 0.5 microliters/min., pump on time is approximately 5 seconds, pump off time is approximately 55 seconds, and one cycle takes approximately 60 seconds. When delivering infusion liquid at a basal rate of about 5.83 microliters/min, pump on time is approximately 25 seconds, pump off time is approximately 35 seconds, and one cycle takes approximately 60 seconds. After an occlusion occurs (e.g., in the infusion set outlet), the position sensor readings of a movable partition can change by less than about 1 sensor units per cycle when delivering infusion liquid at a basal rate of about 0.15 microliters/min.; by less than about 1 sensor units per cycle when delivering infusion liquid at a basal rate of about 0.5 microliters/min.; and by less than about 10 sensor units per cycle when delivering infusion liquid at a basal rate of about 5.83 microliters/min.

In some other exemplary embodiments of the present invention, the open circuit potential decay across electrodes during pump off time can increase after an occlusion occurs by approximately 1 millivolt per cycle when delivering infusion liquid at a basal rate of about 0.15 microliters/min.; by approximately 2 millivolts per cycle when delivering infusion liquid at a basal rate of about 0.5 microliters/min.; and by approximately 21 millivolts per cycle when delivering infusion liquid at a basal rate of about 5.83 microliters/min.

In some embodiments, monitoring open circuit potential and/or open circuit potential decay across electrodes during pump off time can also be used to detect leaks in an electrokinetic infusion pump, e.g., in an infusion reservoir outlet, an infusion reservoir, and/or an electrokinetic solution receiving chamber. As supported by the examples herein, there is a pronounced correlation between leaks in electrokinetic solution receiving chamber, infusion reservoir, and infusion reservoir outlet, and open circuit potential across electrodes during pump off time. This correlation can be used to detect leaks in an electrokinetic infusion pump, according to an embodiment of the present invention.

The position sensor readings of a movable partition can also be used to detect leaks in an electrokinetic infusion pump. In some exemplary embodiments, when no leak is present, the position sensor readings of a movable partition can change by more than approximately 4 sensor units per cycle when delivering infusion liquid at a basal rate of about 0.5 microliters/min. When a leak occurs, the position sensor readings of the movable partition can change by more than approximately 8 sensor units per cycle when delivering infusion liquid at a basal rate of about 0.5 microliters/min. When delivering infusion liquid at a basal rate of about 0.5 microliters/min, pump on time can be approximately 5 seconds, pump off time can be approximately 55 seconds, and one cycle can last approximately 60 seconds. Hence, the position sensor readings of a movable partition can be used to detect leaks in an electrokinetic infusion pump, according to an embodiment of the present invention.

In some embodiments of the present invention, various methodologies can be used in combination to detect errors that occur in an electrokinetic infusion pump. For instance, two or more measurements selected from voltage measurements, current measurements, and partition position measurements can be used to detect malfunctions in an infusion pump. Utilizing any of the techniques disclosed by the present application, measurements of current, voltage, or partition position can be compared with corresponding expected sample values to provide an indication of pump malfunction. For example, current draw through electrokinetic porous media (e.g., the magnitude of the current transient during pump on time) and/or the open circuit potential across electrodes (e.g., the magnitude of the voltage transient during pump off time) can be used to detect occlusions in infusion reservoir outlet by themselves, or can be combined with information about the position of movable partition, to detect occlusions such as in an infusion reservoir outlet. With respect to exemplary FIGS. 1A and 1B, if electrokinetic infusion pump with closed loop control 100 is occluded, the magnitude of decay in current draw through electrokinetic porous media 108 during pump on time will increase, streaming potential or open circuit potential across first electrode first electrode 110 and second electrode second electrode 112 during pump off time will increase, and the position of movable partition 120, as measured by previously described position sensors, will not change as expected (in this case, moving less). Such malfunctions can be associated with pump mechanics, or a controller used to maintain operation of the infusion pump. Some type of indicator, such as an alarm or other visual or audio signal, can be provided to indicate the malfunction to a user, or to a controller, to take appropriate action such as pump shut down or limiting pump operation in some manner.

In some embodiments discussed previously, the open circuit potential across electrodes (e.g., during pump off time) and current decay through electrokinetic porous media (e.g., during pump on time) are a function of pressure in the infusion reservoir outlet, the infusion reservoir, and/or the electrokinetic solution receiving chamber. In some embodiments of this invention, however, the pressure is further modified by a hydraulic amplification factor intrinsic in an electrokinetic pump design. For instance, when the cross sectional area of an infusion fluid reservoir is larger than the cross sectional area of electrokinetic solution receiving chamber, the pressure change in the electrokinetic solution receiving chamber can be greater than the pressure change in the infusion fluid reservoir by a factor equivalent to the ratio of the cross sectional area of the infusion fluid reservoir to the cross sectional area of the electrokinetic solution receiving chamber.

For example, in a preferred embodiment, the cross sectional area of infusion reservoir is four times larger than the cross sectional area of electrokinetic solution receiving chamber. A fixed displacement of electrokinetic solution into electrokinetic solution receiving chamber results in a larger displacement of infusion liquid from infusion reservoir. Thus, a smaller overall footprint for an electrokinetic infusion pump can be used since a smaller volume of electrokinetic solution is required to displace a fixed volume of infusion liquid. As a result of the cross sectional area of infusion reservoir being 4 times larger than the cross sectional area of electrokinetic solution receiving chamber, when a change in pressure of over 1 psi occurs in infusion reservoir a change in pressure of over 4 psi occurs in electrokinetic solution receiving chamber.

Types of Malfunctions which can be Detected Using Electrokinetic Measurements

FIG. 9 presents a table, which discloses some exemplary techniques to detect failure modes and functioning of an electrokinetic infusion pumps consistent with embodiments of the present invention, including some techniques previously discussed herein. In the first column of FIG. 9, a list of potentially sensed parameters is presented. Sensed parameters include occlusions, partial occlusions, leaks in infusion sets, leaks in pump seals, leaks in electrokinetic porous media, bubble formation on electrodes, bubbles in pump chambers, loss of electrical contact with electrodes, empty electrokinetic solution supply reservoir, amount of infusion liquid dispensed, empty infusion liquid reservoir, and malfunctions in electrokinetic porous media. The remaining columns of FIG. 9 disclose various techniques for detecting sensed parameters. These techniques include current draw through electrokinetic porous media during pump on time, decay of current draw through electrokinetic porous media during pump on time, open circuit potential across first electrode and second electrode during pump off time, and position of movable partition. It is understood that combinations of these techniques can be utilized in conjunction to provide malfunction detection, as well as combining these techniques with other embodiments discussed herein. All such alterations are contemplated by the present application.

With reference to FIG. 9 and FIGS. 1A & 1B, and consistent with embodiments of the present invention, occlusions can be detected. For instance, such occlusions can be detected by monitoring current draw through electrokinetic porous media 108, which can be during pump on time. Current draw through electrokinetic porous media 108 during pump on time can decrease when an occlusion occurs, which can be due in part to a decrease in flow of electrokinetic solution 114 through electrokinetic porous media 108. The magnitude of decay in current draw through electrokinetic porous media 108 during pump on time can increase when an occlusion occurs, which can also be due in part to a decrease in flow of electrokinetic solution 114 through electrokinetic porous media 108. The open circuit potential across first electrode 110 and second electrode 112 measured during pump off time can increase when an occlusion occurs; this can be due to a rise in pressure in infusion reservoir outlet 123, infusion reservoir 122, electrokinetic solution receiving chamber 118, and/or the streaming potential caused by flow of electrokinetic solution 114 through electrokinetic porous media 108 during pump off time. Moveable partition 120 typically does not move as expected when an occlusion occurs, e.g., moving less than expected due to the occlusion. As mentioned previously, the position of moveable partition 120 can be determined using a variety of techniques.

In some embodiments, a partial occlusion can be detected in accord with the effects documented in FIG. 9. When a partial occlusion occurs, the same effects are observed as with an occlusion, but to a lesser extent. For example, with reference to exemplary FIGS. 1A and 1B, current draw through electrokinetic porous media 108 during pump on time can decrease when a partial occlusion occurs, which can be due in part to a decrease in flow of electrokinetic solution 114 through electrokinetic porous media 108. The magnitude of decay in current draw through electrokinetic porous media 108 during pump on time can increase when a partial occlusion occurs, which can also be due in part to a decrease in flow of electrokinetic solution 114 through electrokinetic porous media 108. The open circuit potential across first electrode 110 and second electrode 112 measured during pump off time can increase when a partial occlusion occurs, which can be due to a rise in pressure in infusion reservoir outlet 123, infusion reservoir 122, electrokinetic solution receiving chamber 118, and/or the streaming potential caused by flow of electrokinetic solution 114 through electrokinetic porous media 108 during pump off time. Moveable partition 120 can not move as expected when a partial occlusion occurs.

In some embodiments, when either an occlusion or a partial occlusion occurs, pressure can build up in the pump, such as in electrokinetic solution receiving chamber 118, causing backflow of electrokinetic solution 114 across electrokinetic porous media 108 during pump off time. As a result, current draw through electrokinetic porous media 108 may occasionally drift higher during pump on time (while pumping electrokinetic solution 114 that backflowed), although the major effect of an occlusion is to decrease average current draw through electrokinetic porous media 108.

With reference to the third row of FIG. 9 and FIGS. 1A & 1B, leaks in infusion reservoir outlet 123 and infusion sets connected to infusion reservoir outlet 123 can be detected in accord with embodiments of the present application. Leaks can be detected by monitoring current draw through electrokinetic porous media 108 (e.g., during pump on time). Current draw through electrokinetic porous media 108 during pump on time can increase or decrease when leaks in infusion reservoir outlet 123 and infusion sets connected to infusion reservoir outlet 123 occur, which can be due in part to an increase in flow of electrokinetic solution 114 through electrokinetic porous media 108 and/or changes in the conductivity of electrokinetic solution 114 in the vicinity of electrokinetic porous media 108. The magnitude of decay in current draw through electrokinetic porous media 108 during pump on time can decrease when leaks in infusion reservoir outlet 123 and/or infusion sets connected to infusion reservoir outlet 123 occur, which can be due in part to an increase in flow of electrokinetic solution 114 through electrokinetic porous media 108 and/or a decrease of pressure in electrokinetic solution receiving chamber 118. The open circuit potential across first electrode 110 and second electrode 112 measured during pump off time can decrease when leaks in infusion reservoir outlet 123 and/or infusion sets connected to infusion reservoir outlet 123 occur, which can be due to a decrease in pressure in infusion reservoir outlet 123, infusion reservoir 122, electrokinetic solution receiving chamber 118, and/or the streaming potential caused by flow of electrokinetic solution 114 through electrokinetic porous media 108 during pump off time. Moveable partition 120 does not typically move as expected when leaks in infusion reservoir outlet 123 and/or infusion sets connected to infusion reservoir outlet 123 occur (e.g., moving more than expected due to leaks in infusion reservoir outlet 123 and/or infusion sets connected to infusion reservoir outlet 123).

With reference to the fourth row of FIG. 9 and FIGS. 1A & 1B, leaks in seals associated with electrokinetic solution receiving chamber 118, movable partition 120, and infusion reservoir 122, among other pump portions, can be detected consistent with embodiments of the present invention. For instance, the aforementioned leaks can be detected by monitoring current draw through electrokinetic porous media 108 during pump on time. Current draw through electrokinetic porous media 108 (e.g., during pump on time) can increase or decrease when leaks in seals associated with electrokinetic solution receiving chamber 118, movable partition 120, and infusion reservoir 122, and/or other pump portions occur, which can be due in part to an increase in flow of electrokinetic solution 114 through electrokinetic porous media 108 and/or changes in the conductivity of electrokinetic solution 114 in the vicinity of electrokinetic porous media 108. The magnitude of decay in current draw through electrokinetic porous media 108 during pump on time can decrease when leaks in seals occur, which can be due in part to an increase in flow of electrokinetic solution 114 through electrokinetic porous media 108 and/or a decrease of pressure in electrokinetic solution receiving chamber 118. The open circuit potential across first electrode 110 and second electrode 112 measured during pump off time can decrease when leaks in seals occur, which can be due to a decrease in pressure in infusion reservoir outlet 123, infusion reservoir 122, electrokinetic solution receiving chamber 118, and/or the streaming potential caused by flow of electrokinetic solution 114 through electrokinetic porous media 108 during pump off time. Moveable partition 120 does not typically move as expected when leaks in seals occur (e.g., moving less than expected due to leaks in seals associated with electrokinetic solution receiving chamber 118, movable partition 120, and/or infusion reservoir 122).

With reference to the fifth row of FIG. 9 and FIGS. 1A & 1B, leaks in seals associated with electrokinetic porous media 108 can be detected in accord with embodiments of the present invention. For example, leaks in seals associated with the porous media can be detected by monitoring the current draw through electrokinetic porous media 108 during pump on time. Current draw through electrokinetic porous media 108 during pump on time can increase when leaks in seals associated with electrokinetic porous media 108 occur, which can be due in part to an increase in flow of electrokinetic solution 114 through and around electrokinetic porous media 108. The magnitude of decay in current draw through electrokinetic porous media 108 during pump on time can increase when leaks in seals associated with electrokinetic porous media 108 occur, which can also be due in part to an increase in flow of electrokinetic solution 114 through and around electrokinetic porous media 108. The open circuit potential across first electrode 110 and second electrode 112 measured during pump off time can decrease when leaks in seals associated with electrokinetic porous media 108 occur, which can be due to a decrease in pressure in infusion reservoir outlet 123, infusion reservoir 122, electrokinetic solution receiving chamber 118, and/or the streaming potential caused by flow of electrokinetic solution 114 through electrokinetic porous media 108 during pump off time. Moveable partition 120 typically will not move as expected when leaks in seals associated with electrokinetic porous media 108 occur (e.g., moving less due to leaks in seals associated with electrokinetic porous media 108).

With reference to the sixth row of FIG. 9 and FIGS. 1A & 1B, the formation of bubbles at first electrode 110 or second electrode 112 can be detected (e.g., at a capacitive electrode). In one instance, bubble formation can be detected by monitoring the current draw through electrokinetic porous media 108 during pump on time. Current draw through electrokinetic porous media 108 during pump on time can increase when bubbles are formed on first electrode 110, which can be due in part to an increase in flow of electrokinetic solution 114 through electrokinetic porous media 108 caused by an increase in pressure in electrokinetic supply reservoir 106. Moveable partition 120 will not typically move as expected when bubbles are formed on first electrode 110 or second electrode 112 (e.g., moving more due to bubble expansion in electrokinetic supply reservoir 106 and/or electrokinetic solution receiving chamber 118).

With respect to the open circuit potential across first electrode 110 and second electrode 112 measured during pump off time, the potential can deviate from an expected charging curve profile when capacitive electrodes are utilized. Capacitive electrodes operate by storing charge in an electrical double layer on the capacitive electrode surface. Typically, electrical parameters can be measured to monitor the operation of capacitive electrodes. For example, charging current can be monitored to gauge the charging rate of capacitive electrodes, and voltage can be monitored to measure the state of charge of capacitive electrodes. Capacitive electrodes are typically designed to require charging voltage below 1.2 volts, which is the approximate threshold of electrochemical oxidation or reduction of electrokinetic solution. If, inadvertently, the charging voltage exceeds 1.2 volts, water in the pumps electrokinetic solution can be electrochemically decomposed, forming hydrogen and oxygen gas. If the hydrogen or oxygen nucleate, they can form bubbles. Bubbles can displace electrokinetic solution, and affect pump delivery rate. Thus, it can be advantageous to hinder bubble formation, and to monitor unanticipated bubble formation. Though the above discussion is in the context of bubble formation due to hydrolysis, it is understood that some embodiments are directed to detection of bubble formation independent of any particular mechanism of bubble formation.

According to an embodiment of the current invention, the voltage across capacitive electrodes can be used to detect the formation of bubbles, without requiring visual inspection of the electrokinetic infusion pump with closed loop control. In particular, a voltage charging curve, corresponding with open circuit voltage measurements, of capacitive electrodes can be monitored. The charging curve typically follows some expected profile, or changes within a given range over a designated time period. When the voltage value deviates from the expected charging curve, or changes value in a manner outside some designated tolerance range over a period of time, the deviation can provide an indication of the onset of bubble formation. For example, an open circuit potential measurement can increase when bubbles are formed on an electrode, which can be due to an increase in pressure in electrokinetic solution receiving chamber 118 and the streaming potential caused by flow of electrokinetic solution 114 through electrokinetic porous media 108 during pump off time. Other mechanisms, however, are also within the scope of the present application.

With respect to the seventh row of FIG. 9 and FIGS. 1A & 1B, the formation of bubbles in infusion reservoir 122, infusion reservoir outlet 123, and/or infusion sets connected to infusion reservoir outlet 123 can be detected in accord with embodiments of the present invention. For example, bubbles can be detected by monitoring current draw through electrokinetic porous media 108 during pump on time. Current draw through electrokinetic porous media 108 during pump on time can vary as bubbles are compressed in infusion reservoir 122, infusion reservoir outlet 123, and/or infusion sets connected to infusion reservoir outlet 123, which can be due in part to variable flow of electrokinetic solution 114 through electrokinetic porous media 108. The open circuit potential across first electrode 110 and second electrode 112 measured during pump off time can increase when bubbles are formed in infusion reservoir 122, infusion reservoir outlet 123, and/or infusion sets connected to infusion reservoir outlet 123, which can be due to an increase in pressure in electrokinetic solution receiving chamber 118 and the streaming potential caused by flow of electrokinetic solution 114 through electrokinetic porous media 108 during pump off time. Moveable partition 120 will not typically move as expected when bubbles are formed in infusion reservoir 122, infusion reservoir outlet 123, and/or infusion sets connected to infusion reservoir outlet 123 (e.g., continuing to move during pump off time due to expansion of bubbles in infusion reservoir 122, infusion reservoir outlet 123, and/or infusion sets connected to infusion reservoir outlet 123).

With respect to the eighth row of FIG. 9 and FIGS. 1A & 1B, a break in electrical contact with first electrode 110 or second electrode 112 can be detected consistent with embodiments of the present invention. For instance, a break can be detected by monitoring current draw through electrokinetic porous media 108 during pump on time. Current draw through electrokinetic porous media 108 during pump on time can fall toward zero due to a break or near break in electrical contact with first electrode 110 or second electrode 112. The open circuit potential across first electrode 110 and second electrode 112 during pump off time is typically not measurable if a break in electrical contact with first electrode 110 or second electrode 112 is made. Movable partition 120 typically will not move as expected if a break in electrical contact with first electrode 110 or second electrode 112 occurs (e.g., moving less than expected).

With reference to the ninth row of FIG. 9 and FIGS. 1A & 1B, an empty electrokinetic supply reservoir 106 can be detected using some embodiments of the present invention. The empty reservoir 106 can be detected by monitoring current draw through electrokinetic porous media 108 during pump on time. Current draw through electrokinetic porous media 108 during pump on time can decrease, which can be due in part to decreased flow of electrokinetic solution 114 through electrokinetic porous media 108. The open circuit potential across first electrode 110 and second electrode 112 measured during pump off time can decrease when electrokinetic supply reservoir 106 is empty, which can be due to a decreases in pressure in electrokinetic solution receiving chamber 118 and the streaming potential caused by flow of electrokinetic solution 114 through electrokinetic porous media 108 during pump off time. Movable partition 120 will typically not move as expected when electrokinetic supply reservoir 106 is empty (e.g., moving less, since electrokinetic solution 114 does not flow through electrokinetic porous media 108, and pressure does not build in electrokinetic solution receiving chamber 118).

With respect to the tenth row of FIG. 9 and FIGS. 1A & 1B, the amount of infusion liquid 124 that is dispensed can be detected in accord with embodiments of the present invention. For example, the amount of infusion fluid 124 dispensed can be estimated by monitoring current draw through electrokinetic porous media 108 during pump on time. Current draw through electrokinetic porous media 108 during pump on time can be used to estimate the amount of electrokinetic solution 114 that has been pumped through electrokinetic porous media 108, which can be correlated to the amount of infusion liquid 124 that has been displaced from infusion reservoir 122. The open circuit potential across first electrode 10 and second electrode 112 measured during pump off time can also be used to estimate the amount of electrokinetic solution 114 that has been pumped through electrokinetic porous media 108, and can be correlated to the amount of infusion liquid 124 that has been displaced from infusion reservoir 122. The position of movable partition 120 can be directly related to the volume of infusion reservoir 122 and the volume of infusion liquid 124 dispensed from infusion reservoir 122 by way of infusion reservoir outlet 123. As mentioned previously, the position of movable partition 120 can be determined using a wide variety of techniques, and can be a direct indicator of the amount of infusion liquid 124 dispensed from infusion reservoir 122.

With respect to the eleventh row of FIG. 9 and FIGS. 1A & 1B, an empty infusion reservoir 122 can be detected in accord with embodiments of the present invention. Detection of an empty infusion reservoir 122 can be achieved by monitoring the current draw through electrokinetic porous media 108 during pump on time. Current draw through electrokinetic porous media 108 during pump on time can decrease since movable partition 120 can no longer move, electrokinetic solution receiving chamber 118 cannot accommodate additional electrokinetic solution 114, and/or direct flow of electrokinetic solution 114 through electrokinetic porous media 108 can no longer occur. However, in some cases, current draw through electrokinetic porous media 108 during pump on time can increase when infusion reservoir 122 is empty, if electrokinetic solution 114 circulates in electrokinetic porous media 108, between electrokinetic solution receiving chamber 118 and electrokinetic supply reservoir 106. The open circuit potential across first electrode 110 and second electrode 112 measured during pump off time can increase when infusion reservoir 122 is empty, which can be due to an increase in pressure in electrokinetic solution receiving chamber 118 and the streaming potential caused by flow of electrokinetic solution 114 through electrokinetic porous media 108 during pump off time. Movable partition 120 will not typically move as expected when electrokinetic supply reservoir 106 is empty. This can be because the movable partition 120 reaches the end of infusion housing 116 and can no longer move.

With respect to the twelfth row of FIG. 9 and FIGS. 1A & 1B, a malfunction related to electrokinetic porous media 108 can be detected. The malfunction can be detected by monitoring current draw through electrokinetic porous media 108 during pump on time. Current draw through electrokinetic porous media 108 during pump on time can deviate from expected behavior if a problem occurs related to electrokinetic porous media 108. For example, if the seal leaks between electrokinetic porous media 108 and electrokinetic supply reservoir 106 or electrokinetic solution receiving chamber 118, allowing electrokinetic solution 114 to flow around rather than through electrokinetic porous media 108, current draw through electrokinetic porous media 108 during pump on time can be less than expected. Similarly, the open circuit potential across first electrode 110 and second electrode 112 measured during pump off time can behave in an unexpected manner, which can be due, in part, to alternate flow paths of electrokinetic solution 114 through electrokinetic porous media 108. Movable partition 120 will not typically move as expected when a malfunction related to electrokinetic porous media 108 occurs. This can be because electrokinetic solution 114 can flow in an unexpected manner through electrokinetic porous media 108 and into electrokinetic solution receiving chamber 118 (e.g., the partition moves less than expected).

Figure 10A:
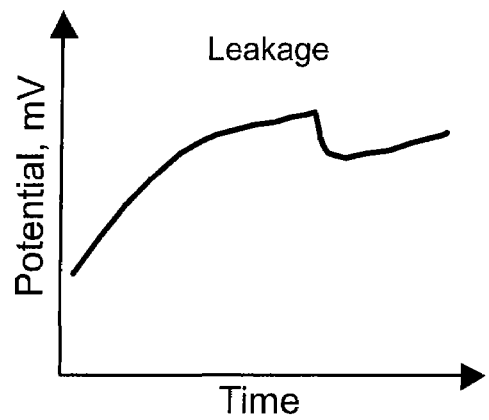
FIGS. 10A-10F are illustrations that include graphs of open circuit potential across electrodes measured during pump off time, and current draw through electrokinetic porous media during pump on time as a function of time for several failure modes, including some listed in FIG. 9, according embodiments of the present invention.

With reference to the schematic of FIGS. 1A and 1B, FIGS. 10A-10F provide exemplary illustrations of graphs of open circuit potential across first electrode 110 and second electrode 112 measured during pump off time and current draw through electrokinetic porous media 108 during pump on time as a function of time, for several of the modes described in the table of FIG. 9, in accord with embodiments of the present invention. FIG. 10A illustrates a graph of open circuit potential across first electrode 110 and second electrode 112 measured during pump off time versus time, when a leak occurs in infusion reservoir outlet 123, or in an infusion set connected to infusion reservoir outlet 123. As shown in FIG. 10A, a sudden decrease can occur in open circuit potential across first electrode 110 and second electrode 112 as measured during pump off time when a leak occurs.

Figure 10B:
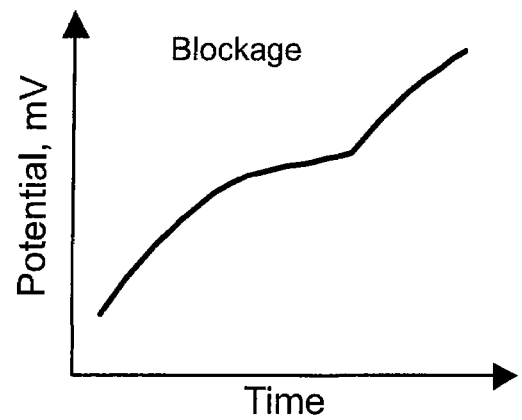

FIG. 10B illustrates a graph of open circuit potential across first electrode 110 and second electrode 112 measured during pump off time versus time, when an occlusion occurs in infusion reservoir outlet 123, or in an infusion set connected to infusion reservoir outlet 123. As shown in FIG. 10B, a sudden increase can occur in open circuit potential across first electrode 110 and second electrode 112 measured during pump off time when the occlusion occurs.

Figure 10C:
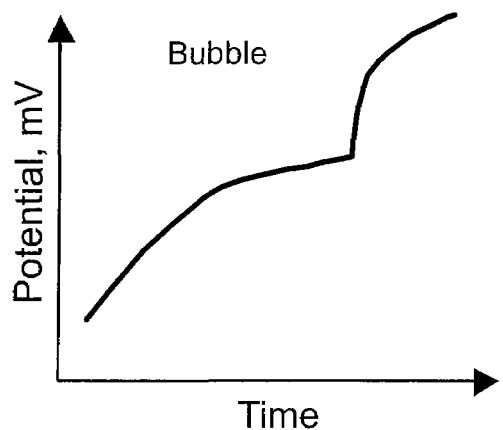

FIG. 10C illustrates a graph of open circuit potential across first electrode 110 and second electrode 112 measured during pump off time versus time, when a bubble forms in electrokinetic solution receiving chamber 118. As shown in FIG. 10C, a sudden increase can occur in open circuit potential across first electrode 110 and second electrode 112 measured during pump off time when the bubble is formed.

Although the open circuit potential profiles illustrated in FIGS. 10B and 10C are similar in shape, position sensor readings can be used to distinguish between an occlusion and a bubble in some embodiments. For instance, in the case of an occlusion, as illustrated in FIG. 10B, the position sensor can detect an unexpectedly small change in the position of movable partition 120. In the case of a bubble, as illustrated in FIG. 10C, the position sensor can detect a substantially normal change in the position of movable partition 120, or a change which is substantially smaller than if an occlusion of the infusion set occurred.

Figure 10E:
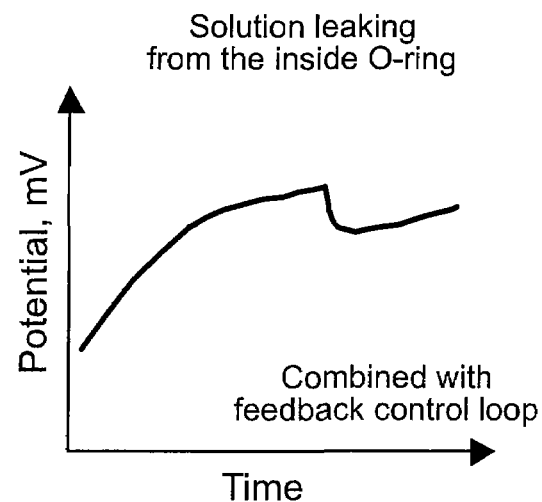
Figure 10D:
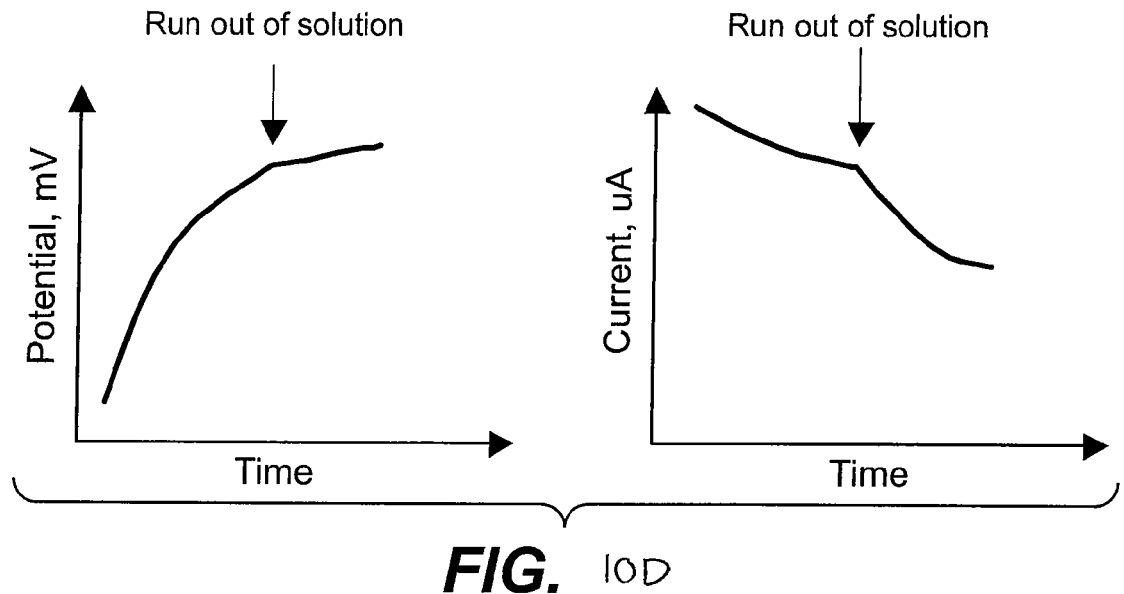

FIG. 10D illustrates a graph of open circuit potential across first electrode 110 and second electrode 112 measured during pump off time versus time, and a corresponding graph of current draw through electrokinetic porous media 108 during pump on time versus time, when electrokinetic supply reservoir 106 runs out of electrokinetic solution 114. As shown in FIG. 10D, a change in slope of the increase in open circuit potential across first electrode 110 and second electrode 112 can occur during pump off time when electrokinetic supply reservoir 106 runs out of electrokinetic solution 114. Correspondingly, a decrease can occur in current draw through electrokinetic porous media 108 during pump on time at the point in time when electrokinetic supply reservoir 106 runs out of electrokinetic solution 114.

FIG. 10E illustrates a graph of open circuit potential across first electrode 110 and second electrode 112 measured during pump off time versus time, when a leak of electrokinetic solution 114 from electrokinetic solution receiving chamber 118 occurs. As shown in FIG. 10E, a sharp decrease can occur in open circuit potential across first electrode 110 and second electrode 112 measured during pump off time when a leak of electrokinetic solution 114 from electrokinetic solution receiving chamber 118 occurs.

Although the open circuit potential profiles illustrated in FIGS. 10A and 10E are similar in shape, position sensor readings can be used to distinguish between a leak of infusion liquid 124 from infusion reservoir outlet 123 (or from an infusion set connected to infusion reservoir outlet 123) and a leak of electrokinetic solution 114 from electrokinetic solution receiving chamber 118 in some embodiments. For instance, in the case of a leak of infusion liquid 124 from infusion reservoir outlet 123 (or from an infusion set connected to infusion reservoir outlet 123), as illustrated in FIG. 10A, the position sensor can detect an unexpectedly large change in the position of movable partition 120. In the case of a leak of electrokinetic solution 114 from electrokinetic solution receiving chamber 118, as illustrated in FIG. 10E, the position sensor can detect unexpectedly small change in the position of movable partition 120.

Figure 10F:
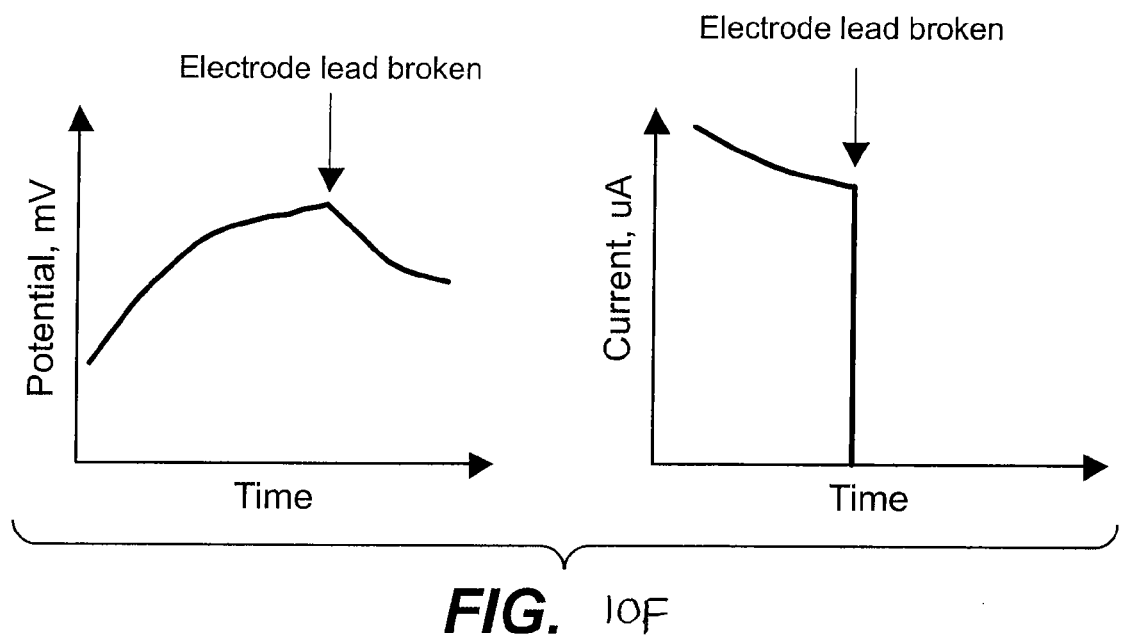

FIG. 10F illustrates a graph of open circuit potential across first electrode 110 and second electrode 112 measured during pump off time versus time, and a graph of current draw through electrokinetic porous media 108 during pump on time versus time, when electrical contact with first electrode 110 and second electrode 112 is broken, in accord with some embodiments of the invention. As shown in FIG. 10F, a sudden decrease can occur in open circuit potential across first electrode 110 and second electrode 112 measured during pump off time when electrical contact with first electrode 110 and second electrode 112 is broken, and a sharp decrease can occur in current draw through electrokinetic porous media 108 during pump on time when electrical contact with first electrode 110 and second electrode 112 is broken. In some instances, open circuit potential across first electrode 110 and second electrode 112 can be measured with a separate set of electrodes, i.e., not with first electrode 110 and second electrode 112, otherwise the open circuit potential would drop vertically to zero, as is the case with current draw through electrokinetic porous media 108 during pump on time.

Figure 11:
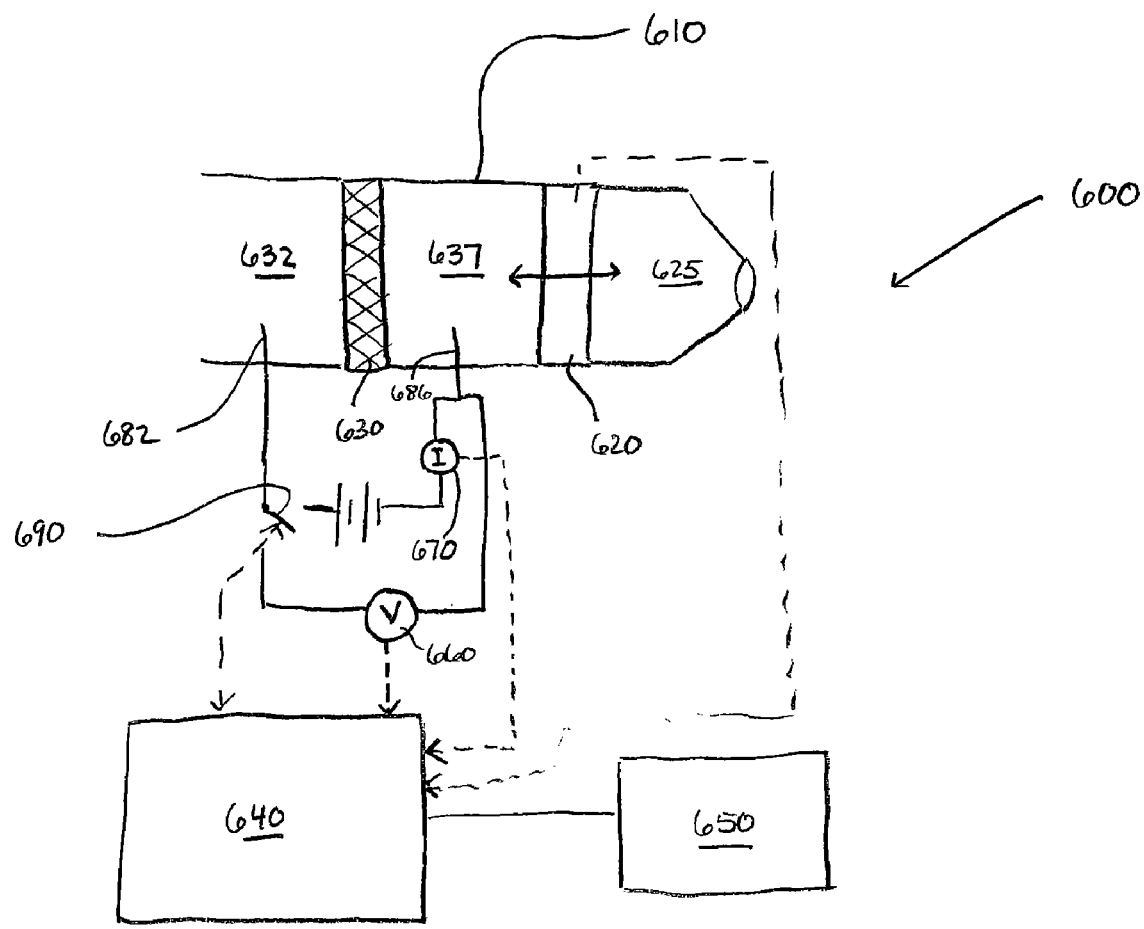
FIG. 11 is a schematic diagram of a system for detecting malfunctions in an electrokinetically driven infusion pump, consistent with embodiments of the present invention.

Some embodiments are directed to systems for detecting malfunctions in electrokinetic pumps, consistent with one or more of the schemes discussed herein. FIG. 11 provides a schematic diagram of one exemplary system 600. The system 600 includes an electrokinetically driven pump 610. The pump 610 has electrodes 682, 686 (e.g., capacitive electrodes) configured to provide a measurement between opposite sides of a porous media 630. By applying a voltage across the electrodes 682, 686, electrokinetic working fluid can be driven from a reservoir 632 to a receiving chamber 637. Build up of electrokinetic working fluid in the receiving chamber 637 increases the pressure in the chamber 637, driving moveable partition 620 that forces infusion fluid out of the infusion fluid holding chamber 625.

The system 600 can also include a processor 640. The processor can provide a number of functions such as running a controller, which can be integral with the processor, that implements a closed loop control scheme. For example, the processor can be embodied as one or more of the elements diagrammed in FIG. 7 for controlling operation of an electrokinetic infusion pump.

In some embodiments, a processor can be configured to carry out one or more functions that detect potential malfunctions in an electrokinetic infusion pump. Such functions include portions, or the entirety, of all the techniques disclosed within the present application for detecting malfunctions in an electrokinetic infusion pump. Accordingly, a system which can utilize such a configured processor can also configure other portions of the system (e.g., electrokinetic pump elements or other components) to implement a technique for detection pump malfunctions.

In one example, depicted by the schematic of FIG. 11, a processor 640 is configured to operate a switch 690 that powers-on or powers-off a pump 610. Accordingly, the processor 640 can be configured to run the pump 610 using activate/deactivate cycling, in accord with various embodiments disclosed herein. In addition, the processor 640 can be coupled to receive measurements from a voltage detection device 660 in an open circuit mode, and/or be coupled to current detection device 670 to detect current when a potential is applied across the electrodes 682, 686. Such devices 660, 670 can be used to provide electrode measurements that can be compared with sample measurements (e.g., transients embodied as one or more values), in accord with the embodiments disclosed herein. In such situations, the processor 640 can include, or can be separately coupled to, a storage device that holds the sample values; the storage device can be a read-write device if sample values correspond with previously measured electrode measurements consistent with some embodiments of the invention. The processor 640 can also be coupled to an alert mechanism 650. The alert mechanism 650 can be activated by the processor 640 when a pump malfunction is indicated.

The exemplary embodiment of FIG. 11 presents one particular arrangement of components for a system that can be used to detect malfunctions in an electrokinetic infusion pump. Those skilled in the art will readily appreciate that various hardware modifications can be made to the system. For example, the processor 640 can be embodied as a single physical device or a plurality of microprocessors that are integrated (e.g., coupled in series or parallel) to perform the functions discussed with respect to the system 600. Coupling of the processor 640, and other portions of the system 600, can utilize any number of mechanisms suitable for use with embodiments disclosed herein (e.g., hardwiring, RF, etc.). Furthermore, other types of configurations for pieces of the electrokinetic pump 610, alert mechanism 650, or elements thereof can also be implemented beyond what is explicitly stated in the present disclosure. All these variations, among others, are within the scope of the present application.

Use of Malfunction Detection Schemes in Non-Electrokinetically-Driven Infusion Pumps Though many embodiments discussed herein refer to malfunction detection schemes for infusion pumps that utilize an electrokinetic mechanism for driving the flow of infusion fluid, it should be understood that embodiments of the present invention are not limited to electrokinetically-driven infusion pumps. For instance, some exemplary embodiments are directed to infusion pumps in which infusion fluid is not driven by action of electrokinetic phenomena, but that utilize some type of electrokinetic mechanism to detect malfunctions in the infusion pump. For example, an infusion pump can include an electrokinetic mechanism that can act as a sensing unit to indicate infusion pump malfunction. Such electrokinetic mechanism can utilize any of the malfunction detection schemes discussed herein to provide an indication of pump malfunction (e.g., looking at a current measurement or voltage measurement between electrodes, and comparing such measurement with at least one sample value).

Figure 30:
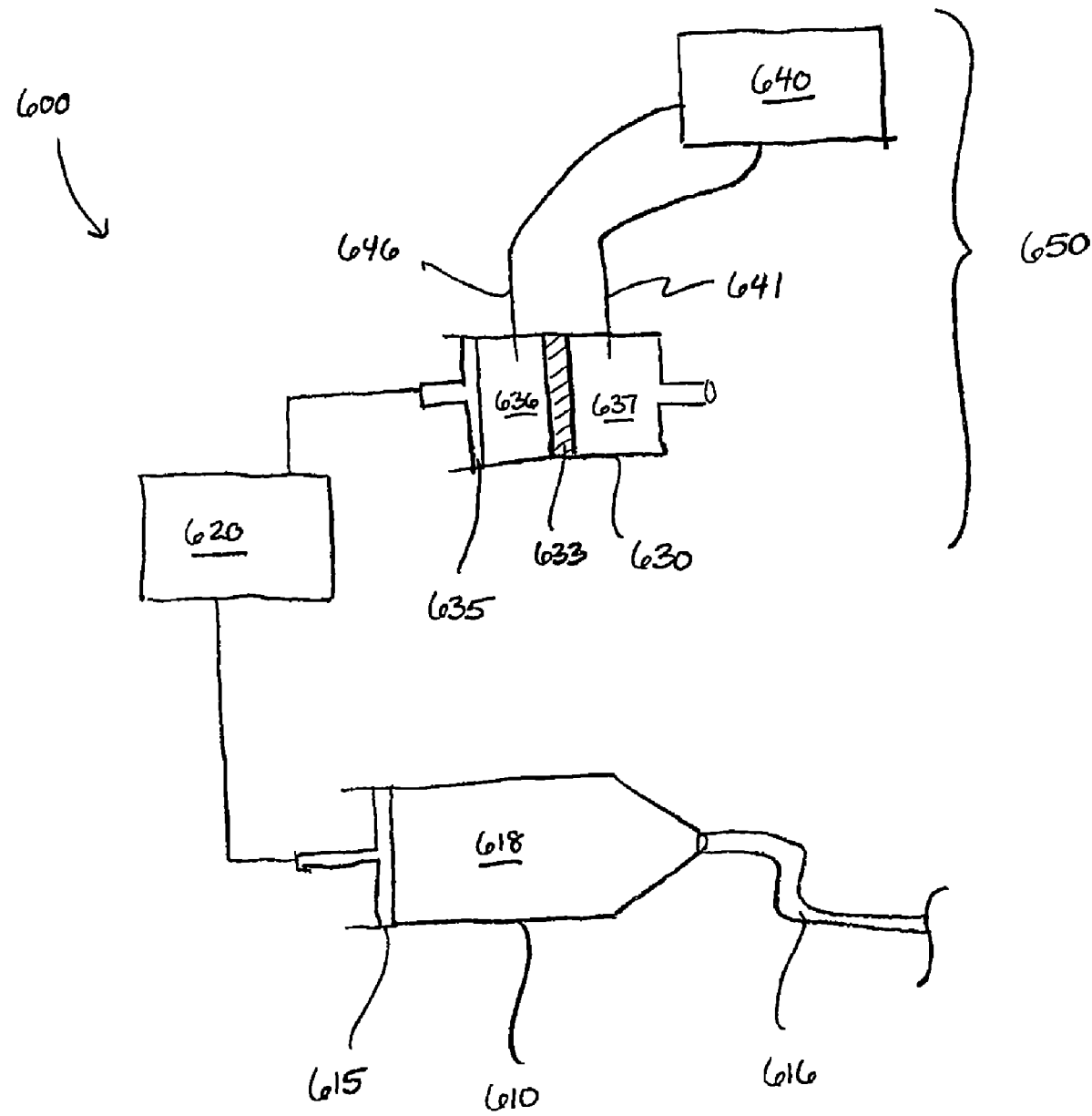
FIG. 30 presents a schematic diagram of an electrokinetic sensing mechanism used to detect malfunctions in a non-electrokinetically driven infusion pump, according to some embodiments of the invention.

One exemplary illustration of a system for implementing some of the embodiments discussed above is depicted in FIG. 30. An infusion pump system 600 is shown having an infusion fluid holding chamber 610 containing infusion fluid 618. The fluid 618 can be mechanically-driven from the chamber 610 into the infusion set 616 by a piston 615 that can be pushed by connection to an engine 620. The engine 620 can also simultaneously push a second piston 635 that is part of an electrokinetic sensing mechanism 650. The sensing mechanism 650 can include a chamber 630 for holding electrokinetic working fluid and a porous media 633. As the piston 635 is driven through the chamber 630, electrokinetic working fluid is forced from one region 636 through the porous media 633 and into the another region 637. Thus, a pressure differential is set up between the two regions 636, 637, which results in a streaming potential that can be measured using electrodes 641, 646. The electrodes 641, 646 are coupled to a malfunction detection unit 640 that can include elements such as a processor for implementing the various malfunction schemes discussed in the present application.

The pistons 615, 635 can be coupled to provide proportional displacement. That is, if one piston moves at a given velocity or a given distance, the other piston will move at a proportional velocity or a proportional distance. Thus, if a malfunction such as an occlusion occurs in the infusion set 616, the movement of piston 615 can be slowed. Accordingly, the movement of piston 635 is slowed, resulting in a lower pressure differential between the regions 636, 637 of the electrokinetic fluid chamber 630. Thus, the measured streaming potential is proportionally smaller. Thus, if the measured streaming potential is less than some expected potential value, the malfunction mechanism 640 can be activated to indicate an occlusion's presence. Clearly, analogous detection can be achieved by looking at a current measurement using electrodes 641, 646 (e.g., an occlusion resulting in less current flow because of less fluid flowing between regions 636, 637). Leak detection can also be carried out since the pistons 615, 635 would move faster, resulting in a higher streaming potential measurement or a higher current measurement in the electrokinetic fluid chamber 630. It is also clear that many modification of the exemplary system 600 can be made consistent with embodiments of the present invention. For example, in some cases, a membrane (not shown) can be directly incorporated into the infusion fluid chamber 610, and electrodes can also be incorporated to provide a direct measure of streaming potential as fluid is mechanically forced through the infusion fluid chamber 610.

It should be understood that various alternatives to the embodiments of the invention described within the present application may be employed in practicing the invention. It is intended that the claims define the scope of the invention and that structures within the scope of these claims and their equivalents be covered thereby.

EXAMPLES

The following examples are provided to illustrate some aspects of the present application. The examples, however, are not intended to limit the scope of any embodiment of the invention.

Example 1

Basal and Bolus Liquid Delivery

Using an electrokinetic infusion pump with closed loop control 100 as illustrated in FIG. 6, basal and bolus infusion liquid delivery rates were determined. In basal infusion, small volumes are dispensed as a series of shots. In bolus infusion, large volumes are dispensed in a single shot of longer duration. Basal and bolus infusion liquid delivery rates were determined by applying voltage to electrokinetic engine 102 for a period of time (referred to as the pump on time), then switching the voltage off for a period of time (referred to as the pump off time). The sum of pump on time and pump off time is referred to as cycle time in this example. The mass of infusion liquid pumped during each cycle time (referred to as the shot size) was determined with a Mettler Toledo AX205 electronic balance. The shot size was determined repeatedly, using the same pump on time and the same cycle time, giving an indication of shot size repeatability. Using the density of water (about 1 gram per cubic centimeter), the shot size volume was derived from the mass of infusion liquid pumped during each cycle time.

Electrokinetic engine 102 was connected to infusion module 104 using connection tubing 244. Connection tubing 244 was rigid PEEK tubing with an inside diameter of 0.040", an outside diameter of 0.063", and a length of approximately 3". A similar piece of PEEK tubing, approximately 24" long, was connected to infusion reservoir outlet 123 on one end, and to glass capillary tubing on the other end. The glass capillary tubing had an inside diameter of 0.021", an outside diameter of 0.026", and a length of about 6". The end of the glass capillary tubing, which was not connected to infusion reservoir outlet 123, was inserted into a small vial being weighed by the Mettler Toledo AX205 electronic balance. A small amount of water was placed in the bottom of the small vial, covering the end of the glass capillary tubing, and a drop of oil was placed on top of the water in the bottom of the small vial to reduce evaporation of the water. Electrokinetic engine 102 was also connected to a vented electrokinetic solution reservoir (not shown in FIG. 6) that provided electrokinetic solution to electrokinetic engine 102. Electrokinetic engine 102, vented electrokinetic solution reservoir, infusion module 104, connection tubing 244, the glass capillary tubing, and the Mettler Toledo AX205 electronic balance, were placed inside a temperature-controlled box, held to +/−1° C., to eliminate measurement errors associated with temperature variations. The temperature-controlled box was placed on top of a marble table to reduce errors from vibration. A personal computer running LabView software controlled electrokinetic infusion pump with closed loop control 100 and collected data from the Mettler Toledo AX205 electronic balance.

To determine basal delivery of infusion liquid, electrokinetic engine 102 was connected to infusion module 104 with connection tubing 244 and driven with a potential of 75 volts. At 75 volts, electrokinetic engine 102 delivered electrokinetic solution to infusion module 104 at a rate of approximately 15 microliters/minute. Electrokinetic engine 102 was run with an on time of approximately 2 seconds and an off time of approximately 58 seconds, resulting in a cycle time of 60 seconds and a shot size of approximately 0.5 microliters. The on-time of electrokinetic engine 102 was adjusted, based upon input from magnetostrictive waveguide 177 and position sensor control circuit 160, which ran a closed loop control algorithm. For each cycle of basal delivery, the position of moveable permanent magnet 149 was determined. If moveable permanent magnet 149 did not move enough, the on time for the next cycle of basal delivery was increased. If moveable permanent magnet 149 moved too much, the on time for the next cycle of basal delivery was decreased. The determination of position of moveable permanent magnet 149, and any necessary adjustments to on time, was repeated for every cycle of basal delivery.

To determine bolus delivery of infusion liquid, electrokinetic engine 102 was connected to infusion module 104 with connection tubing 244 and driven with a potential of 75 volts. Once again, at 75 volts electrokinetic engine 102 delivered electrokinetic solution to infusion module 104 at a rate of approximately 15 microliters/minute. Electrokinetic engine 102 was run with an on time of approximately 120 seconds and an off time of approximately 120 seconds, resulting in a cycle time of 4 minutes and a shot size of approximately 30 microliters. For each cycle of bolus delivery, the position of moveable permanent magnet 149 was determined while the electrokinetic engine 102 was on. Once moveable permanent magnet 149 moved the desired amount, electrokinetic engine 102 was turned off. The position of moveable permanent magnet 149 was used to control on time of electrokinetic engine 102 for every cycle of bolus delivery.

Figure 12:
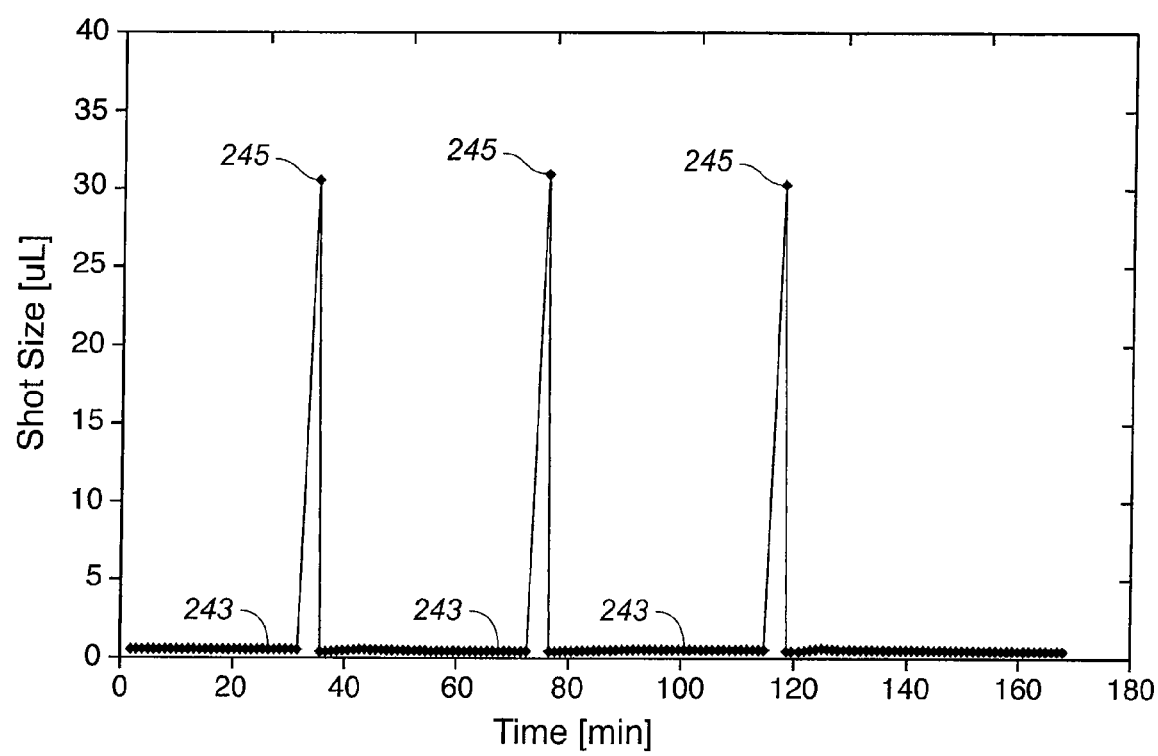
FIG. 12 presents a graph showing the performance of the electrokinetic infusion pump with closed loop control illustrated in FIG. 6 in both basal and bolus modes.

Basal and bolus delivery of infusion liquid were alternated, as follows. Thirty cycles of basal delivery was followed by one cycle of bolus delivery. Then, thirty-seven cycles of basal delivery, was followed by one cycle of bolus delivery. Finally, thirty-eight cycles of basal delivery was followed by a one cycle of bolus delivery and forty-nine additional cycles of basal delivery. FIG. 12 is a graph showing measured shot size as a function of time, for alternating basal delivery 243 and bolus delivery 245, as outlined above. In basal mode, the average shot size was about 0.5 microliters with a standard deviation of less than 2%.

Example 2

Occlusion Detection with Closed Loop Control

Figure 13:
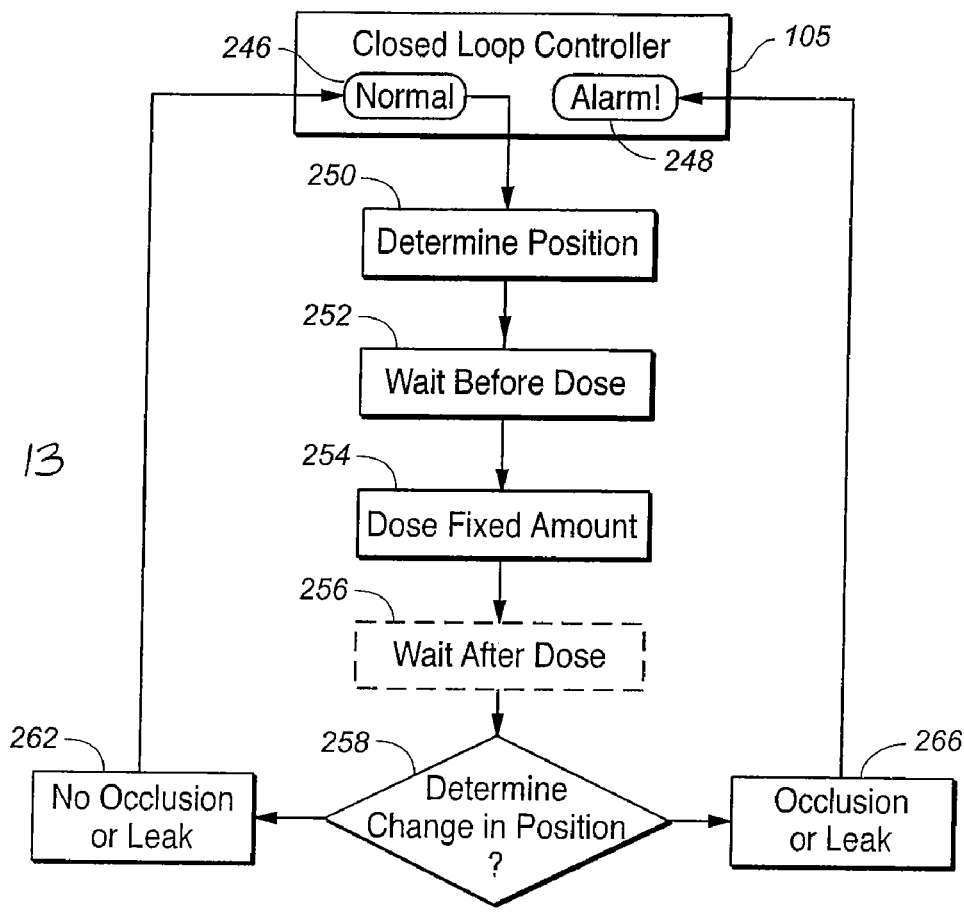
FIG. 13 presents a flow diagram illustrating a method of detecting occlusions in an electrokinetic infusion pump with closed loop control according to an additional embodiment of the present invention.
Figure 14:
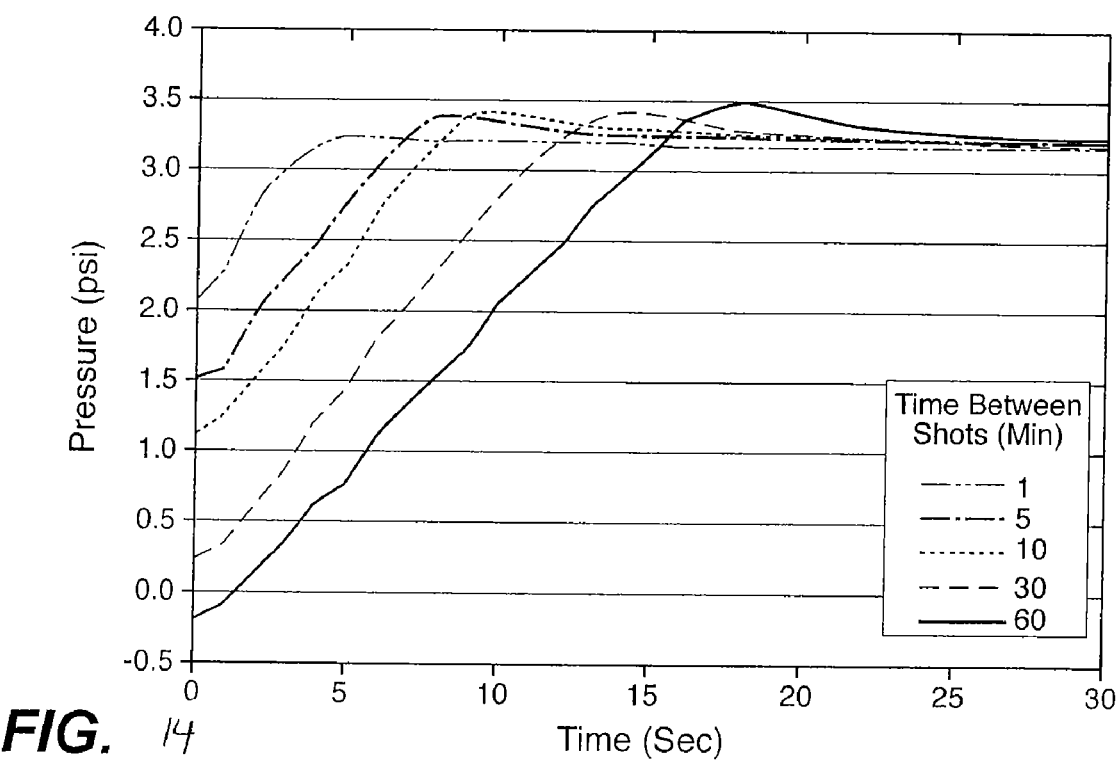
FIG. 14 presents graphs showing back pressure in an electrokinetic infusion pump with closed loop control using various shot waiting times according to embodiments of the present invention.
Figure 15:
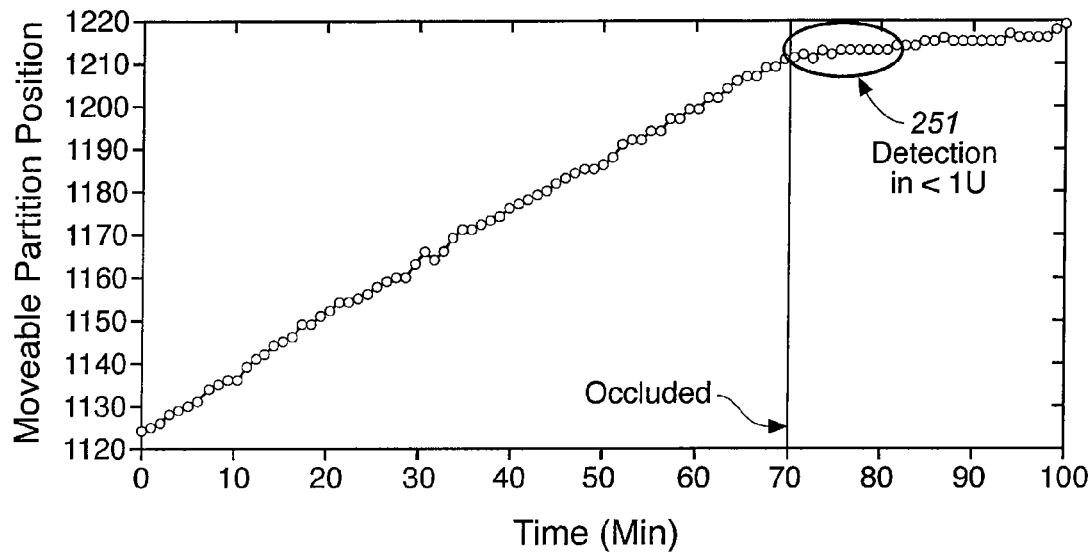
FIG. 15 presents a graph showing the position of a moveable partition as a function of time when an occlusion occurs in an electrokinetic infusion pump with closed loop control according to an embodiment of the present invention.

FIG. 13 is a flow diagram illustrating a method of detecting occlusions in an electrokinetic infusion pump with closed loop control 100 according to an embodiment of the present invention. With reference to FIG. 13, and FIGS. 1A & 1B, closed loop controller 105 starts with a normal status 246. In the next step, closed loop controller 105 determines position 250 of moveable partition 120. After determining the position 250 of moveable partition 120, closed loop controller 105 waits before dose 252. During this time, the pressure in electrokinetic infusion pump 103 decreases. After waiting before dose 252, a fixed volume is dosed 254. This is accomplished by activating the electrokinetic engine 102. As a result of dosing a fixed volume 254 (electrokinetic engine on time), the pressure in electrokinetic infusion pump 103 increases as a function of time, as illustrated in FIG. 14. Multiple graphs are illustrated in FIG. 14, showing the effect of time between shots (electrokinetic engine off time) on pressure in electrokinetic infusion pump 103. Waiting 1 minute between shots results in a rapid build up of pressure. Waiting 5 minutes between shots results in a longer time to build pressure. The rate at which pressure builds is the same in each graph, but the starting pressure decreases as a function of time between shots, and therefore results in longer times to build pressure. Each graph eventually reaches the same approximate pressure, in this case about 3.2 psi. This is the pressure needed to displace moveable partition 120. Returning to FIG. 13, after dosing a fixed amount 254, and waiting after dose 256 (during which time the pressure in electrokinetic infusion pump 103 increases), the change in position 258 of moveable partition 120 is determined. The position of moveable partition 120 can be determined using a variety of techniques, as mentioned previously. After determining the change in position 258 of moveable partition 120, closed loop controller 105 determines if moveable partition 120 has moved as expected 260, or if it has not moved as expected 264. If moveable partition 120 has moved as expected 260, then no occlusion 262 has occurred, and the closed loop controller 105 returns to normal status 246. If the moveable partition 120 has not moved as expected 264, then an occlusion 266 has occurred, and the closed loop controller 105 enters an alarm status 248. FIG. 15 is a graph illustrating the position of moveable partition 120 as a function of time when an occlusion occurs in an electrokinetic infusion pump with closed loop control 100, according to the embodiment described in the previous example (i.e., running with a series of on/off times using feedback control). As can be seen in FIG. 15, after about 70 minutes the rate at which moveable partition 120 moves as a function of time suddenly decreases in region 250. This indicates that an occlusion has occurred, blocking the movement of moveable partition 120.

Example 3

Measurements of Streaming Potential to Detect Occlusions

Figure 16:
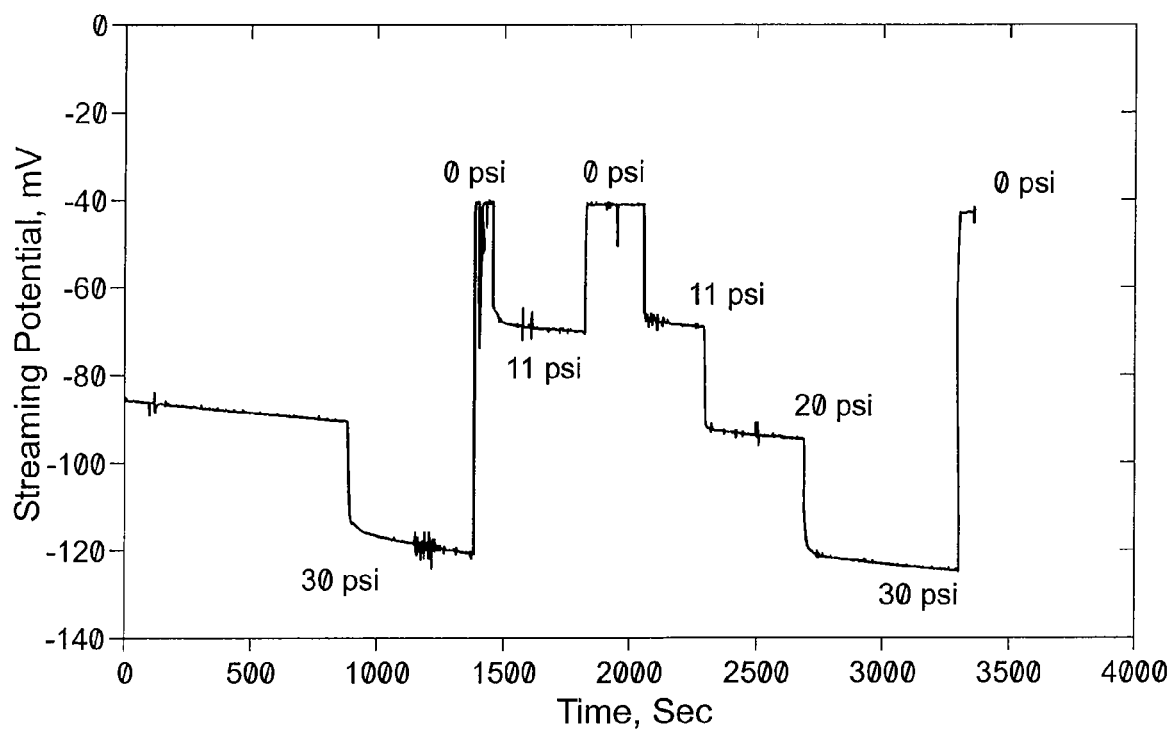
FIG. 16 presents a graph showing streaming potential across first and second electrodes as a function of time and pressure difference across electrokinetic porous media, according to an embodiment of the present invention.

Experiments were conducted in which the streaming potential was measured as a function of pressure difference across a porous membrane (Durapore Z, Millipore Corp., Billerica, Mass.), such as those used in fabricating electrokinetic porous media. FIG. 16 is an illustration of the correlation between pressure difference across electrokinetic porous media and streaming potential, as measured in the experiment.

As illustrated in FIG. 16, the streaming potential is around 3 mV per psi pressure difference, and is consistent with the streaming potential predicted by the Helmholtz-Schmoluchowsky equation. In operating an electrokinetic infusion pump, typical pressures in the electrokinetic solution receiving chamber are on the order of 10 psi. When an occlusion is present, the pressure in electrokinetic solution receiving chamber 118 can increase to about 20 psi. At pressures of 20 psi in the electrokinetic solution receiving chamber, streaming potentials on the order of 30-60 mV can be easily measured, and can be used as an additional indication of occlusion in the infusion reservoir outlet or the infusion tip.

Example 4

Measurements of Current Draw to Detect Occlusions

Figure 17:
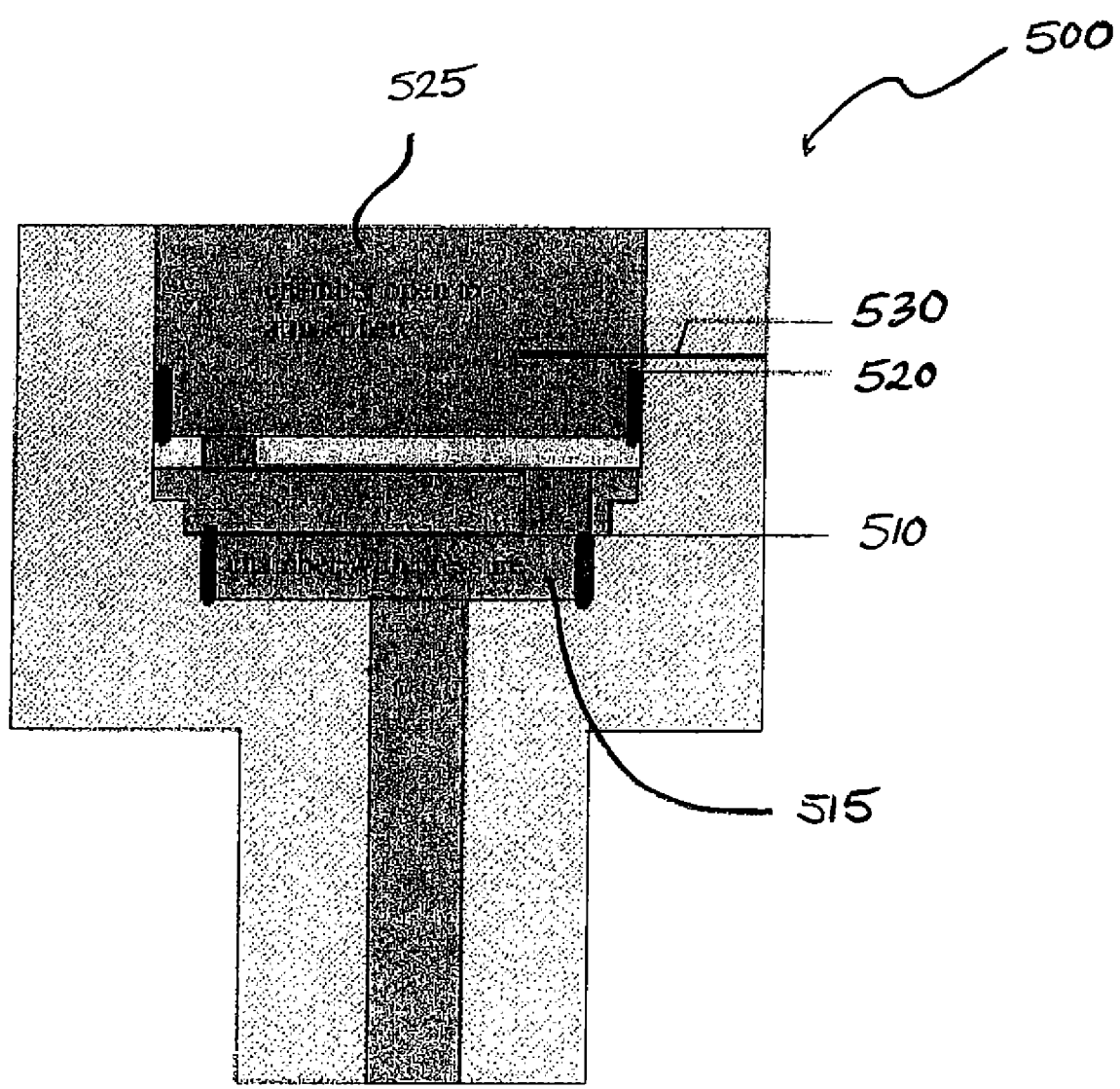
FIG. 17 presents a side-view schematic diagram of an electrokinetic infusion pump corresponding to some embodiments of the present invention.

FIG. 17 presents a schematic cross-sectional diagram of an electrokinetic infusion pump 500 utilized in some experiments discussed herein. Electrokinetic fluid was driven from a supply chamber 525 into a receiving chamber 515 by applying a voltage between a first ring electrode 510 and a second ring electrode 520. An alternate electrode 530 served as a reference electrode for performing accurate measurements if the second ring electrode's decay was not sufficiently uniform. In the experiments conducted with the electrokinetic infusion pump 500 of FIG. 17, electrodes 510, 520 are used to measure the open circuit potential (herein "OCP") decays during the power off phase of a cycle, and the streaming potential was obtained from difference from the various OCP decays at different shots after an occlusion was present.

Figure 18:
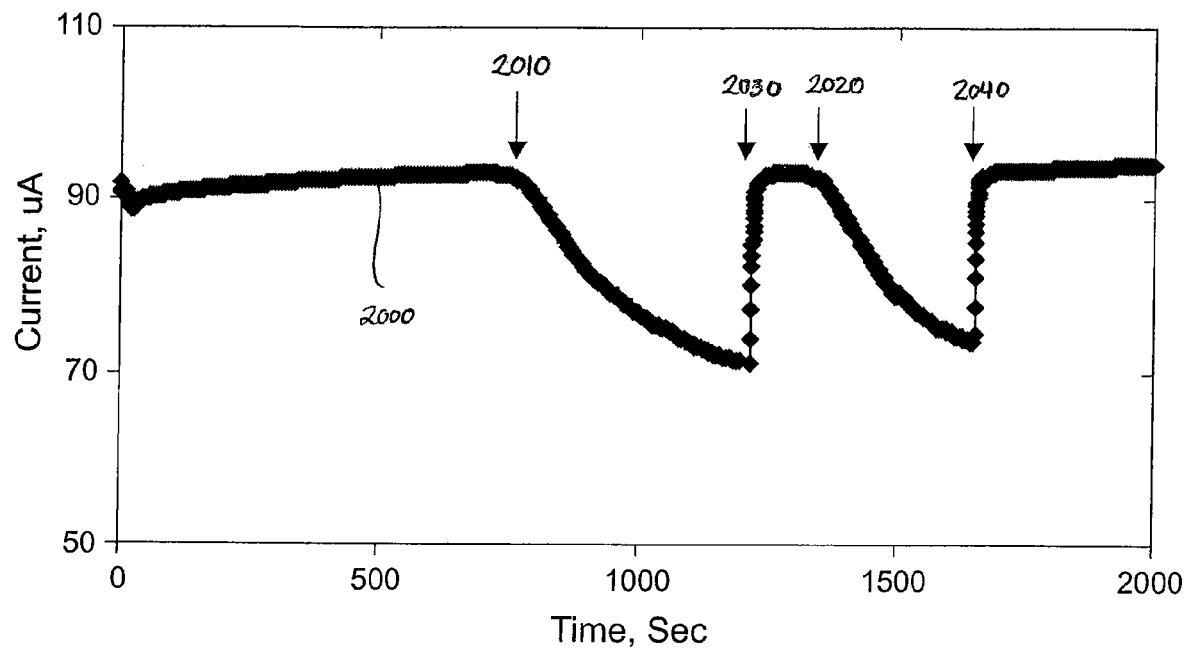
FIG. 18 presents a graph illustrating current draw through electrokinetic porous media as a function of time, before and after an occlusion, according to an embodiment of the present invention.
Figure 19:
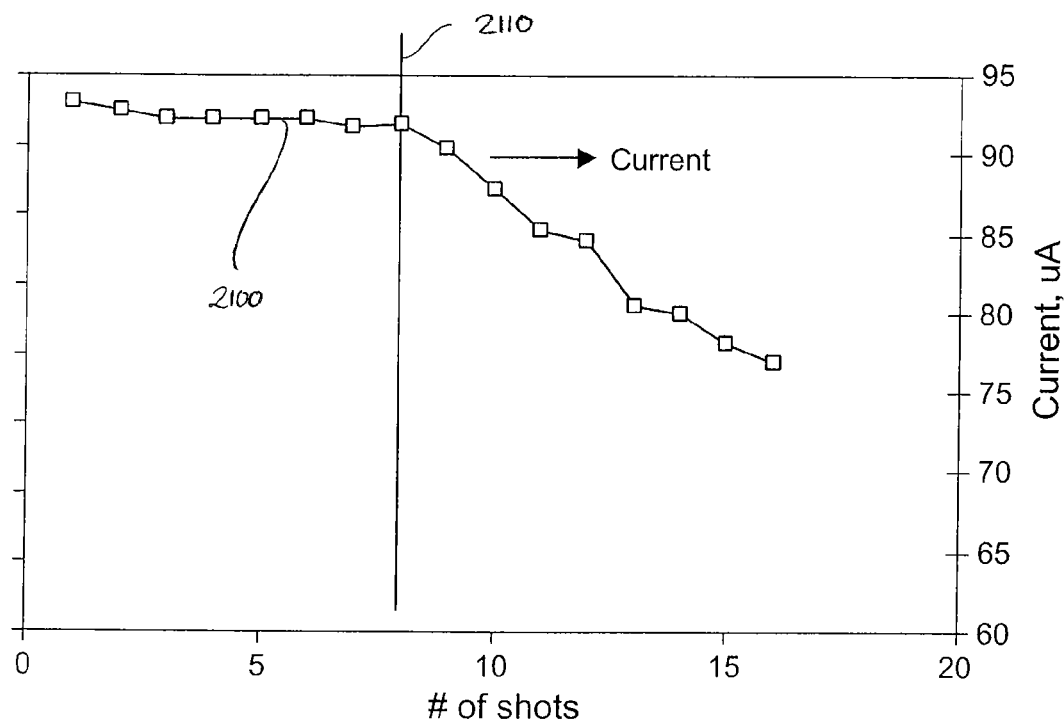
FIG. 19 presents a graph illustrating current draw through electrokinetic porous media as a function of pump cycles, before and after an occlusion, according to an embodiment of the present invention.

FIGS. 18 and 19 present measurements of current draw through the electrokinetic porous media of the electrokinetic infusion pump diagrammed in FIG. 17 before and after an occlusion occurred in infusion reservoir outlet, as recorded using LabView software. Occlusions were induced by applying a hemostat to clamp the infusion set carrying infusion fluid away from the pump. In the experiments illustrated by FIGS. 18 and 19, 75 volts was applied across the electrodes while the current across electrokinetic porous media was measured during pump on time, before and after an occlusion in infusion reservoir outlet occurred. In FIG. 18, current draw through the electrokinetic porous media is plotted as a function of time for an experiment where the voltage between the electrodes was applied continuously. In particular, arrows 2010, 2020 indicate moments where the hemostat was applied to induce an occlusion, while arrows 2030, 2040 indicate moments where the hemostat was removed to allow infusion fluid to flow without obstruction. In FIG. 19, current draw through the electrokinetic porous media is plotted as a function of number of pump cycles, i.e., the pump was operated in a non-continuous flow mode where power was turned on for 10 seconds and turned off for 50 seconds. Each current measurement was performed at a time of about 4 seconds after power was applied. The vertical line 2110 indicates the moment when a hemostat was applied to induce an occlusion in the system.

As indicated by the plateau in the graphs 2000, 2100 before the moments 2010, 2110 when an occlusion was induced by a hemostat, current draw across the electrokinetic porous media was fairly constant as shown in FIGS. 18 and 19. After the moment 2010, 2110 when an occlusion was induced, the current draw across electrokinetic porous media dropped sharply. As shown in FIG. 18, when the occlusion was removed 2030, the current draw across electrokinetic porous media rapidly returned to its previous level. When the infusion reservoir outlet was occluded again at moment 2020, current draw across electrokinetic porous media dropped sharply, and when the occlusion was removed at moment 2040, current draw across electrokinetic porous media returned to its previous level. Thus, the examples illustrated by FIGS. 18 and 19 demonstrate a correlation between current draw through electrokinetic porous media and occlusions in infusion reservoir outlet.

Example 5

Measurements of Pressure and Current Transients to Detect Occlusions

In this example, an electrokinetic infusion pump, as described earlier with respect to FIG. 17, was operated using activate/de-activate cycling. Shot durations of about 4.5 seconds were used, with a total cycle time of about 1 minute. Infusion liquid at delivered at a rate of about 0.5 microliters/minute, amounting to a basal delivery rate of about 3 microliters/hour. Pressure in the electrokinetic solution receiving chamber and current draw through electrokinetic porous media were measured during pump on time. The occlusion was induced by completely blocking the infusion set tube. Data were collected on two control situations of an electrokinetic infusion pump: a closed loop control scheme (FIG. 20) and an open loop scheme (FIG. 21).

Figure 20:
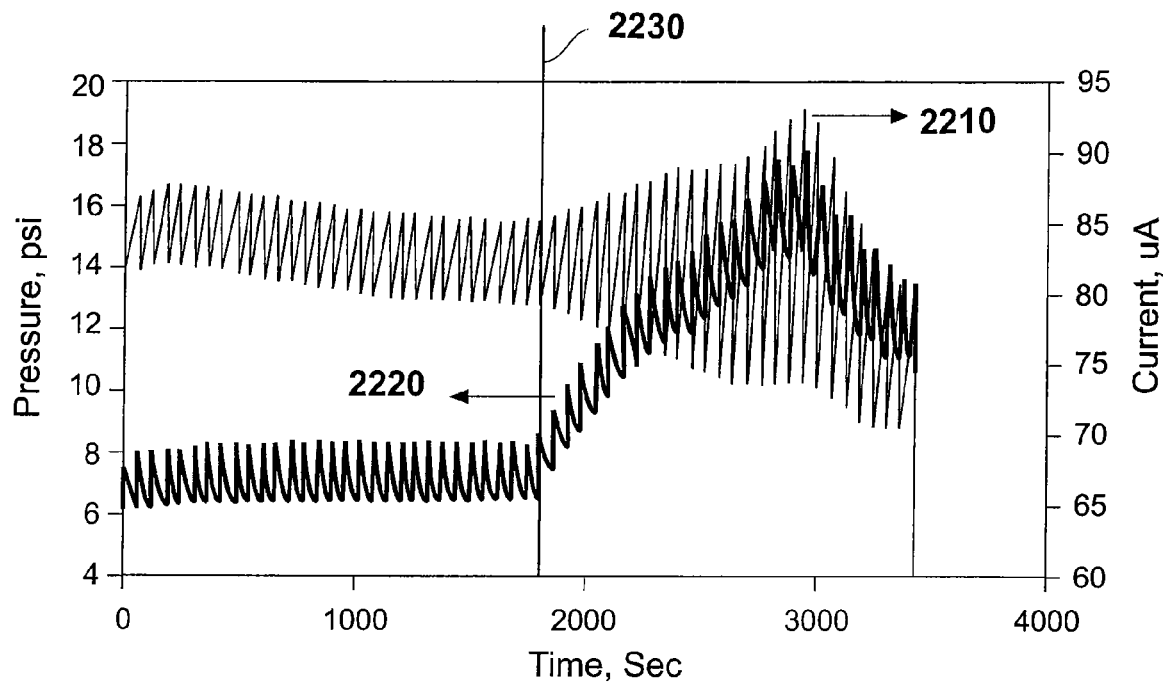
FIG. 20 presents a graph showing current draw through electrokinetic porous media and pressure in an electrokinetic solution receiving chamber as a function of time, before and after an occlusion, according to an embodiment of the present invention.

FIG. 20 presents a graph of the pressure measured in electrokinetic solution receiving chamber and the measured current draw through electrokinetic porous media as a function of time, before and after an occlusion in the infusion reservoir outlet of an electrokinetic infusion pump operated with closed loop control. In FIG. 20, the current draw 2210 and the pressure profile 2220 both appear as bands formed from an oscillating graph due to the cyclic current decay during pump on time and off time. Current decay during pump on time was in part caused by time dependent charging of the electrodes, as mentioned previously with respect to Equation 4. Before the moment when an occlusion was induced 2230, the amplitudes of the pressure profile in electrokinetic solution receiving chamber and the current draw through electrokinetic porous media were relatively constant, showing fairly uniform band thicknesses. After an occlusion in infusion reservoir outlet occurs 2230, the pressure in electrokinetic solution receiving chamber rose sharply, while the average current draw through electrokinetic porous media decreased. The band width of current draw through electrokinetic porous media, also referred to as current decay, however, increased significantly. The initial current draw reading drifted higher and the final current draw reading drifted lower, with the difference between them increasing with time. This behavior suggests that current decay may also be used as an indicator of occlusions in infusion reservoir outlet for electrokinetic infusion pump with closed loop control operating in closed loop mode.

Figure 21:
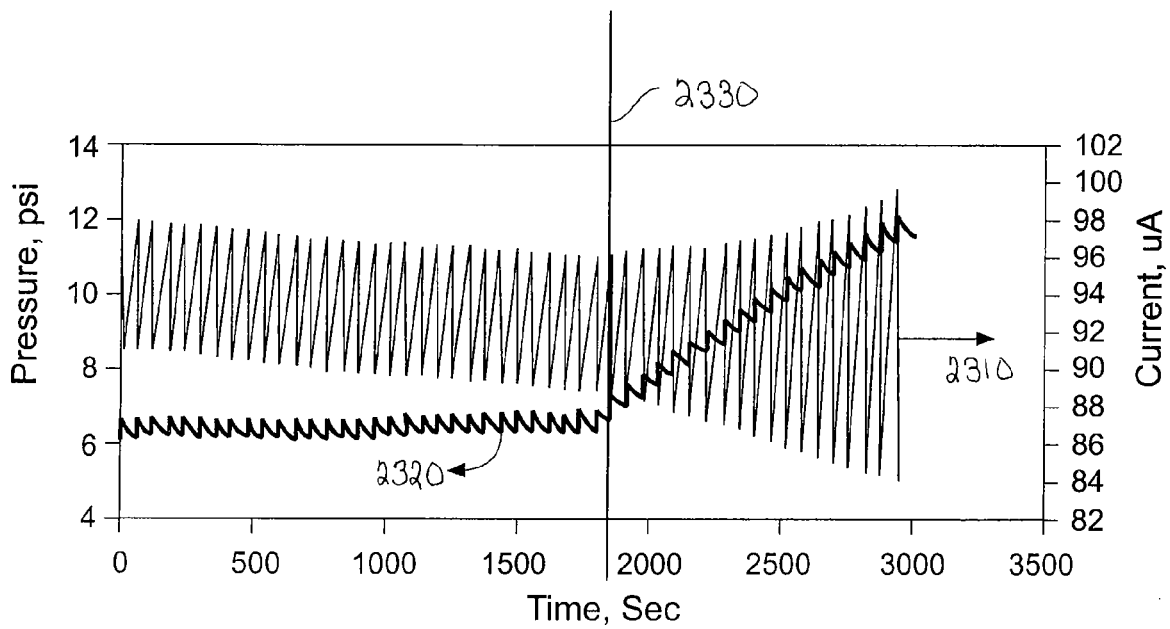
FIG. 21 presents a graph showing current draw through electrokinetic porous media and pressure in an electrokinetic solution receiving chamber as a function of time, before and after an occlusion, according to another embodiment of the present invention.

FIG. 21 illustrates the pressure in an electrokinetic solution receiving chamber and the current draw through electrokinetic porous media as a function of time, before and after an occlusion in the infusion reservoir outlet of an electrokinetic infusion pump operated in an open loop mode. The several qualitative features of FIG. 21 mimic the features shown for the closed loop control case in FIG. 20. Before the moment when an occlusion is induced 2330, the amplitudes of the pressure in electrokinetic solution receiving chamber 2320 and the current draw through electrokinetic porous media 2310 are relatively constant, showing fairly uniform band thicknesses. After an occlusion in infusion reservoir outlet occurred 2330, pressure in electrokinetic solution receiving chamber rose sharply, while the average current draw through electrokinetic porous media decreased. Decay of current draw through electrokinetic porous media increased significantly, with initial current draw drifting higher, final current draw drifting lower, and the difference between initial and final current draw increasing with time. This behavior demonstrates that decay of current draw through electrokinetic porous media may be used as an indicator of occlusions in an electrokinetic infusion pump operating in open loop mode. The increase in decay of current draw through electrokinetic porous media after occlusion could, in part, be due to reduced flow of electrokinetic solution across electrokinetic porous media during pump on time, and increased backflow across electrokinetic porous media during pump off time. Also, changes in the conductivity of electrokinetic solution, and joule heating of electrokinetic solution, may also have contributed to increases in current decay following occlusions in infusion reservoir outlet.

Example 6

Measurements of Current Draw and Current Transients to Detect Occlusions

In this example, an electrokinetic infusion pump, as described earlier with respect to FIG. 17, was operated using a closed loop controller and activate/de-activate cycling. In a first run, infusion liquid was delivered at a rate of about 0.15 microliters/minute, with a shot size of about 0.5 microliters, and a total cycle time of 200 seconds. In a second run, infusion liquid was delivered at a rate of about 5.8 microliters/minute, with a shot size of about 5.8 microliters, and a total cycle time of 60 seconds. Current draw and decay measurements through electrokinetic porous media were measured during pump on time using LabView software. The occlusion was induced by completely blocking the infusion set tube.

Figure 22:
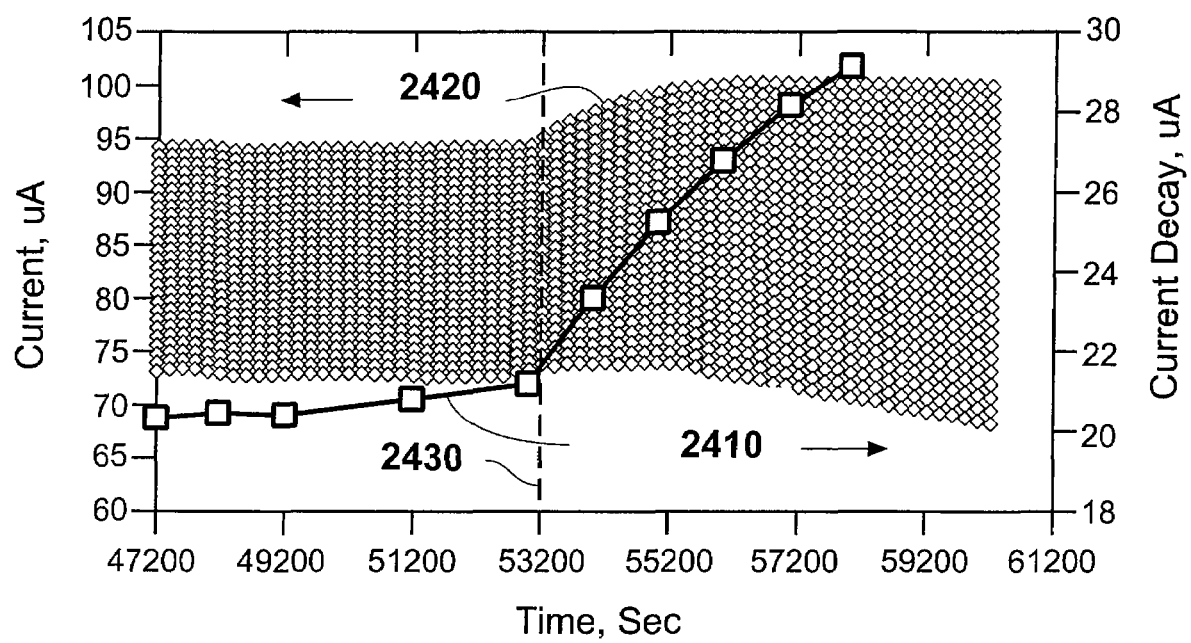
FIG. 22 presents a graph showing current draw through electrokinetic porous media and decay in current draw through electrokinetic porous media, as a function of time, before and after an occlusion, according to an embodiment of the present invention.
Figure 23:
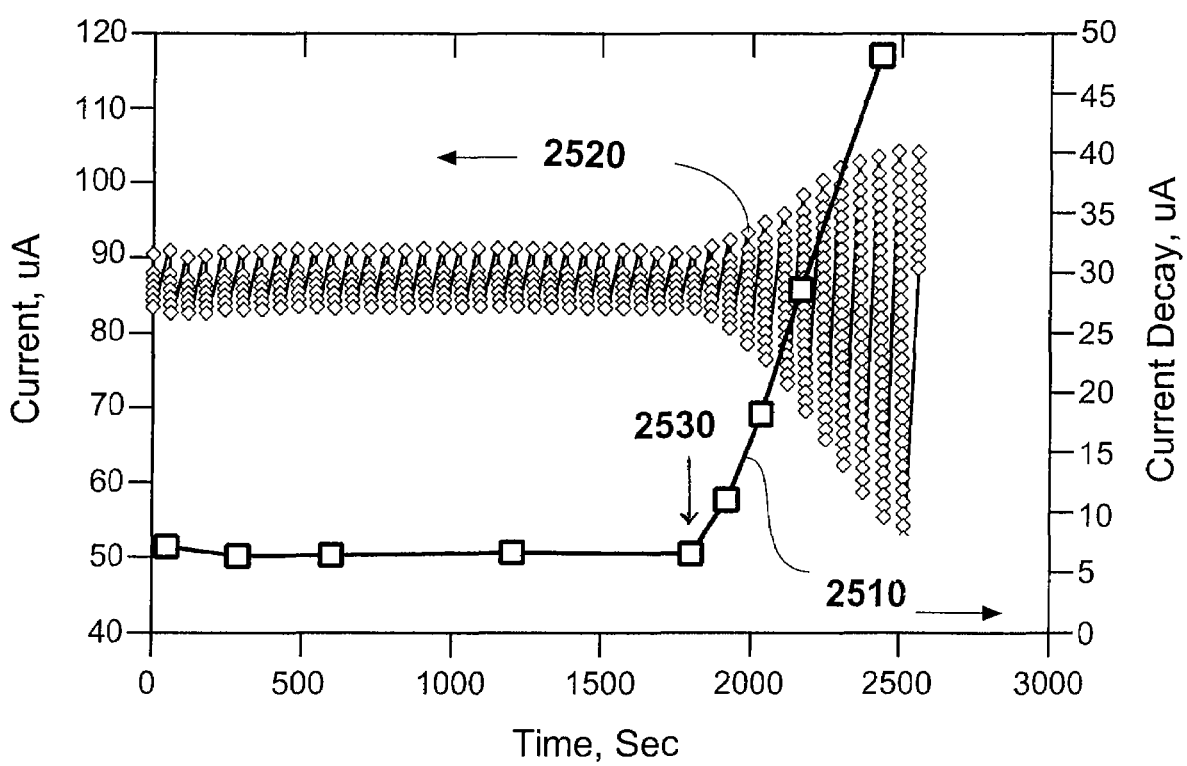
FIG. 23 presents a graph showing current draw through electrokinetic porous media and decay in current draw through electrokinetic porous media, as a function of time, before and after an occlusion, according to another embodiment of the present invention.

FIGS. 22 and 23 show graphs of current and current decay as a function of time for the first and second runs, respectively. In FIG. 22, the band of data 2420 refers to current draw measurements, while the graph 2410 represents values corresponding with a current decay value calculated at a designated moment after an activate phase has started. An occlusion is induced by blocking the infusion set at a marked moment 2430. In FIG. 23, the band of data 2520 refers to current draw measurements, while the graph 2510 represents values corresponding with a current decay value calculated at a designated moment after an activate phase has started. An occlusion is induced by blocking the infusion set at a marked moment 2530. Both figures show the increase in current decay, and the overall general decrease in current draw, after an occlusion is initiated.

Example 7

Measurements of Pressure and Current Transients to Detect Occlusions

In this example, an electrokinetic infusion pump, as described earlier with respect to FIG. 17, was operated using activate/de-activate cycling. Shot durations of about 5 seconds were used, with a total cycle time of about 1 minute. Corresponding with FIG. 24, before time moment 2630, a constant backpressure was induced in the infusion set of 1.6 psi. After time moment 2630, the induced backpressure in the infusion set was released to zero. This change in backpressure was used to simulate a leak in the infusion set. The infusion fluid pressure measurements were taken at moments just before the end of an activate/de-activate cycle, or just before the next shot. The current draw was measured during the activate portion of a cycle.

Figure 24:
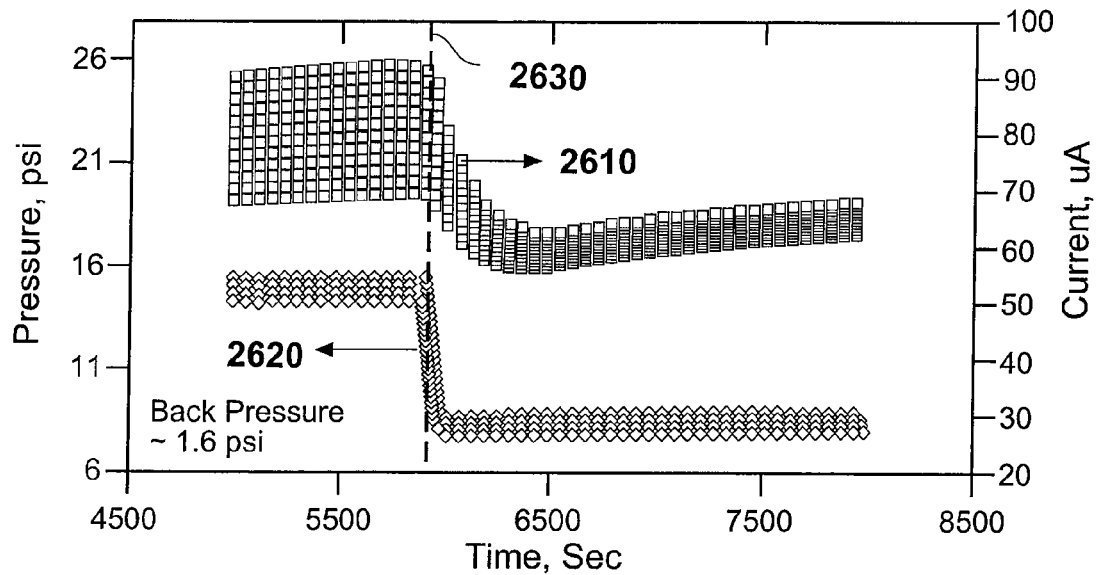
FIG. 24 presents a graph showing current draw through electrokinetic porous media and pressure in an infusion reservoir as a function of time, before and after a leak, according to an embodiment of the present invention.

FIG. 24 shows graphs of the pressure measurements 2630 and current measurements 2610 as a function of time before and after the backpressure is released in the infusion set. Upon backpressure release, the pressure in the infusion reservoir receiving chamber drops from about 14.5 psi to about 8 psi. This drop of about 6.4 psi corresponds to the 1.6 psi backpressure release due to the fact that a 4:1 plunger design was utilized with the electrokinetic infusion pump. A sharp decrease in current draw through the electrokinetic porous media is noticed (~16 µA), as well as a decrease in the magnitude of the current decay, after the backpressure is released. According, a drop of about 2.5 µA/psi is observed.

Example 8

Measurements of Open Circuit Potential Transients and Partition Position to Detect Occlusions In this example, an electrokinetic infusion pump, as described earlier with respect to FIG. 17, was operated using a closed loop controller and activate/de-activate cycling. In a first run, corresponding with the conditions in Example 6 for FIG. 22, infusion liquid was delivered at a rate of about 0.15 microliters/minute, with a shot size of about 0.5 microliters, and a total cycle time of 200 seconds. In a second run, corresponding with the conditions in Example 6 for FIG. 23, infusion liquid was delivered at a rate of about 5.8 microliters/minute, with a shot size of about 5.8 microliters, and a total cycle time of 60 seconds. The position of the partition used to drive infusion fluid, and open circuit voltage measurements during pump off time across the electrokinetic porous media, were measured using LabView software. The occlusion was induced by completely blocking the infusion set tube.

Figure 25:
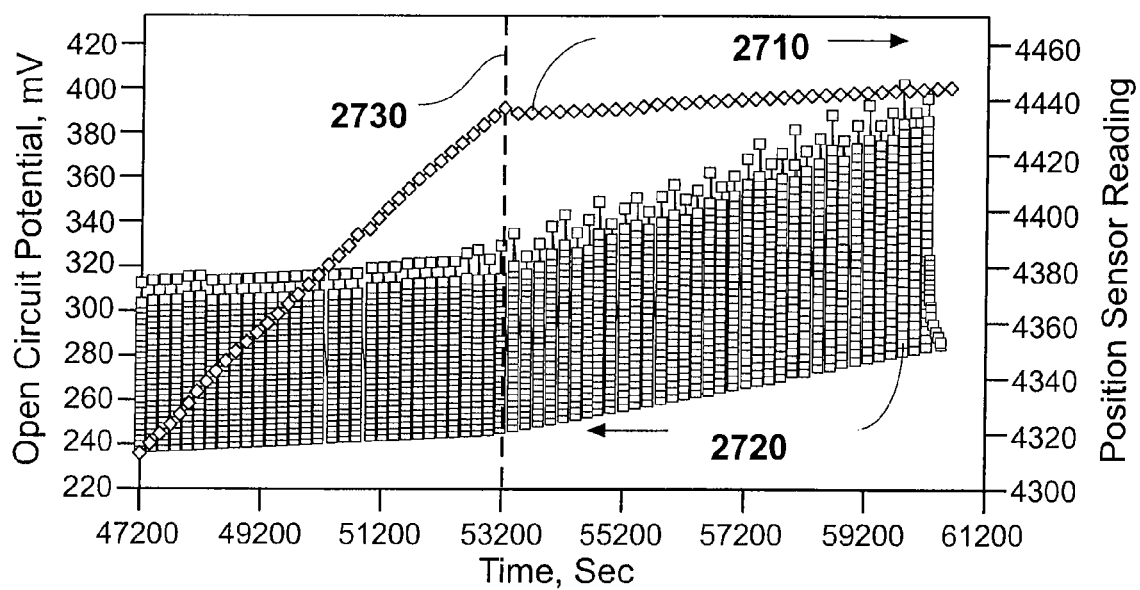
FIG. 25 presents a graph showing open circuit potential across first and second electrodes and the position of a moveable partition as a function of time, before and after an occlusion, according to an embodiment of the present invention.
Figure 26:
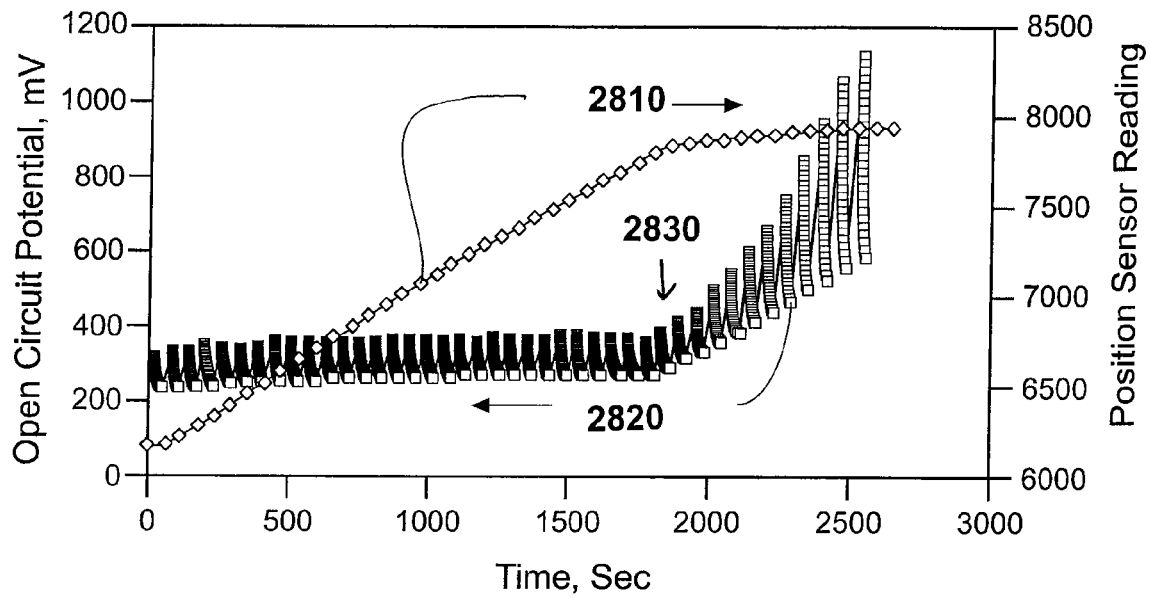
FIG. 26 is a graph showing open circuit potential across first and second electrodes and the position of a moveable partition as a function of time, before and after an occlusion, according to an embodiment of the present invention.

In FIGS. 25 and 26, position sensor readings of the movable partition, and open circuit potential across first electrode and second electrode during pump off time, are plotted as a function of time, before and after an occlusion occurs in infusion reservoir outlet. As illustrated in FIGS. 25 and 26, the rate at which position sensor readings 2710, 2810, respectively, of the movable partition change as a function of time decreases sharply after the moment when the infusion reservoir outlet is occluded 2730, 2830. Similarly, the open circuit potential and the open circuit potential decay across the electrodes during pump off time sharply increase after an occlusion occurs in infusion reservoir outlet.

Example 9

Measurements of Open Circuit Potential Transients and Pressure to Detect Leaks

In this example, an electrokinetic infusion pump, as described earlier with respect to FIG. 17, was operated using activate/de-activate cycling. Conditions were the same as described for Example 7, with shot durations of about 5 seconds, with a total cycle time of about 1 minute. Corresponding with FIG. 27, before time moment 2930, a constant backpressure was induced in the infusion set of 1.6 psi. After time moment 2930, the induced backpressure in the infusion set was released to zero during pump off time. This change in backpressure was used to simulate a leak in the infusion set. The infusion fluid pressure measurements were taken at moments just before the end of an activate/de-activate cycle, or just before the next shot. The open circuit potential was measured during the de-activate portion of a cycle.

Figure 27:
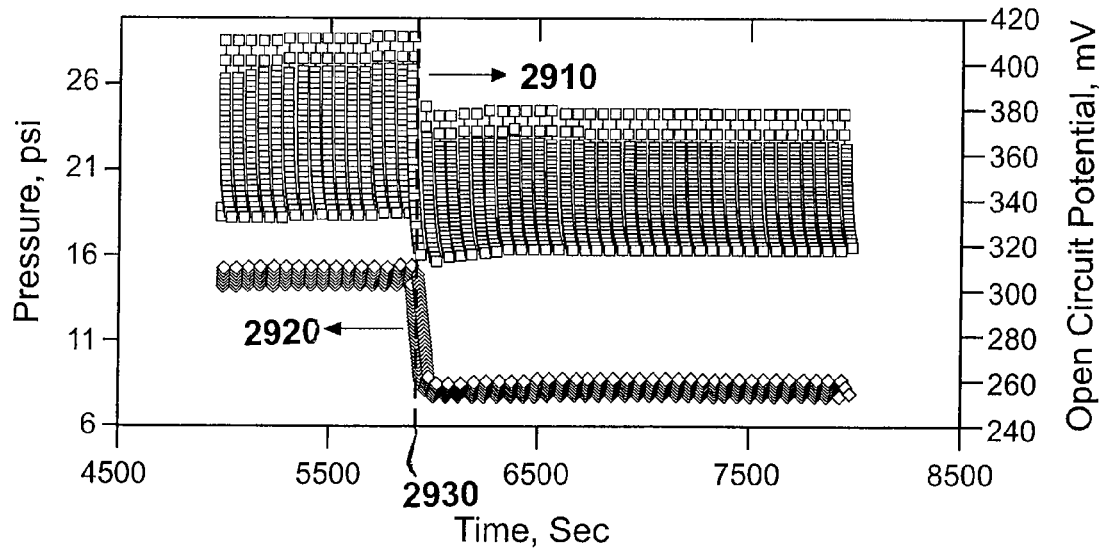
FIG. 27 presents a graph showing open circuit potential across first and second electrodes and pressure in an infusion reservoir as a function of time, before and after a leak, according to an embodiment of the present invention.

FIG. 27 shows graphs of the pressure in electrokinetic solution receiving chamber 2920 and open circuit potential across the electrodes during pump off time 2910 as a function of time, before and after backpressure is released in the infusion reservoir outlet. When backpressure is released in the infusion reservoir outlet 2930, the pressure in infusion reservoir 2920 sharply decreases, causing a proportional decrease in the pressure in electrokinetic solution receiving chamber. The release of backpressure also results in a sharp decrease in open circuit potential across the electrodes. At least in part, the sharp decrease in open circuit potential across the electrodes is due to a decrease in streaming potential across electrokinetic porous media. As illustrated in FIG. 27, there is a pronounced correlation between a leak in electrokinetic solution receiving chamber, infusion reservoir, and infusion reservoir outlet, and open circuit potential across electrodes during pump off time. This correlation can be used to detect leaks in an electrokinetic infusion pump.

Example 10

Measurements of Open Circuit Potential and Current Transients to Detect Occlusions In this example, an electrokinetic infusion pump, as described earlier with respect to FIG. 17, was operated using activate/de-activate cycling. The conditions of this experiment are identical to the conditions utilized to generate the data of FIG. 19. In particular, 75 volts was applied across the electrodes during pump on time. Power was cycled with 10 seconds on time and 50 seconds off time. The current was measured about 4 seconds after power was turned on, while open circuit potential was measured about 15 seconds after power was turned off. An occlusion was induced by applying a hemostat to clamp the infusion set carrying infusion fluid away from the pump.

Figure 28:
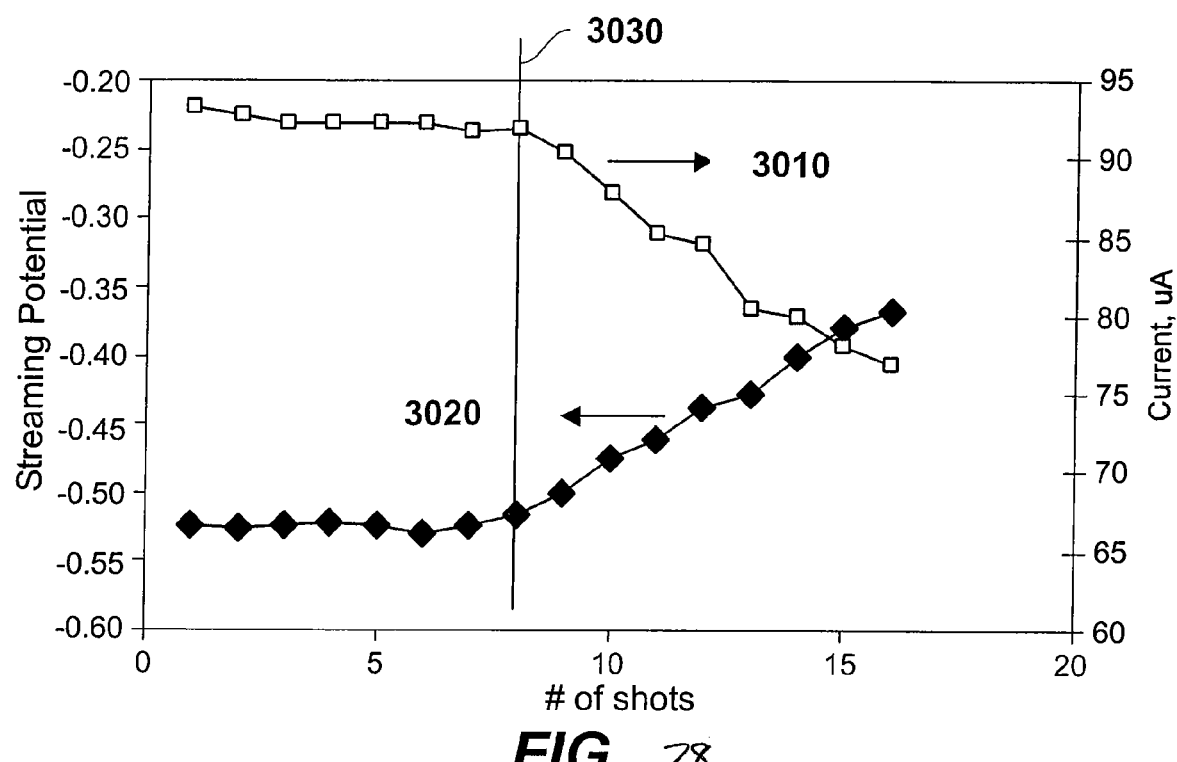
FIG. 28 presents a graph showing current draw through electrokinetic porous media and open circuit potential across first and second electrodes as a function of pump cycles, before and after an occlusion, according to an embodiment of the present invention.

FIG. 28 graphs the magnitude of current transients through the electrokinetic porous media during pump on time 3010 and the magnitude of open circuit potential transients across the electrodes during pump off time 3020 as a function of pump cycles (or shots), before and after the moment 3030 when occlusion is induced in the infusion reservoir outlet. As illustrated in FIG. 28, the magnitude of the current transient through electrokinetic porous media during pump on time abruptly decreases after an occlusion occurs. Similarly, the magnitude of the open circuit potential transient across the electrodes during pump off time changes abruptly, due in part to streaming potential across electrokinetic porous media.

Example 11

Bubble Formation Detection Using Open Circuit Potential Measurements

Figure 29:
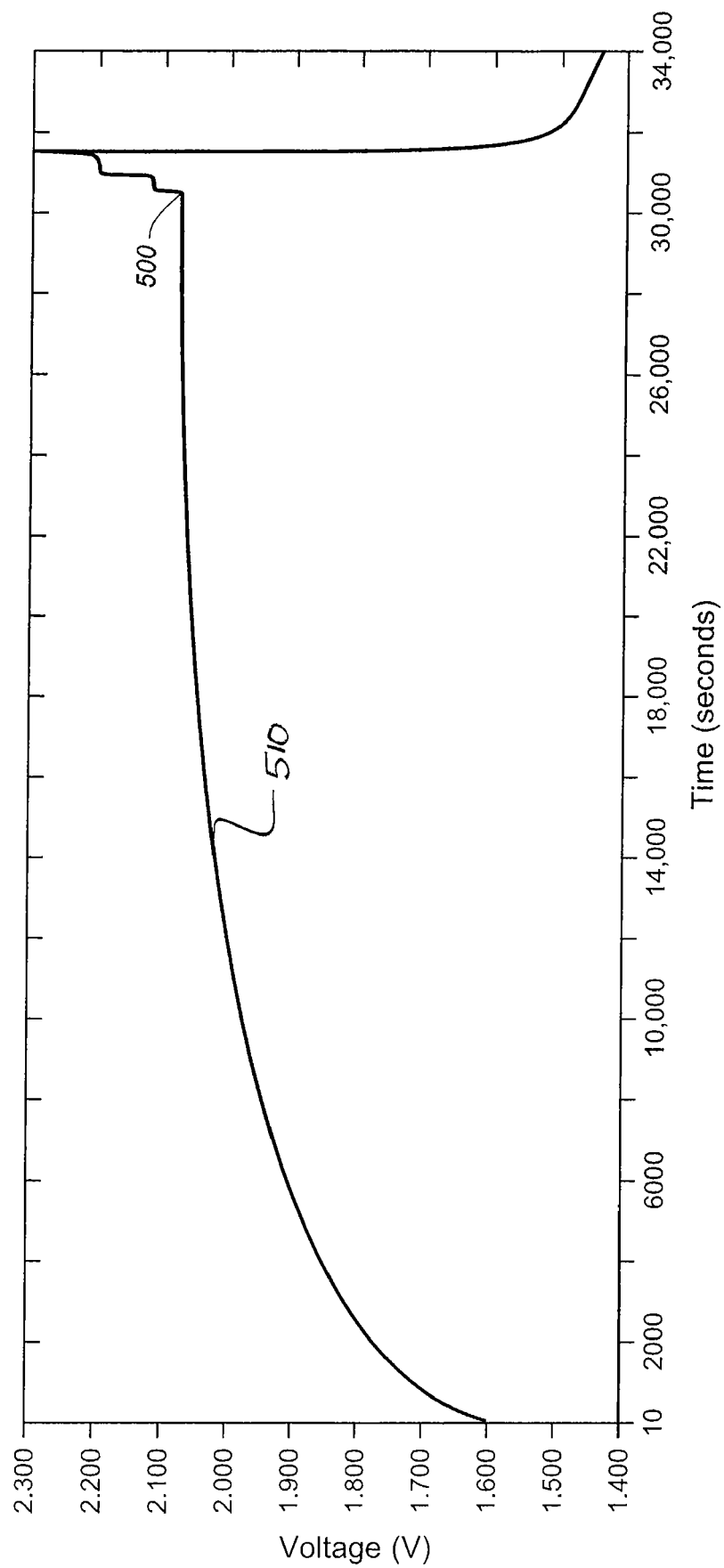
FIG. 29 presents a graph showing the voltage across capacitive electrodes while being charged, as used in an electrokinetic infusion pump with closed loop control in embodiments of the present invention.

FIG. 29 presents a graph of an open-circuit potential measurement as a function of time during the charging of capacitive electrodes during a closed volume electrode test. The trace 510 follows the data indicating voltage values at zero applied current. At a time moment 500 corresponding to about 30,000 seconds, the trace 510 deviates substantially from the asymptoting charging curve. Thus, the deviation can be indicative of the onset of gas generation on a capacitive electrode.

What is claimed is:

1. A system for detecting a malfunction in an infusion fluid delivery apparatus, comprising:
   an infusion pump coupled to electrodes, the electrodes configured to provide a measurement between opposite sides of a porous media; and
   a processor coupled to the infusion pump, the processor configured to provide an indication of pump malfunction based at least on a comparison between the measurement and at least one sample value.

2. The system of claim 1, wherein the infusion pump is configured to drive infusion fluid flow with flow of an electrokinetic working fluid.

3. The system of claim 1, wherein the electrodes and processor are configured as a electrokinetic sensing device independent of a drive mechanism of the infusion pump.

4. The system of claim 1, further comprising:
   an alert mechanism coupled to the processor, the processor configured to activate the alert mechanism if pump malfunction is indicated.

5. The system of claim 1, wherein at least one of the electrodes is a capacitive electrode.

6. The system of claim 1, wherein at least one of the electrodes is configured to apply a driving voltage to cause electrokinetic fluid to flow through the porous media.

7. The system of claim 1, wherein at least one of the electrodes is a measurement electrode only.

8. The system of claim 1, wherein the electrodes are configured to provide an open-circuit voltage measurement between opposite sides of the porous media.

9. The system of claim 1, wherein the electrodes are configured to provide a current draw measurement between opposite sides of the porous media.

10. The system of claim 1, wherein the processor comprises at least one memory configured to store the at least one sample value and the measurement.

11. The system of claim 10, wherein the processor is configured to write at least one sample value to the at least one memory based upon at least one measured value obtained from the electrodes.

12. The system of claim 10, wherein the at least one memory is configured to store electrode transients corresponding to the at least one sample voltage value and an electrode voltage measurement.

* * * * *